(12) United States Patent
Patzak et al.

(10) Patent No.: US 10,485,787 B2
(45) Date of Patent: Nov. 26, 2019

(54) ORAL DOSAGE FORMS OF BENDAMUSTINE AND THERAPEUTIC USE THEREOF

(71) Applicant: ASTELLAS DEUTSCHLAND GMBH, Munich (DE)

(72) Inventors: Ulrich Patzak, Leiderdorp (NL); Taoufik Ouatas, Leiderdorp (NL)

(73) Assignee: Astellas Deutschland GmbH, Munich (DE)

( * ) Notice: Subject to any disclaimer, the term of this patent is extended or adjusted under 35 U.S.C. 154(b) by 0 days.

(21) Appl. No.: 14/661,693

(22) Filed: Mar. 18, 2015

(65) Prior Publication Data

US 2015/0258070 A1 Sep. 17, 2015

Related U.S. Application Data

(63) Continuation of application No. 13/701,228, filed as application No. PCT/EP2011/002763 on Jun. 1, 2011, now abandoned.

(30) Foreign Application Priority Data

Jun. 2, 2010 (EP) .................................... 10005762
Mar. 14, 2011 (EP) .................................... 11075046

(51) Int. Cl.
| | | |
|---|---|---|
| *A61K 9/00* | (2006.01) | |
| *A61K 31/00* | (2006.01) | |
| *A61K 31/4184* | (2006.01) | |
| *A61K 9/16* | (2006.01) | |
| *A61K 9/20* | (2006.01) | |
| *A61K 9/28* | (2006.01) | |
| *A61K 9/48* | (2006.01) | |
| *A61K 47/10* | (2017.01) | |
| *A61K 45/06* | (2006.01) | |
| *A61K 31/475* | (2006.01) | |
| *A61K 31/573* | (2006.01) | |
| *A61K 39/395* | (2006.01) | |
| *A61K 9/14* | (2006.01) | |

(52) U.S. Cl.
CPC ........ *A61K 31/4184* (2013.01); *A61K 9/1623* (2013.01); *A61K 9/2018* (2013.01); *A61K 9/2072* (2013.01); *A61K 9/2846* (2013.01); *A61K 9/485* (2013.01); *A61K 9/4808* (2013.01); *A61K 9/4825* (2013.01); *A61K 9/4858* (2013.01); *A61K 9/4866* (2013.01); *A61K 31/475* (2013.01); *A61K 31/573* (2013.01); *A61K 39/39558* (2013.01); *A61K 45/06* (2013.01); *A61K 47/10* (2013.01); *A61K 9/145* (2013.01)

(58) Field of Classification Search
CPC ............ A61M 25/007; A61M 25/0075; A61K 31/4184; A61K 31/475; A61K 31/573; A61K 39/39558; A61K 45/06; A61K 47/10; A61K 9/145; A61K 9/1623; A61K 9/2018; A61K 9/2072; A61K 9/2846; A61K 9/4808; A61K 9/4825; A61K 9/485; A61K 9/4858; A61K 9/4866
See application file for complete search history.

(56) References Cited

U.S. PATENT DOCUMENTS

| | | | | |
|---|---|---|---|---|
| 6,645,528 B1 * | 11/2003 | Straub | .................. | A61K 9/1611 |
| | | | | 424/489 |
| 2001/0046504 A1 * | 11/2001 | Engel | .................. | A61K 9/2846 |
| | | | | 424/400 |
| 2003/0077297 A1 | 4/2003 | Chen et al. | | |
| 2003/0105141 A1 | 6/2003 | Gao et al. | | |
| 2004/0072889 A1 * | 4/2004 | Masferrer | ............ | A61K 31/135 |
| | | | | 514/406 |
| 2004/0157928 A1 * | 8/2004 | Kim | ..................... | A61K 9/4858 |
| | | | | 514/570 |

(Continued)

FOREIGN PATENT DOCUMENTS

| | | |
|---|---|---|
| WO | 2006/065392 A2 | 6/2006 |
| WO | 2006/076620 A2 | 7/2006 |

(Continued)

OTHER PUBLICATIONS

Dirven et al. (Chemical Research in Toxicology 1996, 9(2):pp. 351-360).*
Ansel (Pharmaceutical Dosage Forms and Drug Delivery Systems. 1999, 7th Edition pp. 89-91; 4 pages).*
Strickley (Pharm Res. 2004;21(2):201-230).*
Ash (Handbook of Fillers, Extenders, and Diluents 2007 ;p. 135). (Year: 2007).*
Cheson et al. (Journal of Clinical Oncology; 2009;27(9):1492-1501) (Year: 2009).*

(Continued)

*Primary Examiner* — Ernst V Arnold
(74) *Attorney, Agent, or Firm* — Morgan, Lewis & Bockius LLP

(57) ABSTRACT

In the present invention there is provided a pharmaceutical composition for oral administration which comprises bendamustine or a pharmaceutically acceptable, ester, salt or solvate thereof as an active ingredient, and a pharmaceutically acceptable excipient and which shows a dissolution of the bendamustine of at least 60% in 20 minutes, 70% in 40 minutes and 80% in 60 minutes, as measured with a paddle apparatus at 50 rpm according to the European Pharmacopoeia in 500 ml of a dissolution medium at a pH of 1.5. The invention further relates to the above pharmaceutical composition for use for the oral treatment of a medical condition which is selected from chronic lymphocytic leukemia, acute lymphocytic leukaemia, chronic myelocytic leukaemia, acute myelocytic leukaemia, Hodgkin's disease, non-Hodgkin's lymphoma, multiple myeloma, breast cancer, ovarian cancer, small cell lung cancer and non-small cell lung cancer.

18 Claims, 4 Drawing Sheets

(56) References Cited

U.S. PATENT DOCUMENTS

| | | | | |
|---|---|---|---|---|
| 2004/0197324 | A1* | 10/2004 | Liu | A61K 9/0019 424/130.1 |
| 2006/0051412 | A1* | 3/2006 | Petereit | A61K 9/0056 424/464 |
| 2006/0052270 | A1 | 3/2006 | Patel et al. | |
| 2006/0128777 | A1 | 6/2006 | Bendall et al. | |
| 2006/0159713 | A1 | 7/2006 | Brittain et al. | |
| 2009/0017024 | A1 | 1/2009 | Estok | |
| 2009/0264488 | A1 | 10/2009 | Cooper et al. | |
| 2009/0324552 | A1 | 12/2009 | Lichter et al. | |
| 2010/0209927 | A1* | 8/2010 | Menon | B01L 3/5027 435/6.16 |
| 2010/0273730 | A1* | 10/2010 | Hsu | A61K 9/1075 514/49 |
| 2010/0297194 | A1 | 11/2010 | Catron et al. | |
| 2012/0003305 | A1* | 1/2012 | Colledge | A61K 9/145 424/452 |
| 2012/0003309 | A1 | 1/2012 | Colledge et al. | |

FOREIGN PATENT DOCUMENTS

| | | | | |
|---|---|---|---|---|
| WO | WO2006076620 | * | 7/2006 | A61K 31/4184 |
| WO | 2010/063476 A2 | | 6/2010 | |
| WO | 2010/063493 A1 | | 6/2010 | |
| WO | 2010/126676 A1 | | 11/2010 | |

OTHER PUBLICATIONS

Dubbelnnan et al. (Abstract: JChromatogr B Analyt Technol Biomed Life Sci. 2012 893-894) 2 pages. (Year: 2012).*
Koo et al. (AAPS PharmSciTech 2011;12(2):746-754)) (Year: 2011).*
Kolliphor ® RH40 [online] retrieved on Apr. 3, 2019 from: https://pharmaceutical.basf.conn/en/Drug-Formulation/Kolliphor-RH40.html; 9 pages. 2019 (Year: 2019).*
Balfour et al., "Bendamustine" Drug, 61, 631-638 (2001).
Katdare et al., "Excipient Development for Pharmaceutical, Biotechnology, and Drug Delivery Systems", First Edition, Chapter 11—Excipients for Oral Liquid Formulations, 155-180 (2006).
Katdare et al., "Excipient Development for Pharmaceutical, Biotechnology, and Drug Delivery Systems", First Edition, Chapter 13—Excipients for Semisolid Formulations, 197-223 (2006).
Pönisch et al., "Treatment of Bendamustine and Prednisone in patients with newly diagnosed multiple myeloma results in superior complete response rate, prolonged time to treatment failure and improved quality of life compared to treatment with Melphalan and Prednisone—a randomized phase III study of the East German Study Group of Hematology and Oncology (OSHO)", J Cancer Res Clin Oncol, 132: 205-212 (2006).
Rummel et al., "Bendamustine Plus Rituximab Is Superior in Respect of Progression Free Survival and CR Rate When Compared to CHOP Plus Rituximab as First-Line Treatment of Patients with Advanced Follicular, Indolent, and Mantle Cell Lymphomas: Final Results of a Randomized Phase III Study of the StiL (Study Group Indolent Lymphomas, Germany)", Blood (ASH Annual Meeting Abstracts), 114: Abstract 405 (2009).
Herold et al., "Bendamustine, vincristine and prednisone (BOP) versus cyclophosphamide, vincristine and prednisone (COP) in advanced indolent non-Hodgkin's lymphoma and mantle cell lymphoma: results of a randomised phase III trial (OSHO# 19)", J Cancer Res Clin Oncol, 132: 105-112 (2006).
Vippagunta et al., "Crystalline solids", Advanced Drug Delivery Reviews, 48: 3-26 (2001).
Braga et al., "Crystal Polymorphism and Multiple Crystal Forms", Struct Bond, 132: 25-50 (2009).
Muller, "Inorganic Structural Chemistry", John Wiley & Sons, 14-15 (1993).
Ribosepharm, "Product Monograph" 3-73 (2005).
International Search Report issued in corresponding International Patent Application No. PCT/EP2011/002763 dated Aug. 3, 2011.
International Preliminary Report on Patentability issued in corresponding International Patent Application No. PCT/EP2011/002763 dated Dec. 4, 2012.
Remington, "The Science and Practice of Pharmacy" 21st Edition (2005).
Ansel et al., "Pharmaceutical Dosage Forms and Drug Delivery System" 8th edition, 231 (2005).
Seiwert, "FIP Guidelines for Dissolution Testing of Solid Oral Products" Pharm. Ind., 57: 362-369 (1995).

* cited by examiner

Flow-sheet of wet granulation manufacturing trials

*Placebo batches were manufactured only for the granulated saccharides with doubtful compression test.

ORAL DOSAGE FORMS OF BENDAMUSTINE AND THERAPEUTIC USE THEREOF

The present invention relates to oral dosage forms comprising bendamustine or a pharmaceutically acceptable ester, salt or solvate thereof and therapeutic use thereof.

BACKGROUND OF THE INVENTION

Bendamustine (4-[5-[bis(2-chloroethyl)amino]-1-methylbenzimidazo-2-yl]butanoic acid, a nitrogen mustard) is an alkylating agent with bifunctional alkylating activity. It corresponds to the following formula (I):

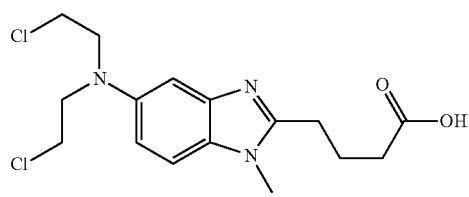

Bendamustine appears to be free of any cross-resistance with other alkylating agents, which offers advantages in terms of chemotherapy for patients who have already received treatment with an alkylating agent.

Bendamustine was initially synthesized in the German Democratic Republic (GDR). The hydrochloric acid of bendamustine was the active ingredient in a commercial product available from 1971 to 1992 under the trade name Cytostasan®. Since that time, it has been marketed in Germany under the trade name Ribomustin® and has been widely used to treat chronic lymphocytic leukemia, non-Hodgkin's lymphoma and multiple myeloma.

The marketed product contains a lyophilized powder of bendamustine hydrochloride which is reconstituted with water for injection yielding a concentrate. This is subsequently diluted with an aqueous solution of 0.9% sodium chloride resulting in the final solution for infusion. This final solution is administered to the patient by intravenous infusion over a period of about 30 to 60 minutes.

Hydrolysis of the bis-2-chloroethylamino-group of bendamustine in water leads to reduction in potency and to impurity formation (B. Maas et al. (1994) in Pharmazie 49: 775-777). Hence administration, usually in a hospital or at least under medical supervision, must occur immediately after reconstitution of the lyophilized powder. Furthermore, reconstitution has been reported to be difficult. It may require more than 30 minutes. Further, it is burdensome and time-consuming for the healthcare professionals responsible for reconstituting the product in the 2 step process.

Preiss et al. (1985) in Pharmazie 40:782-784 compared the pharmacokinetics of bendamustine hydrochloride in plasma in 7 patients after intravenous and oral administration respectively in a dose ranging between 4.2-5.5 mg/kg. The intravenous infusion prepared from the commercially available Cytostasan® product was given over 3 minutes, whereas oral medication in an equivalent dose was taken in the form of capsules, containing 25 mg of bendamustine hydrochloride. The number of capsules to be taken by the patients varied from 10-14, referring to absolute oral doses of 250-350 mg. After oral administration maximal plasma levels were detectable within 1 hour. The mean oral bioavailability was calculated to be 57%, ranging from 25% to 94% indicating a large inter-individual variability (% CV=44%). A similar study with an even larger inter-individual variability (25-121%) was published in a later document by Preiss et al. (Z. Klin. Med. 44(1989): 125-129).

Weber (1991) (Pharmazie 46(8): 589-591) investigated the bioavailability of bendamustine hydrochloride in B6D2F1-mice and found that the absorption of the drug from the gastro-intestinal tract is incomplete resulting in a bioavailability of about 40% only.

US 2006/0128777 A1 describes methods for treating cancers, characterised by death-resistant cells and bendamustine-containing compositions in general. Amongst these compositions are oral dosage forms, which are capsules, tablets, pills, powders or granules, wherein the active compound may be admixed with at least one inert excipient, such as sucrose, lactose or starch. However, specific compositions were not exemplified.

Bendamustine hydrochloride is only sparingly soluble in water at a pH of 2.0 and is slightly or very slightly soluble in a range of organic solvents. A good solubility has been observed however in ethanol and methanol. Therefore it is not surprising that the oral bendamustine compositions, as investigated by Preiss et al. and Weber gave rise to relatively poor bioavailability results and a large inter-individual variability.

In view of the stability problems with the intravenous marketed formulation, once reconstituted with water, and in order to improve the patient compliance there has been a long-felt need for a stable dosage-form comprising bendamustine which is easy to administer to the patient and which provides good bioavailability without large inter- and intraindividual variability. There is also a need for a pharmaceutical composition from which the bendamustine is absorbed completely or at least to a high extend in the stomach, thereby avoiding or reducing the degradation of the bendamustine in the small or large intestine.

SUMMARY OF THE INVENTION

In order to solve the above problems the present inventors have carried out detailed investigations. They finally succeeded in obtaining the stable pharmaceutical compositions according to the invention. These compositions are suitable for oral administration and comprise bendamustine or a pharmaceutically acceptable ester, salt or solvate thereof as an active ingredient, and at least one pharmaceutically acceptable excipient, which compositions apart from having a good stability also have a good dissolution profile in acidic media, a good bioavailability and a therapeutically acceptable inter- and intraindividual variability.

DETAILED DESCRIPTION OF THE INVENTION

Figure 1:
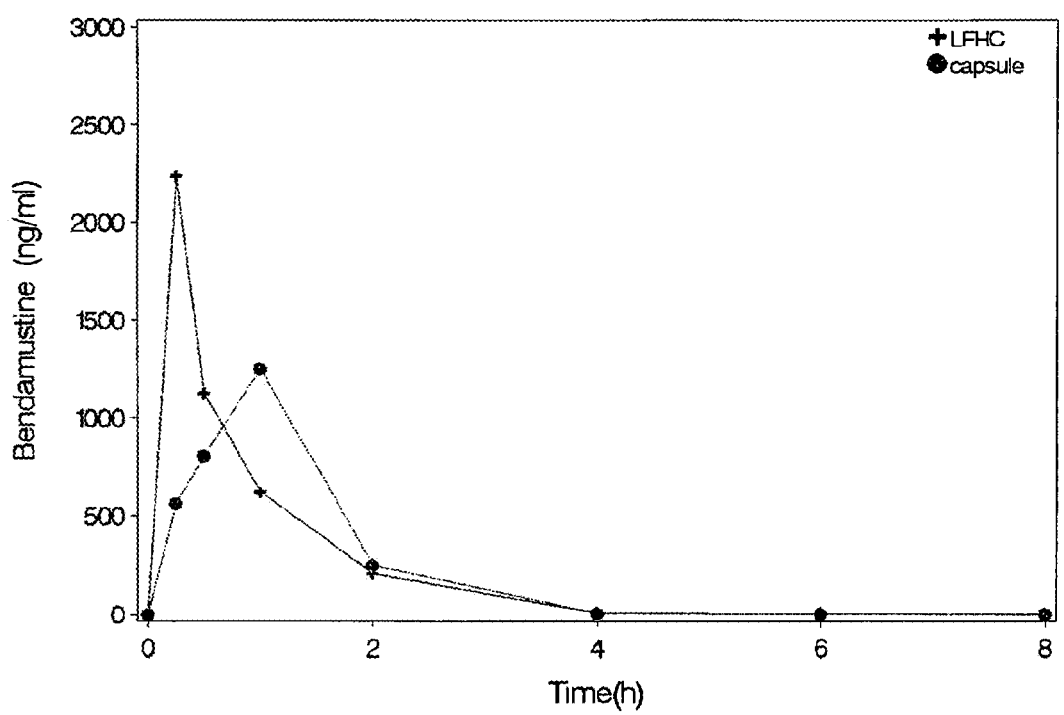
FIG. 1 shows the mean plasma concentration vs. time curve obtained after administering bendamustine hydrochloride in the form of the prior art capsule (reference example 1) and the liquid filled hard capsule formulation of Example 2 to dogs. It is apparent from FIG. 1 that the liquid filled hard capsule formulation provides for a higher maximum concentration of bendamustine, as compared with the prior art reference capsule formulation.

The present invention relates to a pharmaceutical composition for oral administration which comprises bendamustine or a pharmaceutically acceptable, ester, salt or solvate thereof as an active ingredient, and a pharmaceutically acceptable excipient and which shows a dissolution of the bendamustine of at least 60% in 20 minutes, 70% in 40 minutes and 80% in 60 minutes, as measured with a paddle apparatus at 50 rpm according to the European Pharmacopoeia in 500 ml of a dissolution medium at a pH of 1.5, and wherein the pharmaceutically acceptable excipient is either a pharmaceutically acceptable non-ionic surfactant, selected from the group consisting of a polyethoxylated castor oil or derivative thereof and a block copolymer of ethylene oxide and propylene oxide or a pharmaceutically acceptable saccharide selected from the group consisting of one or more of a monosaccharide, a disaccharide, an oligosaccharide, a cyclic oligosaccharide, a polysaccharide and a saccharide alcohol, wherein the ratio by weight of the active ingredient to the saccharide excipient(s) is in the range of 1:1-5.

In a first embodiment the present invention relates to a pharmaceutical composition for oral administration, the composition comprising bendamustine or a pharmaceutically acceptable, ester, salt or solvate thereof as an active ingredient, and a pharmaceutically acceptable excipient, which is a non-ionic surfactant, selected from the group consisting of a polyethoxylated castor oil or derivative thereof and a block copolymer of ethylene oxide and propylene oxide.

An embodiment of the first embodiment of the invention is a pharmaceutical composition, comprising bendamustine or a pharmaceutically acceptable ester, salt or solvate thereof and a pharmaceutically acceptable excipient, which is a non-ionic surfactant, selected from the group consisting of a polyethoxylated castor oil or derivative thereof and a block copolymer of ethylene oxide and propylene oxide, wherein the composition is suitable for oral administration by including it into a hard gelatine capsule.

A further embodiment of the first embodiment of the invention is a pharmaceutical composition for oral administration in a solid dosage-form, which is a hard gelatine capsule, the composition comprising bendamustine or a pharmaceutically acceptable ester, salt or solvate thereof and a pharmaceutically acceptable excipient, selected from the group consisting of a polyethoxylated castor oil or derivative thereof and a block copolymer of ethylene oxide and propylene oxide and preferably selected from the group consisting of macrogol glycerol hydroxystearate, polyoxyl-35-castor oil and ethylene oxide/propylene oxide block copolymer (Pluronic® L44 NF or Poloxamer® 124), wherein the use of the specific non-ionic surfactant leads to a dissolution profile of at least 60% bendamustine dissolved after 20 minutes, 70% dissolved after 40 minutes and 80% dissolved after 60 minutes, as measured with a paddle apparatus at 50 rpm according to the European Pharmacopoeia in 500 ml of a dissolution medium at a pH of 1.5 and preferably it results in a dissolution of at least 60% bendamustine dissolved after 10 minutes, 70% after 20 minutes and 80% after 30 minutes.

A preferred embodiment of the first embodiment is a pharmaceutical composition for oral administration in a solid dosage-form, which is a hard gelatine capsule, the composition comprising bendamustine hydrochloride and a pharmaceutically acceptable excipient, which is macrogol glycerol hydroxystearate, wherein the use of the specific non-ionic surfactant results in a dissolution of at least 60% bendamustine dissolved after 10 minutes, 70% after 20 minutes and 80% after 30 minutes, as measured with a paddle apparatus at 50 rpm according to the European Pharmacopoeia in 500 ml of a dissolution medium at a pH of 1.5.

In a second embodiment the present invention relates to a pharmaceutical composition comprising bendamustine or a pharmaceutically acceptable ester, salt or a solvate thereof as an active ingredient and at least one pharmaceutically acceptable excipient selected from monosaccharides, disaccharides, oligosaccharides, cyclic oligosaccharides, a polysaccharide and saccharide alcohols. Preferably, the ratio by weight between the active ingredient and excipient is in the range of 1 to 1-5, preferably 1 to 2-5, more preferably a ratio selected from 1:5 and 1:2.

In an embodiment of the second embodiment of the invention the present invention relates to a pharmaceutical composition in a solid dosage form for oral administration, the composition comprising bendamustine or a pharmaceutically acceptable ester, salt or solvate thereof as an active ingredient, and at least one pharmaceutically acceptable excipient, which is a pharmaceutically acceptable saccharide selected from the group consisting of one or more of a monosaccharide, a disaccharide, an oligosaccharide, a cyclic oligosaccharide, a polysaccharide and a saccharide alcohol, wherein the ratio by weight of the active ingredient to the excipient is in the range of 1:1.

In a further embodiment of the second embodiment of the present invention relates to a pharmaceutical composition in a solid dosage form suitable for oral administration, the composition comprising bendamustine or pharmaceutically acceptable ester, salts or solvates thereof as an active ingredient and at least one pharmaceutically acceptable excipient which is a pharmaceutically acceptable saccharide selected from the group consisting of one or more of a monosaccharide, a disaccharide, an oligosaccharide, a cyclic oligosaccharide, a polysaccharide and a saccharide alcohol, wherein the ratio by weight of the active ingredient to the saccharide excipient(s) is in the range of 1:2-5 and which composition shows a dissolution of the bendamustine of at least 60% in 20 minutes, 70% in 40 minutes and 80% in 60 minutes as measured with a paddle apparatus at 50 rpm according to the European Pharmacopoeia in 500 ml of a dissolution medium at a pH of 1.5.

Further preferred embodiments within the scope of the above second embodiments are pharmaceutical compositions wherein the pharmaceutically acceptable saccharide is selected from the group consisting of one or more of a monosaccharide, a disaccharide and an oligosaccharide, wherein the ratio by weight of the active ingredient to the saccharide excipient(s) is in the range of 1:2-5 and which composition shows a dissolution of the bendamustine of at least 60% in 20 minutes, 70% in 40 minutes and 80% in 60 minutes as measured with a paddle apparatus at 50 rpm according to the European Pharmacopoeia in 500 ml of a dissolution medium at a pH of 1.5.

The present invention is based on the surprising finding that stable compositions of bendamustine having a specific and desirable dissolution profile can be obtained by incorporating into the pharmaceutical composition certain non-ionic surfactants or certain saccharides or saccharide alcohols. It has been found that if a pharmaceutically acceptable non-ionic surfactant, selected from the group consisting of a polyethoxylated castor oil or derivative thereof and a block copolymer of ethylene oxide and propylene oxide and preferably selected from the group consisting of macrogol glycerol hydroxystearate, polyoxyl-35-castor oil and ethylene oxide/propylene oxide block copolymer (Pluronic® L44 NF or Poloxamer® 124) is used as an excipient in a pharmaceutical composition comprising bendamustine or a pharmaceutically acceptable ester, a salt or a solvate thereof as an active ingredient, a particularly favourable profile of the composition with respect to stability and degradation products, dissolution, bioavailability and a reduced variability in bioavailability is achieved. The incorporation of the above-mentioned non-ionic surfactants in bendamustine-containing compositions results in a dissolution profile of at least 60% bendamustine dissolved after 20 minutes, 70% dissolved after 40 minutes and 80% dissolved after 60 minutes, as measured with a paddle apparatus at 50 rpm according to the European Pharmacopoeia in 500 ml of a dissolution medium at a pH of 1.5 and preferably it results in a dissolution of at least 60% bendamustine dissolved after 10 minutes, 70% after 20 minutes and 80% after 30 minutes.

It has further been found that if a pharmaceutically acceptable saccharide selected from the group consisting of one or more of a monosaccharide, a disaccharide, an oligosaccharide, a cyclic oligosaccharide, a polysaccharide or a saccharide alcohol and preferably selected from the group consisting of one or more of a monosaccharide, a disaccharide and an oligosaccharide is used as an excipient in a pharmaceutical composition comprising bendamustine or pharmaceutically acceptable ester, salt or solvate thereof as an active ingredient, a particularly favourable profile of the composition as regards stability, tabletting properties, dissolution and impurity formation is achieved. The above saccharides result in a composition which shows a dissolution of the bendamustine of at least 60% in 20 minutes, 70% in 40 minutes and 80% in 60 minutes as measured with a paddle apparatus at 50 rpm according to the European Pharmacopoeia in 500 ml of a dissolution medium at a pH of 1.5.

Within the above scope of the second embodiment of the invention, any combination of one or more of a monosaccharide, a disaccharide, an oligosaccharide, a cyclic oligosaccharide, a polysaccharide and a saccharide alcohol may be used.

It has particularly been found that particular saccharides are associated with a particularly favourable profile of a pharmaceutical composition as regards stability and dissolution. Preferred saccharides of the composition according to the second embodiment of the present invention are dextrose anhydrous, dextrose monohydrate, lactitol monohydrate, trehalose, sorbitol, erythritol, maltose monohydrate, mannitol, lactose anhydrous, lactose monohydrate, maltitol, xylitol, sucrose, sucrose 97%+maltodextrin 3%, β-cyclodextrin, D-raffinose pentahydrate, D-melezitose monohydrate and microcrystalline cellulose. The pharmaceutical compositions according to the present invention show good tabletting characteristics, fast dissolution and a pharmaceutically acceptable stability.

The above saccharides constitute preferred embodiments of the second embodiment of the present invention and any combination thereof may be used. Preferably, the ratio between the active ingredient and the above saccharides is in the range of 1:1-5, preferably 1:2-5 and more preferably a ratio selected from 1:5 and 1:2.

A further preferred embodiment of the second embodiment of the invention is a pharmaceutical composition in a solid dosage form for oral administration, the composition comprising bendamustine or a pharmaceutically acceptable ester, salt or solvate thereof as an active ingredient and at least one pharmaceutically acceptable excipient selected from dextrose anhydrous, dextrose monohydrate, lactitol monohydrate, trehalose, sorbitol, erythritol, maltose monohydrate, mannitol, lactose anhydrous, lactose monohydrate, maltitol, xylitol, sucrose, sucrose 97%+maltodextrin 3%, β-cyclodextrin, D-raffinose pentahydrate, D-melezitose monohydrate and microcrystalline cellulose and which composition shows a dissolution of the bendamustine of at least 60% in 10 minutes, 70% in 20 minutes and 80% in 30 minutes.

Particularly preferred saccharides are mannitol, maltitol, erythritol, xylitol, lactose, sucrose, glucose, sorbitol, maltose, trehalose, lactitol and dextrose (anhydrous or monohydrate) and the weight ratio of the active ingredient to said saccharide is preferably in the range of 1:2-5. Combinations of two or more saccharides within the scope of the above saccharides are also included within the present invention.

A person skilled in the art is well in a position to select suitable combinations within the saccharide excipients mentioned above and obtain a composition which shows a dissolution of bendamustine of at least 60% in 20 minutes, 70% in 40 minutes and 80% in 60 minutes as measured with a paddle apparatus at 50 rpm according to the European Pharmacopoeia in 500 ml of a dissolution medium at a pH of 1.5.

In a preferred embodiment the composition is in the form of a tablet, a granulate, or a pill.

A preferred dosage form is a tablet, preferably an immediate release tablet, which means that the tablet releases the active ingredient very fast after being placed in an aqueous medium, preferably an acidic medium. The term tablet also comprises fast-disintegrating tablets, amongst which are dispersible tablets and effervescent tablets.

The most commonly used methods of tablet preparation are direct compression, dry granulation and wet granulation. Direct compression involves compressing a mixture containing the active ingredient(s) and the excipient(s) on a tablet press (L. Lachman et al., in: The Theory and Practice of Industrial Pharmacy, 3rd ed., 1986). The mixture to be compressed must possess both good flow and compression properties in order to produce tablets having a uniform content of the active ingredient(s). Good flow properties cannot always be achieved by adding appropriate excipients, such as lubricants, anti-adhesive agents and flow-promoters to the mixture. Hence frequently the mixture is granulated prior to compression.

Granulation is a process by which sphere-like or regularly shaped aggregates called granules are formed out of the powder mixture. This can be achieved by dry granulation methods and wet granulation methods. Granulation is also used for converting a mixture of powders with poor cohesion into aggregates, which when compressed result in tablets that have good cohesion properties.

In the case of fast-disintegrating tablets, the active ingredient(s), optionally in admixture with one or more excipients, is (are) advantageously provided with a coating in order to mask the taste of such ingredient(s) and/or to protect the same against possible harmful effects by light and/or moisture and in the case of bendamustine to protect the mucosa in the mouth against the harmful effects exerted by the active compound. For that purpose a granulate preferably is prepared and processed as further outlined below.

The expression "granulate" refers to aggregates of particles, sometimes called granules. A granulate in general is prepared by compaction and/or compression techniques (dry granulation) or by wet granulation techniques, using a liquid in which optionally a wet granulation binding agent is dissolved (Remington's Pharmaceutical Sciences 18th ed. 1990, page 1641). Wet granulation techniques also include extrusion techniques. Accordingly the term granulate also comprises pellets, spherules, and extrudates, of which pellets preferably are used as examples of a granulate.

A pellet may be described as a small particle of approximately 1.0-1.6 mm in diameter and having a certain density, which particle is prepared by application of the pharmaceutical processes of extrusion and spheronisation to powder mixtures.

The active ingredient(s), optionally in admixture with one or more excipients, may be advantageously provided with a coating in order to mask the taste of such ingredient and/or to protect the same against possible harmful effects by light and/or moisture and/or to protect the mucosa in the mouth against the harmful effects exerted by the active compound.

Pills are small, round solid dosage forms, prepared by adding the active ingredient to a doughy mixture of triglycerides. The mixture is rolled into a long string, which is then cut into pieces and rolled (J. T. Carstensen: Pharmaceutical principles of solid dosage forms, 1993, Technomic Publishing Company, Inc. page 63).

Preferably the dosage forms according to the invention are prepared by dry compaction techniques. Suitable techniques are for example described in Remington's Pharmaceutical Science 18th. ed. 1990, page 1644. They comprise dry granulation, roller compaction and direct compression. When tablets are prepared by these techniques, it is even more advantageous to use direct compression.

The dosage forms according to the present invention are preferably provided with a coating. The coating has different purposes: it may serve for masking the taste of the active ingredient(s) used in the composition, whilst at the same time it is protecting the active ingredient against possible harmful effects by light and/or moisture such as oxidation, degradation, etc. Furthermore, the coating layer may prevent the subject from damage of the oral mucosa by the active ingredient.

The coating layer can be applied to the dosage forms by techniques well-known in the art such as spray-coating and microencapsulation. For tablets it can be in the form of a film-coating, a saccharide-coating or a compression coating. Preferably a film-coating process is used (Remington's Pharmaceutical Sciences 18th ed. 1990, page 1666). In case an active ingredient requires the application of a coating for fast-disintegrating tablets the individual granules can suitably be provided with a coating prior to compression into tablets.

The expression "pharmaceutically acceptable ester thereof" describes any pharmaceutically acceptable ester of bendamustine, such as esters with alkyl alcohols and sugar alcohols. Examples of the alkyl alcohols are $C_{1-6}$-alkyl alcohols such as methanol, ethanol, propanol, isopropanol, butanol and tert-butanol. Examples of the sugar alcohols are mannitol, maltitol, sorbitol, erythritol, glycol, glycerol, arabitol, xylitol and lactitol. Preferred examples of the bendamustine esters are the ethyl ester, the isopropyl ester, the mannitol ester and the sorbitol ester, most preferred is the ethylester thereof.

The expression "pharmaceutically acceptable salt thereof" describes any pharmaceutically acceptable salt of bendamustine that administered to a patient (directly or indirectly) provides bendamustine. This term further comprises the pharmaceutically acceptable salt of a bendamustine ester. Nevertheless, it will be considered that the pharmaceutically non-acceptable salts also are included within the limits of this invention since these compounds can be useful in the preparation of pharmaceutically acceptable salts. For example, pharmaceutically acceptable salts of bendamustine are synthesized from the corresponding compound that contains an acid or basic group, by conventional chemical methods. Generally, these salts are, for example, prepared by means of the reaction of free acidic or basic forms of these compounds in a stoichiometric amount with a corresponding base or acid in water or an organic solvent or a mixture of both. Nonaqueous media like ether, ethyl acetate, isopropanol or acetonitrile are generally preferred. Examples of acids which may be used for the salt formation of pharmaceutically acceptable salts of bendamustine include inorganic acids such as hydrochloride, hydrobromide, hydriodide, sulphuric, nitric, and phosphoric acids, and organic acids such as acetic, maleic, fumaric, citric, oxalic, succinic, tartaric, malic, lactic, methylsulphonic and p-toluenesulphonic acids. Pharmaceutically acceptable salts of bendamustine may be derived from either inorganic or organic bases to yield ammonium salts; alkali metal salts (lithium, sodium, potassium, etc.), alkaline earth salts like calcium or magnesium, aluminium salts, lower alkylamine salts like methylamine or ethylamine salts, lower alkyldiamine salts like ethylenediamine salts, ethanolamine, N,N-dialkyleneethanolamine, triethanolamine, and glucamine salts, as well as basic salts of amino acids. Especially preferred are acid salts prepared from the hydrochloride, the hydrobromide, and the hydroiodide, whereas the hydrochloride salt is the most preferred pharmaceutically acceptable salt of bendamustine. The pharmaceutically acceptable salts are produced by conventional techniques well-known in the art.

The expression "pharmaceutically acceptable solvate thereof" describes any pharmaceutically acceptable solvate that, administered to a patient (directly or indirectly) provides bendamustine. This term further comprises the pharmaceutically acceptable solvate of a bendamustine ester. Preferably, the solvate is a hydrate, a solvate with an alcohol such as methanol, ethanol, propanol, or isopropanol, a solvate with an ester such as ethyl acetate, a solvate with an ether such as methyl ether, ethyl ether or THF (tetrahydrofuran) or a solvate with DMF (dimethylformamide), of which a hydrate or a solvate with an alcohol such as ethanol is more preferred. A solvent for constituting the solvate is preferably a pharmaceutically acceptable solvent.

It is especially preferred that the active ingredient in the invention's compositions is bendamustine or a pharmaceutically acceptable salt thereof. It is most preferred that the active ingredient is bendamustine hydrochloride.

The dose of the active ingredient in the pharmaceutical composition may readily be determined by the skilled artisan depending on the patient's condition, sex, body weight, body surface area ($m^2$; average approximately 2 $m^2$ per person), or age, especially depending on the patient's body weight and body surface area. It is preferred that the daily dosage ranges from about 50 to about 1000 mg, preferably from about 100 to about 500 mg of the active ingredient, more preferably from about 200 to about 400 mg and most preferably about 280 mg. The daily dosage may be taken as a single dose or as multiple doses such as twice or three-times daily, most preferably as a single daily dose. The daily dose may be taken once a week or several times a week. The minimum oral single dose is 50 mg. The above doses relate to bendamustine and may easily be recalculated in relation to a pharmaceutically acceptable ester, salt or solvate thereof. The dose can be expressed in absolute amounts (mg), but in oncology normally the dose is expressed in mg/m$^2$, taking into account the patient's body surface area.

The maximum tolerated dose (MTD) and the effective dose of bendamustine is dependent on the cumulative amount given per cycle. Based on the reproducible BA of bendamustine the MTD is reached at a cumulative dose of 1000 mg per cycle. The lower limit of effective cumulative dose is between 350 mg and 500 mg per cycle. Therefore a cumulative dose per cycle of 350 mg to 1000 mg needs to be given orally. The preferred cumulative oral dose per cycle is 500 mg to 700 mg. Bendamustine can be given in effective single doses from 50 mg to 900 mg. The preferred range of a single oral dose is 200-300 mg.

The maximum tolerated dose (cumulative) is about 1000 mg bendamustine within one cycle (3-4 week cycle). In sensitive/compromised patients the cumulative dose is about 350-500 mg bendamustine within one cycle (3-4 weeks), preferably about 365 mg within 4 weeks.

Possible and preferred oral dosage regimens are:
200-300 mg bendamustine on day 1 and day 2, optionally followed by a maintenance low dose of 50 mg once a day
50 mg bendamustine each day from day 1 up till and including day 14
about 150 mg bendamustine once a week for 3 weeks.

Generally, the treatment with bendamustine is effected in therapeutic cycles, wherein bendamustine and optional additional agents are dosed for 1 to 5 days and then the treatment is repeated after an interruption of 2 to 4 weeks. The repetitions of the therapeutic cycle are continued until the respective condition to be treated has improved. Basically, the number of repetitions is within the discretion of a medical doctor. Generally, the therapeutic cycle is repeated 4 to 15 times, preferably 4 to 12 times, more preferably 4 to 6 times.

In the following approved (intravenous application) and preferred oral dosage regimens for specific indications within the scope of the present invention are given:

Monotherapy for chronic lymphocytic leukaemia:
100 mg/m$^2$ body surface area bendamustine hydrochloride on days 1 and 2; every 4 weeks (intravenous application).
Oral: 145 mg/m$^2$ or 261 mg (1.8 m$^2$): range 100-200 mg/m$^2$ or 150-350 mg per day.

Monotherapy for indolent non-Hodgkin's lymphomas refractory to rituximab:
120 mg/m$^2$ body surface area bendamustine hydrochloride on days 1 and 2; every 3 weeks (intravenous application).
Oral: 174 mg/m$^2$ or 313 mg (1.8 m$^2$): range 100-250 mg/m$^2$ or 150-400 mg per day.

Preferably bendamustine is combined with vincristine and prednisone in first line non-Hodgkin's lymphoma.

Multiple myeloma:
120-150 mg/m$^2$ body surface area bendamustine hydrochloride on days 1 and 2 (intravenous application), 60 mg/m$^2$ body surface area prednisone i.v. or per os on days 1 to 4; every 4 weeks.
Oral: 174-217 mg/m$^2$ or 313-391 mg (1.8 m$^2$): range 100-250 mg/m$^2$ or 150-400 mg per day.

Combination treatment for first-line therapy for patients with follicular (FL), indolent and mantle cell lymphomas (MCL):
Rituximab 375 mg/m$^2$ (day 1) plus either bendamustine 90 mg/m$^2$ (days 1+2) every 28 days (intravenous application).
Oral: 130 mg/m$^2$ or 235 mg (1.8 m$^2$): range 100-200 mg/m$^2$ or 150-350 mg per day.

The invention thus relates to a pharmaceutical composition as defined above for use for the oral treatment of a medical condition which is selected from chronic lymphocytic leukaemia, acute lymphocytic leukaemia, chronic myelocytic leukaemia, acute myelocytic leukaemia, Hodgekin's disease, non-Hodgkin's lymphoma, multiple lymphoma, breast cancer, ovarian cancer, small cell lung cancer and non-small cell lung cancer, wherein the dosage regimen comprises at least the administration of a dose of 100 to 600 mg/m$^2$/per person of bendamustine on day 1 and day 2, optionally a dose of 50 to 150 mg/m$^2$ i.v. or orally of a corticosteroid on days 1 to 5, and optionally a suitable dose of a further active agent selected from the group consisting of an antibody specific for CD20, an anthracyclin derivative, a vinca alkaloid or a platin derivative; and the repetition of said dosage regimen 4 to 15 times after intervals of two to four weeks. Moreover, the invention relates to the pharmaceutical composition as defined above for the use as defined above, wherein the active ingredient bendamustine is administered in a dosage regimen selected from 200-300 mg on day 1 and day 2, optionally followed by a maintenance dose of 50 mg once a day, 50 mg each day from day 1 up till and including day 14, or 150 mg once a week for 3 weeks.

The invention further relates to the pharmaceutical composition as defined above for the use as defined above, wherein the patient is one having non-Hodgkin's lymphoma and the dosage regimen comprises administering a total amount of 200 mg/person/day of active ingredient bendamustine on days 1 to 5, 2 mg i.v. of vincristine on day 1 and 100 mg/m$^2$ i.v. of prednisone on days 1 to 5 and repeating said treatment every three weeks until the non-Hodgkin's lymphoma has improved.

The invention further relates to the pharmaceutical composition as defined above for the use as defined above wherein the patient is one having multiple myeloma and the dosage regimen comprises administering an amount of 100-250, preferably 174 to 217 mg/m$^2$ body surface area bendamustine hydrochloride on days 1 and 2, 60 mg/m$^2$ i.v. or orally of prednisone on days 1 to 4 and repeating said treatment every four weeks until the multiple myeloma has improved.

The invention further relates to the pharmaceutical composition as defined above for the use as defined above, wherein the patient is one having chronic lymphocytic leukaemia and the dosage regimen comprises administering an amount of 100 to 200, preferably 145 mg/m$^2$ body surface area bendamustine hydrochloride on days 1 and 2 and 60 mg/m$^2$ i.v. or orally of prednisone on days 1 to 4 and repeating said treatment every four weeks until the chronic lymphocytic leukaemia has improved.

The invention moreover relates to the pharmaceutical composition as defined above for the use as defined above, wherein the patient is one having follicular, indolent or mantle cell lymphoma and the dosage regimen comprises administering a dose of 375 mg/m$^2$ rituximab on day 1 plus 100 to 200, preferably 130 mg/m$^2$ oral bendamustine on days 1 and 2 every 28 days until the respective lymphoma has improved.

The dosage form may contain the amount of a single daily dose or parts thereof. It is preferred that the dosage form of the present invention comprises about 10 to about 1000 mg, preferably about 25 to about 600 mg, more preferably about 50 to about 200 mg and most preferably about 50 mg or about 100 mg of the active ingredient.

As used herein, the term "non-ionic surfactant" refers to an amphiphilic compound having a polar, hydrophilic group and a non-polar, lipophilic group or chain and wherein the hydrophilic and lipophylic properties of the compound are characterised by the so-called Hydrophilic-Lipophilic Balance (HLB) value. The non-ionic surfactant to be used for preparing the compositions of the present invention preferably has an HLB-value between 10 and 20 and preferably between 12 and 18. The non-ionic surfactant further has a melting point, pour point or melting range between 5° C. and body temperature (37° C.) and preferably between just below room temperature (20° C.) and body temperature. The material can be in a liquid or a semi-solid state at room temperature. The amphiphilic material is a carrier for the bendamustine active ingredient, which can be present in a dissolved form, a suspended form or partly in a dissolved and partly in a suspended form.

The non-ionic surfactants that are advantageously used for the preparation of the compositions according to the first embodiment of the present invention are selected from the group consisting of a polyethoxylated castor oil or derivative thereof and a block copolymer of ethylene oxide/propylene oxide, provided the materials have the afore-mentioned HLB-value and melting point, pour point or melting range.

In one embodiment, the non-ionic surfactant is a polyethoxylated castor oil. One example of a polyethoxylated castor oil is sold under the tradename Cremophor®. Cremophor® products of various purifies and viscosities are produced and may be used in the present invention. In particular macrogol glycerol hydroxystearate (Cremophor® RH 40) and polyoxyl-35-castor oil (Cremophor® EL or Cremophor® ELP) can be used. Cremophor® ELP and Cremophor® EL are known as nonionic solubilizers and emulsifiers, produced by reacting castor oil with ethylene oxide in a molar ratio of 1 to 35. They have an HLB-value of 12-14 and a melting point of 26° C. Depending on the ambient temperature these products can be characterised as either semi-solid or as a medium viscosity liquid. Macrogol glycerol hydroxystearate (commercially available as Cremophor® RH 40) is a semi-solid material at 25° C., having a viscosity range at the same temperature of 20-40 cps (as a 30% aqueous solution). It is known as a nonionic solubiliser and emulsifier. It is produced by reacting castor oil with ethylene oxide in a molar ratio of 1 to 45. Its HLB-value ranges from 14-16 and the melting range is from 20-28° C. In experiments it was shown that macrogol glycerol hydroxystearate can advantageously be used on its own for the preparation of compositions according to the present invention.

Pluronic® block copolymers consist of ethylene oxide and propylene oxide blocks. The ethylene oxide units have a hydrophilic character whereas the propylene oxide units have a lipophilic character Variations in the number of hydrophilic ethylene oxide units and lipophilic propylene oxide units results in copolymers with a different molecular mass and different hydrophilic-lipophilic-balance (HLB). Examples of block copolymers of propylene oxide ("PEO")-polypropylene oxide ("PPO") meeting the requirements of the HLB-value and the melting point or pour point or melting range for making the compositions according to the present invention include the commercially available types Pluronic® L35, Pluronic® L 44, Pluronic® L64, Pluronic® P85 and Pluronic® P105. Pluronic® L44 or Poloxamer® 124, but not Pluronic® 68 or Poloxamer® 188 and Pluronic® 127 or Poloxamer® 407. Pluronic® L44 is a preferred non-ionic surfactant.

Except for macrogol glycerol hydroxystearate the above-mentioned non-ionic surfactants are all liquids having a viscosity value which may be too low to avoid sedimentation of the bendamustine hydrochloride. The additional problem to be solved was to find an excipient or a combination of excipients that would allow for a total value for the viscosity of the mixture that would be high enough to avoid segregation of the bendamustine chloride when added to the mixture.

Therefore the compositions according to the first embodiment of the present invention, that contain a liquid non-ionic surfactant, advantageously further contain a viscosity improving agent. Suitable viscosity-improving agents include a powder such as colloidal silicon dioxide (commercially available under the trademark Aerosil®) or a semi-solidwaxy material, such as lauroyl macrogol glycerides (commercially available under the trademark Gelucire® 44/14). The amount of the powder or the semi-solid material to be added to the liquid non-ionic surfactant depends on the viscosity of the liquid non-ionic surfactant. Different concentrations have been tested in order to find the minimum suitable amount of viscosity improving agent to be added to visually avoid sedimentation of the active ingredient. Typical relative concentrations of colloidal silicon dioxide to be added range from about 1% to about 8%, but are preferably as low as 1.7% or 2.0% in order not to have a negative impact on the dissolution characteristics of the active ingredient. Typical relative concentrations of lauroyl macrogol glycerides range from 5 to 50%, and are preferably about 10% and about 45%.

Preferred compositions according to the first embodiment of the present invention, are disclosed in example 4 and comprise bendamustine hydrochloride in combination with:
  macrogol glycerol hydroxystearate;
  ethylene oxide/propylene oxide block copolymer (Pluronic® L44 NF or Poloxamer® 124), optionally in combination with colloidal silicon dioxide or lauroyl macrogol glycerides (Gelucire® 44/14) and
  polyoxyl-35-castor oil, optionally in combination with lauroyl macrogol glycerides (Gelucire® 44/14).

The pharmaceutical compositions according to the first embodiment of the present invention are advantageously filled into a capsule, which can then easily be taken by the patient.

Two types of capsule are commonly used and are classified according to the nature and flexibility of the capsule shell: soft and hard capsules.

Soft capsules are single unit solid dosage forms comprising a liquid or semi-solid fill. They are formed, filled and sealed in one operation using a rotary die process. They have been used as unit dose containers for liquids for many years, whereas hard capsules have conventionally been used for the delivery of solids in the form of powders, granulates and pellets. Hard capsules are single unit dosage forms, consisting of a cap and a body, which are manufactured separately and which are supplied empty for filling.

Soft capsules are most commonly manufactured from gelatine, to which a plasticiser, usually glycerine or sorbitol, is added in addition to water. Also for hard capsules the most commonly used polymer is gelatine. An additional component is water, which acts as a plasticiser. This component however may be responsible for degradation of active ingredients, such as bendamustine hydrochloride. Therefore as an alternative hard capsules may be manufactured from hydroxypropylmethyl cellulose.

Both soft and hard capsules in addition can include colouring agents and opacifiers.

The preferred type of capsule for the compositions according to the present invention is the hard capsule and more in particular the hard gelatine capsule.

Ideally, the materials to be filled into the capsule are fluid at room temperature, which would avoid heating during the filling operation. Generally, heating could result in an easy degradation of the active component.

In principle numerous excipients are available for filling into hard capsules, but in addition to biopharmaceutical considerations, the chemical and physical stability of the final dosage-form are also important to consider, as well as the dissolution profile to produce a safe, effective and stable dosage-form.

Generally, fill formulations for hard capsules may be Newtonian liquids, such as oils, thixotropic or shear thinning gels or semi-solid matrix products that are filled at elevated temperatures and in which the active ingredient is either dissolved or suspended as a fine dispersion. In principle any excipient or mixture of excipients can be used provided that the viscosity of the fill material confirms to the requirements of the filling process. The uniformity of capsule fill weights is important. Further fill formulations should not show stringing and should allow for a clean break from the dosing nozzle.

It has surprisingly been found that the compositions according to the first embodiment of the present invention can be advantageously administered in hard gelatine capsules. The particular non-ionic surfactants, selected from the group consisting of a polyethoxylated castor oil or derivative thereof and a block copolymer of ethylene oxide/propylene oxide, and in particular from the group consisting of macrogol glycerol hydroxystearate, polyoxyl-35-castor oil and Pluronic® L44 or Poloxamer® 124, if incorporating bendamustine or a pharmaceutically acceptable ester, salt, or solvate thereof, and after incorporation into hard gelatine capsules result in achieving a good stability, a good dissolution profile and a good bioavailability. To the contrary, if macrogol glycerol hydroxystearate is used in combination with a liquid material, such as bis-diglyceryl polyacyladipate-1 (commercially available as Softisan® 645) and ethylene oxide/propylene oxide block copolymer (commercially available under the names Pluronic® L44 NF or Poloxamer 124), the dissolution profile of bendamustine is deteriorated as compared to compositions containing macrogol glycerol hydroxystearate only. Further it is to be noted that Cremophor® A 25 (ceteareth-25 or macrogol (25) cetostearyl ether) and Cremophor® A 6 (ceteareth-6 and stearylalcohol or macrogol (6) cetostearyl ether) cannot be used as the non-ionic surfactant. Also other commonly used excipients for the preparation of liquid filled capsule preparations were shown to provide no satisfactory results.

Further, the compositions of the present invention can include additional excipients, in particular protective agents, such as anti-oxidants and antimicrobial preservatives, e.g. methyl-, ethyl- and propylparaben, as illustrated in examples 1-3. The antioxidant may be d-alpha tocopherol acetate, dl-alpha tocopherol, ascorbyl palmitate, butylated hydroxyanidole, ascorbic acid, butylated hydroxyanisole, butylatedhydroxyquinone, butylhydroxyanisol, hydroxycoumarin, butylated hydroxytoluene, ethyl gallate, propyl gallate, octyl gallate, lauryl gallate, or mixtures thereof. The anti-oxidant is preferably added to compositions containing macrogol glycerol hydroxystearate or polyoxyl-35-castor oil.

The saccharides are present in the compositions according to the second embodiment of the invention in a substantial amount, preferably in an amount ranging from 2 to 5 times the weight of the active substance. The saccharides when incorporated into the compositions of the present invention, have shown to have a positive effect on the stability of the active compound. In addition to that it was surprisingly found that these excipients result in an increased bioavailability of the active compound, in particular bendamustine hydrochloride, when compared to the reference capsule.

Preferred examples of the saccharides include mannitol, maltitol, erythritol, xylitol, lactose, sucrose, glucose, sorbitol, maltose, trehalose, lactitol and dextrose (anhydrous or monohydrate).

In addition to these saccharide excipients the pharmaceutical composition according to the present invention may comprise further excipients as described in more detail below for lubricants, glidants, fillers (or diluents), binders and disintegrants.

Lubricants are substances which may have one or more of the following functions in pharmaceutical compositions and especially in tablet manufacture: preventing adhesion of the tablet material to the surface of parts of the tabletting machine (hopper, dies and punches), reducing interparticle friction, facilitating ejection of the tablets from the dies and improving the flow rate of the mixture (to be tabletted). Said lubricant is typically selected from a group consisting of stearic acid, salts or esters of stearic acid, hydrogenated vegetable oils, magnesium oxide, polyethylene glycol, sodium lauryl sulphate and talc, and mixtures thereof. Preferably said lubricant is selected from magnesium stearate, calcium stearate, zinc stearate, glyceryl palmitostearate and sodium stearyl fumarate, and mixtures thereof. Stearic acid is the most preferred alternative.

The term glidant in this application is to be understood as a substance which improves the flow characteristics of the mixture to be tabletted. With respect to glidants, any suitable glidant such as talc, silicon dioxide and silicagel (Cab-O-Sil®, Syloid®, Aerosil®), starch and calcium silicate may be used. Typically, silicon dioxide is used.

Generally, the terms filler (or diluent) represent excipients which are used to increase the bulk of the materials to be tabletted. This increase in size improves the handling of the solid compositions. Fillers are usually necessary if the dose of drug per solid composition is low and the solid composition would otherwise be too small. Examples of suitable fillers are lactose, sucrose, mannitol, sorbitol, saccharose, starch, pregelatinized starch, microcrystalline cellulose, powdered cellulose, calcium hydrogen phosphate, calcium carbonate and any combinations thereof. In a preferred embodiment the filler is selected from the group consisting of lactose, starch, microcrystalline cellulose, microfine cellulose and any combinations thereof, most preferably anhydrous lactose and microcrystalline cellulose.

Generally, the term binder is used for agents that impart cohesiveness to the pharmaceutical formulation, which cohesiveness ensures that the composition remains intact especially in case of tablets after compression. Dependent on the compaction technique used (direct compression, dry granulation or wet granulation) different binders are used. For dry compaction techniques (direct compression and dry granulation) suitable binders are lactose, sucrose, mannitol, sorbitol, saccharose, starch, pregelatinized starch, microcrystalline cellulose, powdered cellulose, calcium hydrogen phosphate, calcium carbonate and any combinations thereof. In a preferred embodiment the binder is selected from the group consisting of lactose, starch, microcrystalline cellulose, microfine cellulose and any combinations thereof, most preferably anhydrous lactose and microcrystalline cellulose. In wet granulation processes binders can be used both as a solution and in a dry form. As suitable binders, there may be mentioned, for example, polyvinylpyrrolidone, dispersible cellulose, hydroxypropyl cellulose, hydroxypropylmethyl cellulose, methylcellulose, starch, pregelatinized starch, partly pregelatinized starch, gum arabic, dextrin, pullulan and the like. Among these binders, dispersible cellulose, polyvinylpyrrolidone, hydroxypropyl cellulose and hydroxypropylmethyl cellulose are more preferred.

A disintegrant can be included in a pharmaceutical composition and especially a tablet composition to facilitate its breakup or disintegration after the tablet comes into contact with a physiological aqueous liquid. When the tablet is swallowed, the disintegrant often is responsible for the quick disintegration of the tablet when it comes into contact with body fluids, such as saliva, gastric and intestinal fluids. Materials serving as disintegrants have been classified chemically as starches, celluloses, cross-linked polymers, etc. As a result of investigations concerning the disintegrator species to be used in the practice of this invention and the level of addition thereof, it was found that starch, a modified starch such as sodium starch glycolate (Primojel®), sodium carboxymethyl cellulose, crosslinked carboxymethylcellulose sodium (Ac-Di-Sol®), cross-linked polyvinylpyrrolidone, polacrilin potassium (Amberlite® IRP88) and low-substituted hydroxypropyl cellulose can produce a very good disintegrating effect.

The stability of an aqueous solution of bendamustine is strongly influenced by the pH. A significant hydrolytic decomposition of this compound is observed at pH values higher than about 5. At pH>5, the decomposition proceeds rapidly and the resulting content of by-products is high in this pH range. The main hydrolysis products are 4-[5-[(2-Chloroethyl)-(2-hydroxy-ethyl)amino]-1-methyl-benzimidazo-2-yl]-butanoic acid (HP1), 4-[5-[Bis(2-hydroxyethyl)amino]-1-methyl-benzimidazo-2-yl]-butanoic acid (HP2) and 4-(5-Morpholino-1-methylbenzimidazol-2-yl)-butanoic acid (HP3):

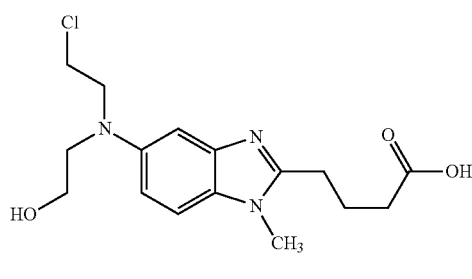

HP1

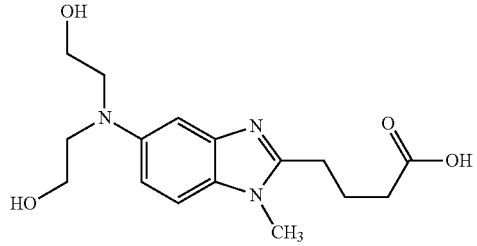

HP2

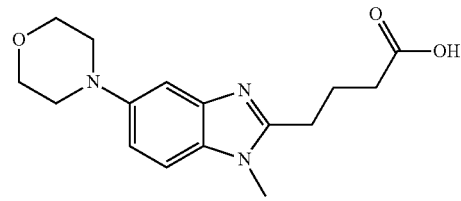

HP3

Absorption of an orally administered drug usually happens from the stomach, the small intestine and/or the large intestine. The pH in the stomach is about 1 to 3.5, in the small intestine about 6.5 to 7.6, and in the large intestine about 7.5 to 8.0. Accordingly, for a compound like bendamustine which is prone to degradation in aqueous environments with a pH higher than 5, it is highly preferable that it is absorbed in the stomach, and does not pass through to the small or even the large intestine, in order to avoid decomposition. Hence there is a need for a pharmaceutical composition from which the bendamustine is absorbed completely or at least to a high extent in the stomach, thereby avoiding or reducing the degradation of the bendamustine in the small or large intestine.

It has surprisingly been found that it is possible to solve this problem by using the present pharmaceutical compositions. These compositions comprising bendamustine hydrochloride in a pharmaceutically acceptable excipient, which is a non-ionic surfactant, selected from the group consisting of a polyethoxylated castor oil or derivative thereof and a block copolymer of ethylene oxide and propylene oxide, or one of the above saccharides surprisingly show a fast dissolution, and in particular a dissolution of the bendamustine of at least 60% in 20 minutes, 70% in 40 minutes and 80% in 60 minutes, and preferably of at least 60% in 10 minutes, 70% in 20 minutes and 80% in 30 minutes, as measured with a paddle apparatus at 50 rpm according to the European Pharmacopoeia in an artificial gastric fluid. The artificial gastric fluid as used herein refers to a solution prepared by dissolving 2 g of sodium chloride in 1000 ml of water and then adjusting the pH to 1.5±0.05 with 5 N hydrochloric acid.

Further they have shown to be stable, when put in accelerated stability testing. This is surprising since it has been shown that:
  in a reference capsule formulation (see reference example 1) containing bendamustine hydrochloride only in a hard gelatine capsule, when stored at 40° C./75% RH (glass vial open) and 50° C., degradation products were formed within one month of storage. In the case of open vials with 40° C. and 75% RH (relative humidity) the amount of hydrolysis product HP1 was increased by a factor of 4 after one month of storage. For the closed vials the HP1 content is even higher;
  in the capsule formulations of reference examples 2, 3 and 4, when stored at 40° C./75% RH (closed glass vial), degradation products were formed within one month of storage and increased upon further storage.

The total time of a drug to pass the stomach to the small intestine is between about 20 minutes to 5 hours, usually between about 30 minutes to 3 hours. Thus pharmaceutical compositions according to this invention advantageously should reduce the degradation of bendamustine in the patient since the bendamustine is released and dissolved to a major extent while in the stomach. Thus even an improved bioavailability of the bendamustine containing compositions according to the invention may be expected.

In a further aspect of this invention the oral pharmaceutical compositions may be used for the treatment or prevention of relapse of a medical condition in a human or animal, preferably a human, which medical condition is selected from chronic lymphocytic leukemia (abbreviated as CLL), acute lymphocytic leukaemia (abbreviated as ALL), chronic myelocytic leukaemia (abbreviated as CML), acute myelocytic leukaemiam (abbreviated as AML), Hodgkin's disease, non-Hodgkin's lymphoma (abbreviated as NHL), multiple myeloma, breast cancer, ovarian cancer, small cell lung cancer, non-small cell lung cancer, and an autoimmune disease.

In a further aspect of this invention the pharmaceutical compositions in a solid dosage form may be used for the treatment, induction, salvage therapy, conditioning prior to stem cell transplantation, maintenance therapy, treatment of residual disease of a medical condition in a human or animal, preferably a human, which medical condition is selected from chronic lymphocytic leukemia (CLL), acute lymphocytic leukaemia (ALL), chronic myelocytic leukaemia (CML), acute myelocytic leukaemia (AML), Hodgkin's disease, non-Hodgkin's lymphoma (NHL), multiple myeloma, breast cancer, ovarian cancer, small cell lung cancer, non-small cell lung cancer, and an autoimmune disease.

The present invention also comprises a method of treatment or prevention of relapse of a medical condition selected from chronic lymphocytic leukemia, acute lymphocytic leukaemia, chronic myelocytic leukaemia acute myelocytic leukaemia, Hodgkin's disease, non-Hodgkin's lymphoma, multiple myeloma, breast cancer, ovarian cancer, small cell lung cancer, non-small cell lung cancer, and an autoimmune disease, in a human or animal body comprising administering to the human or animal body in need thereof an effective amount of the pharmaceutical preparation of this invention. Preferably the medical condition is non-Hodgkin's lymphoma.

In another aspect the of this invention the pharmaceutical composition may be administered in combination with at least one further active agent, wherein said further active agent is given prior, concurrently, or subsequently to the administration of the pharmaceutical composition. This at least one further active agent is preferably an antibody specific for CD20 (an examples is rituximab or ofatumumab), an anthracyclin derivative (an example is doxorubicin or daunorubicin), a vinca alkaloid (an example is vincristine), a platin derivative (an example is cisplatin or carboplatin), daporinad (FK866), YM155, thalidomide and analogues thereof (an example is lenalidomide), or a proteasome inhibitor (an example is bortezumib).

The pharmaceutical composition of this invention may also be administered in combination with at least one corticosteroid, wherein said corticosteroid is given prior, concurrently, or subsequently to the administration of the pharmaceutical composition. Examples of the corticosteroids are prednisone, prednisolone and dexamethasone.

Several dosing regimens are possible. For example bendamustine can be administered as an oral formulation in a total amount of 200 mg/person/day on days 1-5+vincristine 2 mg i.v. on day 1+prednisone 100 mg/m$^2$ i.v. on days 1-5 every 3 weeks in patients with NHL. In patients with MM bendamustine can be administered as an oral formulation in a total amount of 400-500 mg/person/day on days 1 and 2+prednisone 60 mg/m$^2$ i.v. or orally on days 1-4 every 4 weeks. In patients with CCL bendamustine can be administered as an oral formulation in a total amount of 200 mg-300 mg/person/day on days 1 and 2) every 4 weeks+ prednisone 60 mg/m$^2$ i.v. or orally on days 1-4 every 4 weeks.

The advantage of the liquid filled hard gelatine capsule compositions according to the present invention further is, that the active ingredient(s), optionally in admixture with one or more excipients, do not need to be provided with a coating in order to further mask the taste of such ingredient and/or to protect the same against possible harmful effects by light and/or moisture such as oxidation, degradation, or to prevent that the subject may experience damage of the oral mucosa, due to the interaction with the active ingredient.

The following examples further illustrate the invention. It will be apparent to the skilled person that these examples are solely for illustrative purposes and must not be considered to limit the invention.

EXAMPLES

A) Examples Relating to the First Embodiment of the Invention

1. Capsule Formulations

Reference Example 1

Bendamustine Capsule Formulation (Prior Art)

20.0±1 mg of bendamustine hydrochloride were weighed into the body of an empty hard gelatine capsule, and put into a clear glass HPLC vial (6 ml) of Agilent. Capsules were closed by placing the cap on top of the body and slight pushing.

Capsules were stored at 40° C./75% RH (glass vial open) or 50° C. (glass vial closed). The amount of bendamustine hydrochloride and of related substances was measured with HPLC (column: Zorbax Bonus-RP, 5 μm; temperature of column oven: 30° C.; temperature of autosampler: 5° C.; detector: 254 nm). The results are shown in Table 1:

TABLE 1

Related substances and assay of bendamustine HCl (residual content) in bendamustine capsules

| Storage condition | Related substances | T = 0 | T = 1 month | Bendamustine HCl [% area] T = 0 | T = 1 month |
|---|---|---|---|---|---|
| 40° C./75% RH (open vial) | HP1 | 0.10 | 0.45 | 99.64 | 98.83 |
|  | NP1*[1] | 0.02 | 0.02 |  |  |
|  | BM1Dimer*[1] | 0.06 | 0.42 |  |  |
|  | BM1EE*[1] | 0.13 | 0.11 |  |  |
|  | HP2 | n.d.*[2] | n.d. |  |  |
|  | HP3 | n.d. | n.d. |  |  |
| 50° C. (closed vial) | HP1 | 0.10 | 1.46 | 99.64 | 97.51 |
|  | NP1 | 0.02 | 0.02 |  |  |
|  | BM1Dimer | 0.06 | 0.24 |  |  |
|  | BM1EE | 0.13 | 0.12 |  |  |
|  | HP2 | n.d. | n.d. |  |  |
|  | HP3 | n.d. | n.d. |  |  |

*[1]NP1: 4-[6-(2-Chloroethyl)-3,6,7,8-tetra-hydro-3-methyl-imidazo[4,5-h]-[1,4]benzothiazin-2-yl] butanoic acidBM1Dimer: 4-{5-[N-(2-Chloroethyl)-N-(2-{4-[5-bis(2-chloroethyl)amino-1-methylbenzimidazol-2-yl]butanoyloxy}ethyl)amino]-1-methylbenzimidazol-2-yl}butanoic acid
BM1EE: 4-[5-[Bis(2-chloroethyl)amino]-l-methyl-benzimidazo-2-yl] butanoic ethyl ester
*[2]n.d.: not detectable, i.e. beyond detection limit (area percentage less than 0.05%)

Reference Example 2

TABLE 2a

Bendamustine powder mixture for capsules

| Component | mg/dosage-form | Relative Content % |
|---|---|---|
| bendamustine hydrochloride | 55.1 | 21.09 |
| Mannitol | 141.4 | 54.11 |
| Microcrystalline cellulose (Avicel ® PH101) | 25.0 | 9.57 |
| Crosscarmellose sodium (Ac-Di-Sol ®) | 12.5 | 4.78 |
| Colloidal silicon dioxide (Aerosil ® 200) | 1.0 | 0.38 |
| Talc | 18.8 | 7.19 |
| Stearic acid | 7.5 | 2.87 |
| Sum | 261.3 | 100 |

For a batch size of 1000 capsules all excipients except for colloidal silicon dioxide and stearic acid were loaded into a Somakon vessel (5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the afore-mentioned conditions. Thereafter stearic acid was added and blending was continued for 1 minute. The blend was subsequently sieved through a 0.5 mm sieve, reloaded into the vessel and blended for another 30 seconds, all at the same conditions.

The blend was transferred to a capsule filling machine (Zanassi AZ 5) and filled into hard gelatine capsules (size 2) (mean mass: 259.5 mg (begin)–255.3 mg (end)) and hypromellose capsules (size 2) (mean mass: 255.8 (begin)–253.4 mg (end)) respectively. Capsules were stored at 40° C./75% RH in a closed glass vial. The amount of bendamustine hydrochloride as well as of related substances, like degradation products, by-products of synthesis were measured with HPLC (column: Zorbax Bonus-RP, 5 µm; temperature of column oven: 30° C.; temperature of autosampler: 5° C.; detector: 254 nm). The results are shown in Table 2b (filled in hypromellose capsules) and 2c (filled in gelatine capsules).

TABLE 2b

Bendamustine powder mixture in hypromellose capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.18 | 0.87 | 99.49 | 97.92 |
| | HP2 | n.d. | 0.38 | | |
| | HP3 | n.d. | 0.08 | | |
| | NP1 | n.d. | n.d. | | |
| | BM1Dimer | 0.09 | 0.14 | | |
| | BM1EE | 0.16 | 0.14 | | |
| | Unid RRT 0.65*[3] | n.d. | 0.05 | | |
| | Unid RRT 0.68 | n.d. | 0.06 | | |
| | Unid RRT 0.70 | n.d. | 0.19 | | |
| | Unid RRT 0.77 | n.d. | 0.05 | | |
| | Unid RRT 0.93 | n.d. | 0.05 | | |

*[3]Unidentified compound peak at relative retention time of 0.65 as compared to main peak

TABLE 2c

Bendamustine powder mixture in gelatine capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.25 | 1.25 | 99.30 | 97.79 |
| | HP2 | n.d. | 0.11 | | |
| | HP3 | n.d. | <0.05 | | |
| | NP1 | n.d. | n.d. | | |
| | BM1Dimer | 0.14 | 0.14 | | |
| | BM1EE | 0.16 | 0.14 | | |
| | Unid RRT 0.65 | n.d. | 0.05 | | |
| | Unid RRT 0.68 | 0.07 | 0.05 | | |
| | Unid RRT 0.70 | n.d. | 0.30 | | |
| | Unid RRT 0.77 | n.d. | n.d. | | |
| | Unid RRT 0.93 | n.d. | n.d. | | |

Reference Example 3

TABLE 3a

Bendamustine powder mixture for capsules

| Component | mg/dosage-form | Relative Content % |
|---|---|---|
| bendamustine hydrochloride | 55.1 | 21.09 |
| Lactose anhydrous | 141.4 | 54.11 |
| Microcrystalline cellulose (Avicel ® PH112) | 25.0 | 9.57 |
| Crosscarmellose sodium (Ac-Di-Sol ®) | 12.5 | 4.78 |
| Colloidal silicon dioxide (Aerosil ® 200) | 1.0 | 0.38 |
| Talc | 18.8 | 7.19 |
| Stearic acid | 7.5 | 2.87 |
| Sum | 261.3 | 100 |

For 1000 capsules all excipients except for colloidal silicon dioxide and stearic acid were loaded into a Somakon vessel (5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the afore-mentioned conditions. Thereafter stearic acid was added and blending was continued for 1 minute. The blend was subsequently sieved through a 0.5 mm sieve, reloaded into the vessel and blended for another 30 seconds, all at the same conditions.

The blend was transferred to a capsule filling machine (Zanassi AZ 5) and filled into hard gelatine capsules (size 2) (mean mass: 257.9 mg (begin)–255.2 mg (end)) and hypromellose capsules (size 2) (mean mass: 261.1 (begin)–257.8 mg (end)) respectively. Capsules were stored at 40° C./75% RH in a closed glass vial. The amount of bendamustine hydrochloride and of related substances was measured with HPLC, as described above. The results are shown in Table 3b (filled in hypromellose capsules) and 3c (filled in gelatine capsules).

TABLE 3b

Bendamustine powder mixture in hypromellose capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.18 | 0.86 | 99.50 | 98.17 |
| | HP2 | n.d. | 0.25 | | |
| | HP3 | n.d. | 0.06 | | |
| | NP1 | n.d. | n.d. | | |
| | BM1Dimer | 0.08 | 0.10 | | |
| | BM1EE | 0.15 | 0.14 | | |
| | Unid RRT 0.68 | n.d. | <0.05 | | |
| | Unid RRT 0.70 | n.d. | 0.19 | | |

TABLE 3c

Bendamustine powder mixture in gelatin capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.23 | 1.35 | 99.38 | 97.74 |
| | HP2 | n.d. | 0.06 | | |
| | HP3 | n.d. | n.d. | | |
| | NP1 | n.d. | n.d. | | |
| | BM1Dimer | 0.13 | 0.10 | | |
| | BM1EE | 0.16 | 0.14 | | |
| | Unid RRT 0.68 | n.d. | 0.05 | | |
| | Unid RRT 0.70 | n.d. | 0.32 | | |

Reference Example 4

TABLE 4a

Bendamustine powder composition for capsules

| Component | mg/dosage-form | Relative Content % |
|---|---|---|
| Bendamustine hydrochloride | 55.1 | 22.04 |
| Lactose anhydrous | 145.15 | 58.06 |
| Microcrystalline cellulose (Avicel ® PH112) | 31.25 | 12.50 |
| Ac-Di-Sol ® | 12.5 | 5.00 |
| Colloidal silicon dioxide (Aerosil ® 200) | 1.0 | 0.40 |
| Magnesium stearate | 2.5 | 1.00 |
| Ascorbic acid | 2.5 | 1.00 |
| Sum | 250 | 100.0 |

For 1000 capsules all excipients except for colloidal silicon dioxide and magnesium stearate were loaded into a Somakon vessel (2.5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the afore-mentioned conditions. Thereafter magnesium stearate was added and blending was continued for 1 minute. The blend was subsequently sieved through a 0.5 mm sieve, reloaded into the vessel and blended for another 30 seconds, all at the same conditions.

The blend was transferred to a capsule filling machine (Zanassi AZ 5) and filled into hard gelatine capsules (size 2) (mean mass: 241.3 mg (begin)–244. mg (end)) and hypromellose capsules (size 2) (mean mass: 243.5 (begin)–243. mg (end)) respectively. Capsules were stored at 40° C./75% RH in a closed glass vial. The amount of bendamustine hydrochloride and of related substances was measured with HPLC, as described above. The results are shown in Table 4b (filled into hypromellose capsules) and 4c (filled in gelatine capsules).

TABLE 4b

Bendamustine powder composition in hypromellose capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.18 | 0.86 | 99.49 | 98.29 |
| | HP2 | n.d. | 0.25 | | |
| | HP3 | n.d. | 0.06 | | |
| | NP1 | n.d. | n.d. | | |
| | BM1Dimer | 0.08 | 0.10 | | |
| | BM1EE | 0.15 | 0.14 | | |
| | Unid RRT 0.57 | n.d. | 0.07 | | |
| | Unid RRT 0.63 | n.d. | 0.05 | | |
| | Unid RRT 0.64 | n.d. | n.d. | | |
| | Unid RRT 0.68 | n.d. | n.d. | | |
| | Unid RRT 0.69 | n.d. | n.d. | | |
| | Unid RRT 0.70 | n.d. | 0.19 | | |
| | Unid RRT 0.75 | n.d. | 0.07 | | |
| | Unid RRT 0.77 | n.d. | 0.05 | | |
| | Unid RRT 0.93 | n.d. | 0.07 | | |

TABLE 4c

Bendamustine powder composition in gelatin capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.29 | 1.10 | 99.26 | 96.38 |
| | HP2 | n.d. | 0.55 | | |
| | HP3 | n.d. | n.d. | | |
| | NP1 | n.d. | n.d. | | |
| | BM1Dimer | 0.12 | 0.17 | | |
| | BM1EE | 0.15 | 0.15 | | |
| | Unid RRT 0.58 | n.d. | 0.44 | | |
| | Unid RRT 0.62 | n.d. | 0.23 | | |
| | Unid RRT 0.65 | n.d. | 0.10 | | |
| | Unid RRT 0.68 | 0.07 | 0.07 | | |
| | Unid RRT 0.69 | n.d. | 0.06 | | |
| | Unid RRT 0.70 | 0.05 | 0.25 | | |
| | Unid RRT 0.76 | n.d. | 0.17 | | |
| | Unid RRT 0.77 | n.d. | 0.07 | | |
| | Unid RRT 0.77 | n.d. | 0.08 | | |
| | Unid RRT 0.78 | n.d. | 0.09 | | |
| | Unid RRT 0.79 | n.d. | 0.06 | | |
| | Unid RRT 0.91 | n.d. | n.d. | | |
| | Unid RRT 0.94 | n.d. | 0.06 | | |
| | Unid RRT 1.11 | n.d. | n.d. | | |
| | Unid RRT 1.18 | n.d. | n.d. | | |

Example 1

TABLE 5a

| Liquid filled hard capsule | | |
|---|---|---|
| Component | mg/dosage-form | Relative Content % |
| bendamustine hydrochloride | 55.1 | 9.18 |
| Pluronic ® L44 NF | 450.70 | 75.12 |
| Cremophor ® RH 40 | 81.85 | 13.64 |
| Softisan ® 645 | — | — |
| Methyl paraben | 1.20 | 0.20 |
| Propyl paraben | 0.12 | 0.02 |
| Butyl hydroxytoluene | 0.12 | 0.02 |
| Ethanol | 10.91 | 1.82 |

0.68 g of methylparaben, 0.068 g of propylparaben and 0.068 g of butylhydroxytoluene were weighed and dissolved in 6.14 g of ethanol. Cremophor® RH 40 was melted at 40° C. in a sufficient amount. 5.56 g of the ethanolic solution obtained, 36.83 g of the melted Cremophor® RH 40 and 202.82 g of Pluronic® L44 NF were weighed and mixed at 800 rpm using a mechanical stirrer until the mixture became transparent. The mixture was allowed to solidify by placing it at 10° C. 24.80 g of bendamustine hydrochloride was subsequently added to the solidified blend by manual stirring and then distributed over the blend by homogenisation using an Ultraturrax T18 high speed homogeniser at 15500 rpm for 10 minutes. The homogenised suspension was filled into hard gelatine capsules with a CFS 1200 capsule filling and sealing machine, operated at 25° C. The capsules were closed and sealed. The liquid filled capsules were stored in closed amber glass bottles with screw plugs at 40° C./75% RH, at 30° C./65% RH, at 25° C./60% RH and at 5° C. The amount of bendamustine hydrochloride as well as of related substances, like degradation products, by-products of synthesis was measured with HPLC (column: Zorbax Bonus-RP, 5 μm; temperature of column oven: 30° C.; temperature of autosampler: 5° C.; detector: 254 nm). The results are shown in Table 5b.

TABLE 5b

| Related substances and assay of bendamustine HCl (residual content) | | | | | |
|---|---|---|---|---|---|
| | | | | Bendamustine HCl [% area] | |
| Storage condition | Related substances | T = 0 | T = 3 months | T = 0 | T = 3 months |
| 40° C./75% RH (closed vial) | HP1 | 0.09 | 0.07 | 98.8 | 98.5 |
| | NP1 | n.d. | n.d. | | |
| | BM1Dimer | 0.02 | 0.03 | | |
| | BM1EE | 0.15 | 0.15 | | |
| | Individual unknown impurity | 0.01 | 0.08 | | |
| 30° C./65% RH (closed vial) | HP1 | 0.09 | 0.06 | 98.8 | 98.9 |
| | NP1 | n.d. | n.d. | | |
| | BM1Dimer | 0.02 | 0.03 | | |
| | BM1EE | 0.15 | 0.15 | | |
| | Individual unknown impurity | 0.01 | 0.03 | | |
| 25° C./60% RH (closed vial) | HP1 | 0.09 | 0.07 | 98.8 | 99.0 |
| | NP1 | n.d. | n.d. | | |
| | BM1Dimer | 0.02 | 0.03 | | |
| | BM1EE | 0.15 | 0.15 | | |
| | Individual unknown impurity | 0.01 | 0.03 | | |
| 5° C. (closed vial) | HP1 | 0.09 | 0.07 | 98.8 | 99.8 |
| | NP1 | n.d. | n.d. | | |
| | BM1Dimer | 0.02 | 0.02 | | |
| | BM1EE | 0.15 | 0.15 | | |
| | Individual unknown impurity | 0.01 | n.d. | | |

Example 2

TABLE 6a

| Liquid filled hard capsule | | |
|---|---|---|
| Component | mg/dosage-form | Relative Content % |
| bendamustine hydrochloride | 55.1 | 9.18 |
| Pluronic ® L44 NF | — | — |
| Cremophor ® RH 40 | 532.55 | 88.76 |
| Softisan ® 645 | — | — |
| Methyl paraben | 1.20 | 0.20 |
| Propyl paraben | 0.12 | 0.02 |
| Butyl hydroxytoluene | 0.12 | 0.02 |
| Ethanol | 10.91 | 1.82 |

0.68 g of methylparaben, 0.068 g of propylparaben and 0.068 g of butylhydroxytoluene were weighed and dissolved in 6.14 g of ethanol. Cremophor® RH 40 was melted at 40° C. in a sufficient amount. 5.56 g of the ethanolic solution obtained and 239.65 g of the melted Cremophor® RH 40 were weighed and mixed at 800 rpm using a mechanical stirrer until the mixture became transparent. The mixture was allowed to solidify and cool to room temperature. 24.80 g of bendamustine hydrochloride was subsequently added to the solidified blend by manual stirring and then distributed over the blend by homogenisation using an Ultraturrax T18 high speed homogeniser at 15500 rpm for 10 minutes. The homogenised suspension was filled into hard gelatine capsules with a CFS 1200 capsule filling and sealing machine, operated at 40° C. The capsules were closed and sealed.

The liquid filled capsules so obtained were stored in closed amber glass bottles with screw plugs at 40° C./75% RH, at 30° C./65% RH, at 25° C./60% RH and at 5° C. The amount of bendamustine hydrochloride as well as of related substances, like degradation products, by-products of synthesis was measured with HPLC, as described above.

The results are shown in Table 6b:

TABLE 6b

| Related substances and assay of bendamustine HCl (residual content) | | | | | |
|---|---|---|---|---|---|
| | | | | Bendamustine HCl [% area] | |
| Storage condition | Related substances*1 | T = 0 | T = 3 months | T = 0 | T = 3 months |
| 40° C./75% RH (closed vial) | HP1 | 0.08 | 0.07 | 100.10 | 99.0 |
| | NP1 | 0.01 | 0.02 | | |
| | BM1Dimer | 0.03 | 0.09 | | |
| | BM1EE | 0.16 | 0.17 | | |

TABLE 6b-continued

Related substances and assay of bendamustine HCl (residual content)

| Storage condition | Related substances*[1] | T = 0 | T = 3 months | Bendamustine HCl [% area] T = 0 | T = 3 months |
|---|---|---|---|---|---|
| | Individual unknown impurity | 0.02 | 0.09 | | |
| 30° C./65% RH (closed vial) | HP1 | 0.08 | 0.06 | 100.1 | 100.4 |
| | NP1 | 0.01 | n.d. | | |
| | BM1Dimer | 0.03 | 0.04 | | |
| | BM1EE | 0.16 | 0.13 | | |
| | Individual unknown impurity | 0.02 | 0.03 | | |
| 25° C./60% RH (closed vial) | HP1 | 0.08 | 0.10 | 100.1 | 100.3 |
| | NP1 | 0.01 | n.d. | | |
| | BM1Dimer | 0.03 | 0.03 | | |
| | BM1EE | 0.16 | 0.14 | | |
| | Individual unknown impurity | 0.02 | 0.02 | | |
| 5° C. (closed vial) | HP1 | 0.08 | 0.09 | 100.1 | 99.5 |
| | NP1 | 0.01 | 0.01 | | |
| | BM1Dimer | 0.03 | 0.03 | | |
| | BM1EE | 0.16 | 0.15 | | |
| | Individual unknown impurity | 0.02 | 0.02 | | |

Example 3

TABLE 7a

| Liquid filled hard capsule | | |
|---|---|---|
| Component | mg/dosage-form | Relative Content % |
| Bendamustine hydrochloride | 55.1 | 9.18 |
| Pluronic ® L44 NF | — | — |
| Cremophor ® RH 40 | 81.85 | 13.64 |
| Softisan ® 645 | 450.70 | 75.12 |
| Methyl paraben | 1.20 | 0.20 |
| Propyl paraben | 0.12 | 0.02 |
| Butyl hydroxytoluene | 0.12 | 0.02 |
| Ethanol | 10.91 | 1.82 |

0.68 g of methylparaben, 0.068 g of propylparaben and 0.068 g of butylhydroxytoluene were weighed and dissolved in 6.14 g of ethanol. Cremophor® RH 40 was melted at 40° C. in a sufficient amount. 5.56 g of the ethanolic solution obtained, 36.83 g of the melted Cremophor® RH 40 and 202.82 g of Softisan® 645 were weighed and mixed at 800 rpm using a mechanical stirrer until the mixture became transparent. The mixture was allowed to solidify by placing it at 10° C. 24.80 g of bendamustine hydrochloride was subsequently added to the solidified blend by manual stirring and then distributed over the blend by homogenisation using an Ultraturrax T18 high speed homogeniser at 15500 rpm for 10 minutes. The homogenised suspension was filled into hard gelatine capsules with a CFS 1200 capsule filling and sealing machine, operated at 30° C. The capsules were closed and sealed. The liquid filled capsules were stored in closed amber glass bottles with screw plugs at 40° C./75% RH, at 30° C./65% RH, at 25° C./60% RH and at 5° C. The amount of bendamustine hydrochloride as well as of related substances, like degradation products, by-products of synthesis was measured with HPLC, as described above. The results are shown in Table 7b:

TABLE 7b

Related substances and assay of bendamustine HCl (residual content)

| Storage condition | Related substances*[1] | T = 0*[2] | T = 3 months | Bendamustine HCl [% area] T = 0 | T = 3 months |
|---|---|---|---|---|---|
| 40° C./75% RH (closed vial) | HP1 | 0.08 | 0.06 | 99.6 | 99.5 |
| | NP1 | n.d. | 0.01 | | |
| | BM1Dimer | 0.03 | 0.36 | | |
| | BM1EE | 0.15 | 0.26 | | |
| | Individual unknown impurity | 0.03 | 0.13 | | |
| 30° C./65% RH (closed vial) | HP1 | 0.08 | 0.11 | 99.6 | 99.9 |
| | NP1 | n.d. | n.d. | | |
| | BM1Dimer | 0.03 | 0.09 | | |
| | BM1EE | 0.15 | 0.17 | | |
| | Individual unknown impurity | 0.03 | 0.04 | | |
| 25° C./60% RH (closed vial) | HP1 | 0.08 | 0.11 | 99.6 | 100.0 |
| | NP1 | n.d. | n.d. | | |
| | BM1 Dimer | 0.03 | 0.09 | | |
| | BM1EE | 0.15 | 0.17 | | |
| | Individual unknown impurity | 0.03 | 0.04 | | |
| 5° C. (closed vial) | HP1 | 0.08 | 0.07 | 99.60 | 100.1 |
| | NP1 | n.d. | 0.01 | | |
| | BM1Dimer | 0.03 | 0.03 | | |
| | BM1EE | 0.15 | 0.15 | | |
| | Individual unknown impurity | 0.03 | 0.02 | | |

Example 4

TABLE 8 further Liquid filled hard capsule formulations

| | Relative content (%) | | | | | | |
|---|---|---|---|---|---|---|---|
| Component | Ex 4.1 | Ex 4.2 | Ex 4.3 | Ex 4.4 | Ex 4.5 | Ex 4.6 | Ex 4.7 |
| Pluronic ® L44 | — | 88.2 | — | 45.4 | — | 90.8 | — |
| Cremophore ® EL | — | — | 80.7 | — | 90.8 | — | 88.4 |
| Cremophor ® RH 40 | 90.8 | — | — | — | — | — | — |
| Gelucire ® 44/14 | — | — | 10.0 | 45.4 | — | — | — |
| Colloidal silicon dioxide | — | 2.0 | — | — | — | — | 1.7 |
| Bendamustine HCl | 9.2 | 9.8 | 9.3 | 9.2 | 9.2 | 9.2 | 9.9 |

2. Disintegration and Dissolution Tests

Example 5

Disintegration tests for the liquid filled capsule formulations of examples 1, 2 and 3 were carried out in 1000.0 ml of buffer solution pH=1.0±0.05, using disintegration Apparatus A, operated at 37.0° C.±0.5° C. The results are listed in Tables 8a, 8b and 8c.

Example 6

Dissolution tests for the liquid filled capsule formulations of examples 1, 2 and 3 were carried out in artificial gastric acid solution at pH 1.5 (see Ph Eur: 2.9.3: Dissolution test for solid dosage forms in Recommended Dissolution Media).

The dissolution samples were tested for assay by HPLC (column: Zorbax Bonus-RP, 5 μm; temperature of column oven: 30° C.; temperature of autosampler: 5° C.; detector: 254 nm). Artificial gastric fluid pH 1.5 was prepared by placing 250.0 mL of 0.2M potassium chloride 0.2M into a 1000 mL volumetric flask, adding 207.0 mL of 0.2 M hydrochloric acid, then diluting to 1000 mL with Milli-Q water. The pH was measured and adjusted, if necessary, with 2N hydrochloric acid or 2N potassium hydroxide to a pH of 1.5±0.05.

The dissolution test was conducted according to Chapter 2.9.3. of European Pharmacopoeia 6.0, using Apparatus 2 (Paddle-apparatus). The rotation speed of the paddle was 50 rpm, the temperature was 37° C.±0.5° C., the amount of dissolution medium was 500 ml.

The results for the liquid filled hard capsules of examples 1, 2 and 3 are shown in Tables 9a, 9b and 9c:

TABLE 9a

Liquid filled hard capsules of example 1

| Test | Time | |
|---|---|---|
| | T = 0 months | T = 3 months |
| Temperature 40° C. 75% RH | | |
| Disintegration (minute:second) | 03:23 | 03:30 |
| Dissolution (%) pH 1.5 | | |
| 10' | Not tested | 10.4 |
| 20' | | 35.1 |
| 30' | | 51.1 |
| Temperature 30° C. 65% RH | | |
| Disintegration (minute:second) | 03:23 | 03:26 |
| Dissolution (%) pH 1.5 | | |
| 10' | Not tested | 7.0 |
| 20' | | 24.0 |
| 30' | | 54.6 |
| Temperature 25° C. 60% RH | | |
| Disintegration (minute:second) | 03:23 | 03:33 |
| Dissolution (%) pH 1.5 | | |
| 10' | Not tested | 37.4 |
| 20' | | 52.4 |
| 30' | | 71.6 |
| Temperature 5° C. | | |
| Disintegration (minute:second) | 03:23 | 03:23 |
| Dissolution (%) pH 1.5 | | |
| 10' | Not tested | 57.0 |
| 20' | | 76.7 |
| 30' | | 83.1 |

TABLE 9b

Liquid filled hard capsule of example 2

| Test | Time | |
|---|---|---|
| | T = 0 months | T = 3 months |
| Temperature 40° C. 75% RH | | |
| Disintegration (minute:second) | 03:52 | 02:58 |
| Dissolution (%) pH 1.5 | | |
| 10' | Not tested | 65.2 |
| 20' | | 88.7 |
| 30' | | 102.0 |
| Temperature 30° C. 65% RH | | |
| Disintegration (minute:second) | 03:52 | 03:09 |
| Dissolution (%) pH 1.5 | | |
| 10' | Not tested | 48.1 |
| 20' | | 80.9 |
| 30' | | 93.7 |
| Temperature 25° C. 60% RH | | |
| Disintegration (minute:second) | 03:52 | 02:53 |
| Dissolution (%) pH 1.5 | | |
| 10' | Not tested | 54.5 |
| 20' | | 80.7 |
| 30' | | 94.4 |
| Temperature 5° C. | | |
| Disintegration (minute:second) | 03:52 | 02:56 |
| Dissolution (%) pH 1.5 | | |
| 10' | Not tested | 57.9 |
| 20' | | 90.0 |
| 30' | | 98.0 |

TABLE 9c

Liquid filled hard capsule of example 3

| Test | Time | |
|---|---|---|
| | T = 0 months | T = 3 months |
| Temperature 40° C. 75% RH | | |
| Disintegration (minute:second) | 03:59 | 03:36 |
| Dissolution (%) pH 1.5 | | |
| 10' | Not tested | 28.5 |
| 20' | | 49.1 |
| 30' | | 62.9 |
| Temperature 30° C. 65% RH | | |
| Disintegration (minute:second) | 03:59 | 03:34 |
| Dissolution (%) pH 1.5 | | |
| 10' | Not tested | 17.5 |
| 20' | | 35.2 |
| 30' | | 58.1 |
| Temperature 25° C. 60% RH | | |
| Disintegration (minute:second) | 03:59 | 03:27 |
| Dissolution (%) pH 1.5 | | |
| 10' | Not tested | 25.9 |
| 20' | | 44.2 |
| 30' | | 62.1 |

TABLE 9c-continued

Liquid filled hard capsule of example 3

| Test | Time | |
|---|---|---|
| | T = 0 months | T = 3 months |
| Temperature 5° C. | | |
| Disintegration (minute:second) | 03:59 | 03:18 |
| Dissolution (%) pH 1.5 | | |
| 10' | Not tested | 15.9 |
| 20' | | 31.1 |
| 30' | | 46.6 |

As may be taken from the above Tables 9a, 9b and 9c, only the liquid filled hard capsule formulation of example 2 according to the invention shows the preferred fast dissolution profile of bendamustine, which is at least 60% in 10 minutes, 70% in 20 minutes and 80% in 30 minutes, as measured with a paddle apparatus at 50 rpm according to the European Pharmacopoeia in 500 ml of an artificial gastric fluid.

Example 7

TABLE 10 results of analytical tests on formulations of example 4

| Analytical Test | Limits | Ex. 4.2 | Ex. 4.7 | Ex 4.3 | Ex 4.5 | Ex 4.6 | Ex. 4.4 | Ex 4.1 |
|---|---|---|---|---|---|---|---|---|
| Identification (HPLC) | Positive | Positive | Positive | Positive | Positive | Positive | Positive | Positive |
| Content uniformity | Complies | N/A | N/A | N/A | Complies | Complies | Complies (RSD 4.40) | Complies (RSD 2.66) |
| Assay (HPLC) | 95.0%-105.0% | 98.2 | 101.0 | 117.9 | 98.6 | 103.3 | 95.8 | 98.0 |
| Related substances (HPLC) | | | | | | | | |
| HP1 | =0.50% | 0.30 | 0.30 | 0.11 | 0.13 | 0.07 | 0.07 | 0.05 |
| BM1 Dimer | =0.20% | 0.05 | 0.04 | 0.04 | 0.05 | 0.04 | 0.04 | 0.04 |
| BM1EE | =0.50% | 0.14 | 0.15 | 0.15 | 0.14 | 0.15 | 0.14 | 0.14 |
| NP1 | =0.20% | 0.01 | 0.01 | 0.01 | 0.01 | 0.01 | 0.01 | 0.01 |
| Ind. Unknown impurity | =0.10% | 0.04 | 0.14 | 0.04 | 0.05 | 0.02 | 0.01 | 0.03 |
| Total impurities | =1.50% | 0.54 | 0.68* | 0.35 | 0.38 | 0.29 | 0.27 | 0.29 |
| Total impurities after 3 months' storage at 40°/75% RH | | 0.35 | 1.12 | | | | | 1.12 |
| Dissolution Test (Medium: buffer pH = 1.5) | | | | | | | | |
| (% 10 min) | 80% in 30 min | 96.9 | 25.6 | 67.3 | 46.8 | 95.7 | 65.3 | 56.9 |
| (% 20 min) | | 97.1 | 46.5 | 96.2 | 74.3 | 96.7 | 102.5 | 80.4 |
| (% 30 min) | | 96.7 | 72.4 | 104.5 | 88.9 | 95.0 | 109.5 | 93.8 |
| Dissolution test after 3 months' storage at 40°/75% RH; | | | | | | | | |
| (% 30 min) | | 91 | 72 | | | | | 92 |

3. In Vivo Tests

Example 8

The liquid filled hard capsules of example 2, containing 50 mg of bendamustine, were orally administered to male and female beagle dogs in comparison with the capsules of reference example 1 in order to determine the bioavailability of 1 dose (i.e. 50 mg) of bendamustine (AUC and Cmax) and to determine the level of variability in bioavailability of these capsule formulations: (i.e. % CV on AUC and Cmax).

A further formulation (formulation X) was also included in the test but since this formulation was outside the scope of the present invention no details are provided. The total number of animals required was 16. The basic study design was a cross-over design with 8 animals per arm.

Period 1 (Single Dose of Capsule, Day 1):

| Group | Treatment | Composition | Dose # (mg) | Number of animals |
|---|---|---|---|---|
| 1 | Bendamustine | Reference Capsule | 50 | 4 Male + 4 Female |
| 2 | Bendamustine | Reference Capsule | 50 | 4 Male + 4 Female |

There was a one week wash-out period.

Period 2 (1 Week after Period 1, Single Dose of Either of the Following Formulations, Day 8):

| Group | Treatment | Composition | Dose # (mg) | Number of animals |
|---|---|---|---|---|
| 1 | Bendamustine | Formulation example 2 | 50 | 4 Male + 4 Female |

-continued

| Group | Treatment | Composition | Dose # (mg) | Number of animals |
|---|---|---|---|---|
| 2 | Bendamustine | Formulation X | 50 | 4 Male + 4 Female |

The mean plasma profiles vs. time for both the capsule formulation (reference example 1) and the liquid filled capsule formulation of Example 2 are shown in FIG. 1.

Example 9

An open label, randomized two-way crossover study to assess the absolute bioavailability of oral bendamustine in patients with cancer was conducted to assess the absolute bioavailability of bendamustine administered as an oral formulation (example 2). Besides assessing the pharmacokinetics of bendamustine in plasma following oral and i.v. administration, a further objective was to evaluate the safety and tolerability of bendamustine following i.v. and especially oral administration of the formulation of example 2. 6 Patients resided in hospital for 2 periods; Day −1 to 2 (period 1) and Day 7-9 (period 2). Patients were enrolled to receive in a random order one of the following two treatments on Day 1 and 8:

- a single oral dose of 110.2 mg (2×55.1 mg) bendamustine hydrochloride (HCl), being equivalent to about 100 mg bendamustine free base and
- a single i.v. dose of 100 mg bendamustine HCl, equivalent to 90.7 mg bendamustine free base.

The dose of bendamustine HCl (100 mg intravenous, 110.2 mg orally) was selected based on the safety of the oral formulation in preclinical studies and based on the safety of the registered i.v. formulation.

Blood samples were taken on days 1 and 2 and 8 and 9 to determine the pharmacokinetics of bendamustine and its metabolites in plasma after oral and i.v. administration of bendamustine. The time-points were chosen based on data from the literature (Preiss 1985) following i.v. administration of bendamustine. Preiss and co-workers reported a mean bioavailability of bendamustine of 57% (range: 25-94%; % CV=44%) after oral administration of bendamustine as capsule at doses of 250-350 mg in patients with cancer. Bendamustine was administered on days 1 and 8 in the morning either orally or intravenously as a single dose (as bendamustine hydrochloride 100 mg i.v. or 110.2 mg orally).

Bendamustine was administered orally as two liquid-filled hard-shell capsules with 250 mL of water or as i.v. infusion over 30 minutes.

Patients had to fast overnight for at least 8 hours before oral and i.v. administration of bendamustine in the morning, except for drinking water which is allowed up to 2 hours prior to administration of study medication. Patients are allowed to have a light breakfast 2 hours after each administration.

The total duration of the admission period was 6 days (day −1 to 2 and day 7-9) excluding screening and a post study visit.

Certain medication was prohibited from 2 weeks before the first administration of the first study drug.

Figure 2:
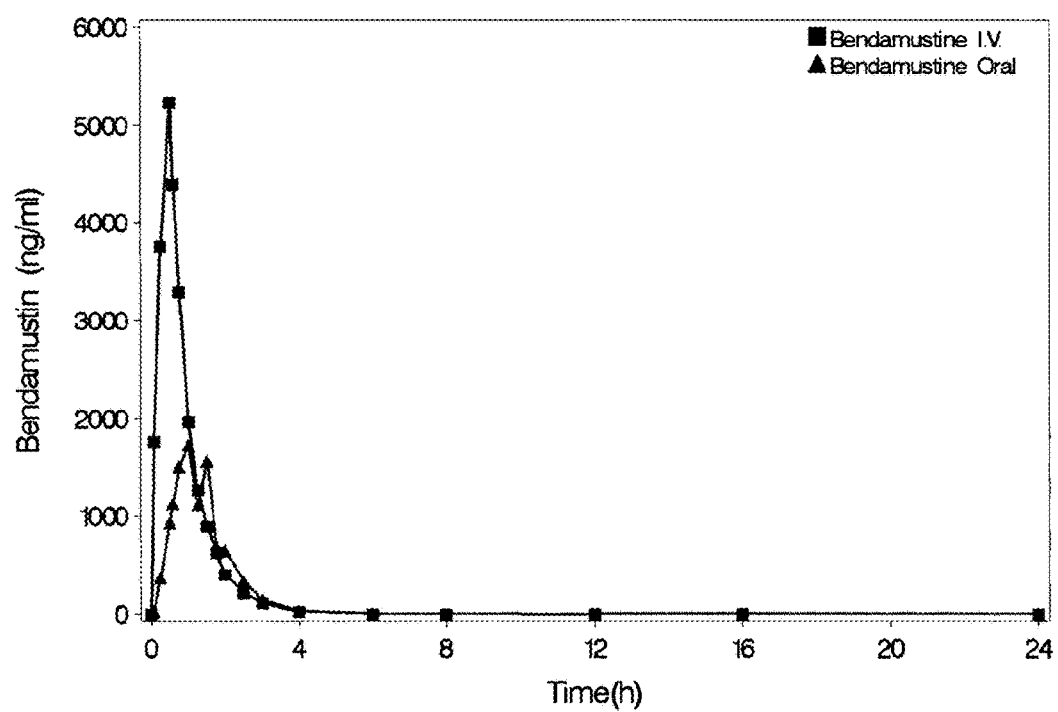
FIG. 2 shows the mean plasma vs. time profile obtained after administering bendamustine hydrochloride in the form of the intravenous preparation, as marketed in Germany under the trademark Ribomustin®, and the liquid filled hard capsule formulation of example 2 to patients with cancer.

The blood concentration-time curve as obtained after evaluating 6 patients is shown in FIG. 2. The mean value for the absolute bioavailability, calculated as $AUC_{oral}/dose/AUC_{i.v.}/dose*100\%$ was 58.5%, with a standard deviation of 9.3 and an interindividual variation (expressed as % CV) of 15.9.

Therefore the bioavailability of bendamustine hydrochloride from the oral formulation of example 2 was found to be in accordance with that previously reported for bendamustine-containing capsules in the literature (Preiss), but the interpatient variability is much lower.

B) Examples Relating to the Second Embodiment of the Invention

1. Compatibility Tests

Example 10a

For compatibility testing mixtures containing bendamustine hydrochloride and an excipient at a ratio of 1:1 (m/m) were prepared. The excipients were selected from mannitol and lactose. After preparation the mixtures were packed in clear glass HPLC-Vials (6 ml) Agilent and stored at different storage conditions as shown in Table 11 below. At defined time points samples were removed from storage and tested for purity (HPLC; column: Zorbax Bonus-RP, 5 µm; temperature of column oven: 30° C.; temperature of autosampler: 5° C.; detector: 254 nm) and appearance.

TABLE 11

Storage Conditions
Bendamustine hydrochloride and excipients for oral formulation

|  | Tested time points | |
| --- | --- | --- |
| Storage condition | T = 0 | T = 1 month |
| (1) 50° C., Vials closed | n = 2 | n = 1 |
| (2) 70° C., Vials closed* | n = 2 | n = 2 |
| (3) 40° C./75% r.h., Vials open** | n = 2 | n = 2 |

*stored at 50° C. for one month before storage at 70° C.
**stored at 25° C./60% r.h. for one month before storage at 40° C./75%

In all these mixtures, the bendamustine hydrochloride content (measured by HPLC) barely changed and always remained above 99% for all three storage conditions. The hydrolysis product HP1 was barely detectable (Area %<0.2) for all three storage conditions.

Appearance tests of the named bendamustine hydrochloride mixtures were carried out with the naked eye. All the investigated mixtures complied with the specifications and gave white to off-white powder both immediately after preparation and after one month of storage under all three storage conditions.

Example 10b

For further compatibility testing in accordance with the methods of example 1a, mixtures containing bendamustine hydrochloride and an excipient at a ratio of 1:1 (m/m) were prepared. The excipients were selected from Opadry®, Eudragit® E PO, sodium carboxymethylcellulose (Avicel® RC 591) and cross-linked polyvinylpyrrolidone (Crospovidone).

In the case of Eudragit® E PO the initial amounts of the impurities HP1 (hydrolysis product) and BM1DIMER were significantly increased (HP1:1.5%, BM1DIMER: 1%) but during storage a decrease of these impurities could be detected at all storage conditions independent of the influence of humidity. In the case of cross-linked polyvinylpyrrolidone a significant increase of HP1 from 0.1% to 0.4% could be detected at the storage condition 40°/75% R.H./vials open. At all other storage conditions (vials closed) no increase of HP1 could be detected.

The appearance of the mixtures containing Eudragit® E PO and cross-linked polyvinylpyrrolidone changed at the storage condition 70° C./vials closed. Both mixtures got lightly sticky. Additionally the colour of the mixture with cross-linked polyvinylpyrrolidone changed from white too cream-coloured.

In case of the mixtures containing Opadry® and Avicel® RC591 the colour also changed to cream-coloured at the storage condition 70° C./vials closed.

2. Tablet Formulations

Example 11

253 g of a mixture comprising mannitol as the main excipient and microcrystalline cellulose, Ac-Di-Sol®, colloidal silicon dioxide, talc and stearic acid in the relative quantities mentioned in the following table 2a was prepared by mixing in a 1 liter cube blender (Erweka) for 15 minutes. Thereafter 10.612 g of the mixture and 3.0 g of bendamustine hydrochloride were sieved through a 0.425 mm sieve and then transferred into a Turbula mixer T2A, equipped with a glass vial of 50 ml and subsequently mixed for 10 minutes at 60 rpm.

From this mixture round tablets were compressed having the following characteristics:

Mean value diameter: 9.1 mm; mean value mass: 247.7 mg; mean value hardness: 81N.

TABLE 12a

| Tablet | | |
|---|---|---|
| Component | mg/dosage-form | Relative Content % |
| bendamustine hydrochloride | 55.1 | 22.04 |
| Mannitol | 141.4 | 56.56 |
| Microcrystalline cellulose (Avicel ® PH112) | 25.0 | 10.00 |
| Ac-Di-Sol ® | 12.5 | 5.00 |
| Colloidal silicon dioxide (Aerosil ® 200) | 1.0 | 0.40 |
| Talc | 12.5 | 5.00 |
| Stearic acid | 2.5 | 1.00 |

Tablets were stored at 40° C./75% RH (glass vial open) or 50° C. (glass vial closed). The amount of bendamustine hydrochloride as well as of related substances, like degradation products, by-products of synthesis were measured with HPLC (column: Zorbax Bonus-RP, 5 μm; temperature of column oven: 30° C.; temperature of autosampler: 5° C.; detector: 254 nm). The results are shown in Table 12b.

TABLE 12b

Related substances and assay of bendamustine HCl (residual content)

| Storage condition | Related substances*[1] | T = 0*[2] | T = 1 month | Bendamustine HCl [% area] T = 0 | T = 1 month |
|---|---|---|---|---|---|
| 40° C./75% RH (open vial) | HP1 | 0.13 | 0.22 | 99.60 | 99.13 |
| | NP1 | 0.02 | 0.02 | | |
| | BM1Dimer | 0.06 | 0.25 | | |
| | BM1EE | 0.13 | 0.12 | | |
| | HP2 | n.d. | 0.13 | | |
| | HP3 | n.d. | 0.03 | | |
| 50° C. (closed vial) | HP1 | 0.13 | 0.53 | 99.60 | 98.94 |
| | NP1 | 0.02 | 0.02 | | |
| | BM1Dimer | 0.06 | 0.14 | | |
| | BM1EE | 0.13 | 0.11 | | |
| | HP2 | n.d. | 0.05 | | |
| | HP3 | n.d. | n.d. | | |

*[1]NP1: 4-[6-(2-Chloroethyl)-3,6,7,8-tetra-hydro-3-methyl-imidazo[4,5-h]-[1,4]benzothiazin-2-yl] butanoic acid
BM1Dimer: 4-{5-[N-(2-Chloroethyl)-N-(2-{4-[5-bis(2-chloroethyl)amino-1-methylbenzimidazol-2-yl]butanoyloxy}ethyl)amino]-1-methylbenzimidazol-2-yl}butanoic acid
BM1EE: 4-[5-[Bis(2-chloroethyl)amino]-1-methyl-benzimidazol-2-yl] butanoic ethyl ester
*[2]n.d.: not detectable, i.e. beyond detection limit (area percentage less than 0.05%)

Example 12

A mixture and tablets were prepared in the same way as described in Example 11, but using the compounds and relative amounts as indicated in the following Table 3a.

The tablets had the following characteristics:

Mean value diameter: 9.1 mm; mean value mass: 248.9 mg.

TABLE 13a

| Tablet | | |
|---|---|---|
| Component | mg/dosage-form | Relative Content % |
| bendamustine hydrochloride | 55.1 | 22.04 |
| Lactose anhydrous | 141.4 | 56.56 |
| Microcrystalline cellulose (Avicel ® PH112) | 25.0 | 10.00 |
| Ac-Di-Sol ® | 12.5 | 5.00 |
| Colloidal silicon dioxide (Aerosil ® 200) | 1.0 | 0.40 |
| Talc | 12.5 | 5.00 |
| Stearic acid | 2.5 | 1.00 |

Tablets were stored at 40° C./75% RH (glass vial open) or 50° C. (glass vial closed).

The amount of bendamustine hydrochloride and of related substances was measured with HPLC as mentioned above. The results are shown in Table 13b:

TABLE 13b

Related substances and assay of bendamustine HCl (residual content)

| Storage condition | Related substances | T = 0 | T = 1 month | Bendamustine HCl [% area] T = 0 | T = 1 month |
|---|---|---|---|---|---|
| 40° C./75% RH (open vial) | HP1 | 0.12 | 0.22 | 99.60 | 99.13 |
| | NP1 | 0.02 | 0.02 | | |
| | BM1Dimer | 0.06 | 0.26 | | |
| | BM1EE | 0.13 | 0.13 | | |
| | HP2 | n.d. | 0.11 | | |
| | HP3 | n.d. | 0.03 | | |
| 50° C. (closed vial) | HP1 | 0.12 | 0.57 | 99.61 | 98.88 |
| | NP1 | 0.02 | 0.02 | | |
| | BM1Dimer | 0.06 | 0.13 | | |
| | BM1EE | 0.13 | 0.11 | | |
| | HP2 | n.d. | 0.05 | | |
| | HP3 | n.d. | n.d. | | |

Example 13

Tablets were prepared in the same way as described in Example 11, but using the compounds and relative amounts as indicated in the following Table 14a.

The tablets had the following characteristics:
Mean value diameter: 9.1 mm; mean value mass: 247.8 mg.

TABLE 14a

| Tablet | | |
|---|---|---|
| Component | mg/dosage-form | Relative Content % |
| Bendamustine hydrochloride | 55.1 | 22.04 |
| Lactose anhydrous | 145.15 | 58.06 |
| Microcrystalline cellulose (Avicel ® PH112) | 31.25 | 12.50 |
| Ac-Di-Sol ® | 12.5 | 5.00 |
| Colloidal silicon dioxide (Aerosil ® 200) | 1.0 | 0.40 |
| Magnesium stearate | 2.5 | 1.00 |
| Ascorbic acid | 2.5 | 1.00 |

Tablets were stored at 40° C./75% RH (glass vial open) or 50° C. (glass vial closed). The amount of bendamustine hydrochloride and of related substances was measured with HPLC as mentioned above. The results are shown in Table 14b:

TABLE 14b

Related substances and assay of bendamustine HCl (residual content)

| Storage condition | Related substances | T = 0 | T = 1 month | Bendamustine HCl [% area] T = 0 | T = 1 month |
|---|---|---|---|---|---|
| 40° C./75% RH (open vial) | HP1 | 0.13 | 0.24 | 99.58 | 99.05 |
| | NP1 | 0.02 | 0.02 | | |
| | BM1Dimer | 0.06 | 0.27 | | |
| | BM1EE | 0.14 | 0.13 | | |
| | HP2 | n.d. | 0.13 | | |
| | HP3 | n.d. | 0.06 | | |
| 50° C. (closed vial) | HP1 | 0.13 | 0.63 | 99.58 | 98.32 |
| | NP1 | 0.02 | 0.02 | | |
| | BM1Dimer | 0.06 | 0.18 | | |
| | BM1EE | 0.14 | 0.12 | | |
| | HP2 | n.d. | n.d. | | |
| | HP3 | n.d. | n.d. | | |

PRIOR ART REFERENCE EXAMPLE 20.0±1 mg of bendamustine hydrochloride were weighed into the body of an empty hard gelatine capsule, and put into a clear glass HPLC vial (6 ml) of Agilent. Capsules were closed by placing the cap on top of the body and slight pushing. Capsules were stored at 40° C./75% RH (glass vial open) or 50° C. (glass vial closed). The amount of bendamustine hydrochloride and of related substances was measured with HPLC as mentioned above. The results are shown in Table 15:

TABLE 15

Related substances and assay of bendamustine HCl (residual content)

| Storage condition | Related substances | T = 0 | T = 1 month | Bendamustine HCl [% area] T = 0 | T = 1 month |
|---|---|---|---|---|---|
| 40° C./75% RH (open vial) | HP1 | 0.10 | 0.45 | 99.64 | 98.83 |
| | NP1 | 0.02 | 0.02 | | |
| | BM1Dimer | 0.06 | 0.42 | | |
| | BM1EE | 0.13 | 0.11 | | |

TABLE 15-continued

Related substances and assay of bendamustine HCl (residual content)

| Storage condition | Related substances | T = 0 | T = 1 month | Bendamustine HCl [% area] T = 0 | T = 1 month |
|---|---|---|---|---|---|
| | HP2 | n.d. | n.d. | | |
| | HP3 | n.d. | n.d. | | |
| 50° C. (closed vial) | HP1 | 0.10 | 1.46 | 99.64 | 97.51 |
| | NP1 | 0.02 | 0.02 | | |
| | BM1Dimer | 0.06 | 0.24 | | |
| | BM1EE | 0.13 | 0.12 | | |
| | HP2 | n.d. | n.d. | | |
| | HP3 | n.d. | n.d. | | |

As is immediately apparent, the capsule formulations were a lot less stable than the tablet formulations according to the invention although the capsule formulations were prepared from pure bendamustine hydrochloride without any further processing steps. Both at 40° C./75% RH (glass vial open) and 50° C. (closed vial) more degradation products are formed within one month of storage. In the case of open vial with 40° C. and 75% RH (relative humidity) the amount of hydrolysis product HP1 is increased by a factor of 4 after one month of storage. For the closed vials the HP1 content is even higher, which might be due to reaction with the capsules. Summarising, tablets provide a much more stable solid dosage form than the capsules.

Example 14

8.0 g of hydroxypropylmethyl cellulose and 1.5 g PEG 6000 are dissolved in 88.5 g purified water. Thereafter 2.0 g yellow ferric oxide and 0.5 g titanium oxide are dispersed therein yielding a coating liquid. Tablets as obtained in Example 11 are coated with 3% of this solution per tablet mass using a film coating device.

Example 15

TABLE 16a

| Coated Tablet Tablet cores | | |
|---|---|---|
| Component | mg/dosage-form | Relative Content % |
| bendamustine hydrochloride | 55.1 | 21.09 |
| Mannitol | 141.4 | 54.11 |
| Microcrystalline cellulose (Avicel ® PH101) | 25.0 | 9.57 |
| Crosscarmellose sodium (Ac-Di-Sol ®) | 12.5 | 4.78 |
| Colloidal silicon dioxide (Aerosil ® 200) | 1.0 | 0.38 |
| Talc | 18.8 | 7.19 |
| Stearic acid | 7.5 | 2.87 |
| Sum | 261.3 | 100 |
| Film-coating | | |
| Opadry ® | 12.5 | 10 |
| Purified water | — | 90 |
| Target mass gain (mg/tablet)/Sum | 12.5 | 100 |

Manufacturing Method for 1000 Tablets

All tablet-core components except for colloidal silicon dioxide and stearic acid were loaded into a Somakon vessel (5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the aforementioned conditions. Thereafter stearic acid was added and blending was continued for 1 minute. The blend was subsequently sieved through a 0.5 mm sieve, reloaded into the vessel and blended for another 30 seconds, all at the same conditions.

From this mixture round tablets were compressed having the following characteristics:

Mean value diameter: 9.5 mm; mean value mass: 254.6 mg (begin)–257.2 mg (end); friability 0.1%; mean value hardness: 122N (begin)–128 (end).

The tablets were subsequently film-coated with the Opadry® dispersion until a mass increase of 5% had been achieved.

The mean mass of the film-coated tablets was 268.4 mg.

Both the tablet cores and film-coated tablets were stored at 40° C./75% RH in closed amber glass vials. The amount of bendamustine hydrochloride as well as of related substances, like degradation products, by-products of synthesis were measured with HPLC as mentioned above. The results are shown in Tables 16b.1 and 16b.2.

TABLE 16b.1

Related substances and assay of bendamustine HCl (residual content) in tablet cores

| Storage condition | Related substances | Bendamustine HCl [% area] | | | |
|---|---|---|---|---|---|
| | | T = 0 | T = 2 months | T = 0 | T = 2 months |
| 40° C./75% RH (closed vials) | HP1 | 0.15 | 0.13 | 99.49 | 99.49 |
| | NP1 | n.d. | n.d. | | |
| | BM1Dimer | 0.09 | 0.17 | | |
| | BM1EE | 0.15 | 0.13 | | |
| | Unid RRT 0.69*[3] | 0.08 | 0.05 | | |

*[3]Unidentified compound peak at relative retention time of 0.69 as compared to main peak TABLE 16b.2

Related substances and assay of bendamustine HCl (residual content) in coated tablet

| Storage condition | Related substances | Bendamustine HCl [% area] | | | |
|---|---|---|---|---|---|
| | | T = 0 | T = 2 months | T = 0 | T = 2 months |
| 40° C./75% RH (closed vials) | HP1 | 0.16 | 0.17 | 99.46 | 99.29 |
| | HP2 | n.d. | 0.08 | | |
| | HP3 | n.d. | <0.05 | | |
| | NP1 | n.d. | n.d. | | |
| | BM1Dimer | 0.09 | 0.18 | | |
| | BM1EE | 0.15 | 0.14 | | |
| | Unid RRT 0.69 | 0.10 | 0.05 | | |

Example 16

TABLE 17a

Tablet Tablet cores

| Component | mg/dosage-form | Relative Content % |
|---|---|---|
| bendamustine hydrochloride | 55.1 | 21.09 |
| Lactose anhydrous | 141.4 | 54.11 |
| Microcrystalline cellulose (Avicel® PH112) | 25.0 | 9.57 |
| Crosscarmellose sodium (Ac-Di-Sol®) | 12.5 | 4.78 |
| Colloidal silicon dioxide (Aerosil® 200) | 1.0 | 0.38 |
| Talc | 18.8 | 7.19 |
| Stearic acid | 7.5 | 2.87 |
| Sum | 261.3 | 100 |
| Film-coating | | |
| Eudragit® E PO | 7.5 | 7.5 |
| Sodium laurylsulphate | 0.8 | 0.8 |
| Stearic acid | 1.2 | 1.2 |
| Iron oxide | 1.0 | 1.0 |
| Titanium dioxide | 1.0 | 1.0 |
| Talc | 3.5 | 3.5 |
| Purified water | — | 85.0 |
| Target mass gain (mg/tablet)/Sum | 15.0 | 100.0 |

Manufacturing Method for 1000 Tablets

All tablet-core components except for colloidal silicon dioxide and stearic acid were loaded into a Somakon vessel (5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the aforementioned conditions. Thereafter stearic acid was added and blending was continued for 1 minute. The blend was subsequently sieved through a 0.5 mm sieve, reloaded into the vessel and blended for another 30 seconds, all at the same conditions.

From this mixture round tablets were compressed having the following characteristics: mean value diameter: 9.5 mm; mean value mass: 262.4 mg (begin)–254.4 mg (end); friability: 0.1% (begin)–0.2% (end); mean hardness value: 98N (begin)–91N (end).

The tablets were subsequently film-coated with the Eudragit® dispersion until a mass increase of 3% had been achieved.

The mean mass of the film-coated tablets was 273.5 mg.

Both the tablet cores and the film-coated tablets were stored at 40° C./75% RH in closed amber glass vials. The amount of bendamustine hydrochloride and of related substances was measured with HPLC, as mentioned above. The results are shown in Tables 17b.1 and 17.b2:

TABLE 17b.1

Related substances and assay of bendamustine HCl (residual content) in tablet core

| Storage condition | Related substances | Bendamustine HCl [% area] | | | |
|---|---|---|---|---|---|
| | | T = 0 | T = 2 months | T = 0 | T = 2 months |
| 40° C./75% RH (closed vials) | HP1 | 0.17 | 0.12 | 99.50 | 99.55 |
| | NP1 | n.d. | n.d. | | |

TABLE 17b.1-continued

Related substances and assay of bendamustine
HCl (residual content) in tablet core

| Storage condition | Related substances | T = 0 | T = 2 months | T = 0 | T = 2 months |
|---|---|---|---|---|---|
| | | | Bendamustine HCl [% area] | | |
| | BM1Dimer | 0.09 | 0.14 | | |
| | BM1EE | 0.15 | 0.14 | | |
| | Unid RRT 0.69 | 0.06 | <0.05 | | |

TABLE 17b.2

Related substances and assay of bendamustine
HCl (residual content) in coated tablet

| Storage condition | Related substances | T = 0 | T = 2 months | T = 0 | T = 2 months |
|---|---|---|---|---|---|
| | | | Bendamustine HCl [% area] | | |
| 40° C./75% RH (closed vials) | HP1 | 0.18 | 0.20 | 99.43 | 98.93 |
| | HP2 | n.d. | 0.35 | | |
| | HP3 | n.d. | 0.07 | | |
| | NP1 | n.d. | n.d. | | |
| | BM1Dimer | 0.12 | 0.20 | | |
| | BM1EE | 0.15 | 0.13 | | |
| | Unid RRT 0.69 | 0.05 | <0.05 | | |

Example 17

TABLE 18a

| Tablet Tablet cores | | |
|---|---|---|
| Component | mg/dosage-form | Relative Content % |
| Bendamustine hydrochloride | 55.1 | 22.04 |
| Lactose anhydrous | 145.15 | 58.06 |
| Microcrystalline cellulose (Avicel ® PH112) | 31.25 | 12.50 |
| Ac-Di-Sol ® | 12.5 | 5.00 |
| Colloidal silicon dioxide (Aerosil ® 200) | 1.0 | 0.40 |
| Magnesium stearate | 2.5 | 1.00 |
| Ascorbic acid | 2.5 | 1.00 |
| Sum | 250 | 100.0 |
| Film-coating | | |
| Eudragit ® E PO | 7.5 | 7.5 |
| Sodium laurylsulphate | 0.8 | 0.8 |
| Stearic acid | 1.2 | 1.2 |
| Iron oxide | 1.0 | 1.0 |
| Titanium dioxide | 1.0 | 1.0 |
| Talc | 3.5 | 3.5 |
| Purified water | — | 85.0 |
| Target mass gain (mg/tablet)/Sum | 15.0 | 100.0 |

Manufacturing Method for 1000 Tablets

All tablet-core components except for colloidal silicon dioxide and stearic acid were loaded into a Somakon vessel (2.5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the afore-mentioned conditions. Thereafter stearic acid was added and blending was continued for 1 minute. The blend was subsequently sieved through a 0.5 mm sieve, reloaded into the vessel and blended for another 30 seconds, all at the same conditions.

From this mixture round tablets were compressed having the following characteristics: Mean value diameter: 9.5 mm; mean value mass: 252.2 mg (begin)–250.7 mg (end); friability: 0.1% (begin)–0.2% (end); mean hardness value: 65N (begin)–73N (end).

The tablets were subsequently film-coated with the Eudragit® dispersion until a mass increase of 3% had been achieved.

The mean mass of the film-coated tablets was 253.6 mg.

Both the tablet cores and the film-coated tablets were stored at 40° C./75% RH in closed amber glass vials. The amount of bendamustine hydrochloride and of related substances was measured with HPLC, as described above. The results are shown in Tables 18b.1 and 18b.2:

TABLE 18b.1

Related substances and assay of bendamustine
HCl (residual content) in tablet core

| Storage condition | Related substances | T = 0 | T = 2 months | T = 0 | T = 2 months |
|---|---|---|---|---|---|
| | | | Bendamustine HCl [% area] | | |
| 40° C./75% RH (closed vials) | HP1 | 0.17 | 0.14 | 99.47 | 99.45 |
| | HP3 | n.d. | 0.07 | | |
| | NP1 | n.d. | n.d. | | |
| | BM1Dimer | 0.10 | 0.19 | | |
| | BM1EE | 0.15 | 0.14 | | |
| | Unid RRT 0.69 | 0.05 | n.d. | | |

TABLE 18b.2

Related substances and assay of bendamustine
HCl (residual content) in coated tablet

| Storage condition | Related substances | T = 0 | T = 2 months | T = 0 | T = 2 months |
|---|---|---|---|---|---|
| | | | Bendamustine HCl [% area] | | |
| 40° C./75% RH (closed vials) | HP1 | 0.19 | 0.16 | 99.46 | 99.36 |
| | HP2 | n.d. | 0.06 | | |
| | HP3 | n.d. | 0.05 | | |
| | NP1 | n.d. | n.d. | | |
| | BM1Dimer | 0.09 | 0.18 | | |
| | BM1EE | 0.15 | 0.14 | | |
| | Unid RRT 0.69 | <0.05 | <0.05 | | |

Example 18

TABLE 9a

| | composition coated tablets | | |
|---|---|---|---|
| Composition component | PF1 mg/tablet | PF2 mg/tablet | PF3 mg/tablet |
| Bendamustine HCl | 55.1 | 55.1 | 55.1 |
| Anhydrous dextrose | — | — | 205.8 |
| Dextrose monohydrate | 186.0 | — | — |

TABLE 9a-continued composition coated tablets

| Composition component | PF1 mg/tablet | PF2 mg/tablet | PF3 mg/tablet |
|---|---|---|---|
| Trehalose | — | 66.0 | — |
| sorbitol | — | — | 43.9 |
| Lactose DCL 21 | 68.2 | 185.7 | — |
| Avicel ® PH 112 | 18.7 | — | 23.0 |
| Crospovidone | — | 21.0 | — |
| Magnesium stearate | 2.0 | 2.2 | 2.2 |
| Opadry | 8.0 | 8.0 | 8.0 |
| Total | 338.0 | 338.0 | 338.0 |

Manufacturing Method for Formulations PF1 for 600 Tablets:

33.06 g of bendamustine, 111.60 g of dextrose, 40.92 g of lactose, 11.22 g of microcrystalline cellulose and 1.20 g of magnesium stearate were weighed and transferred into a double polyethylene bag and mixed for 5 minutes. Thereafter the powder blend was transferred to the hopper of an eccentric tabletting machine (Korsch EK0) and compressed into round tablets having the following characteristics: mean value diameter: 10.0 mm; mean value mass: 336.9 mg (begin)–335.98 (end); friability: 0.15%; mean hardness value: 69.25N (begin)–68.60N (end).

The tablet cores were subsequently coated in a coating pan (4M8 ForMate PanCoat) using a 9% Opadry® TM White aqueous suspension and dried. The mean mass of the tablets was 342.42 mg. Thereafter the tablets were packed into amber glass bottles closed with screw plugs and stored at 40° C./75% RH.

Manufacturing Method for Formulations PF2 for 600 Tablets:

33.06 g of bendamustine, 111.42 g of lactose, 39.60 g of trehalose, 12.60 g of cross-linked polyvinylpyrrolidone and 1.32 g of magnesium stearate were weighed and transferred into a double polyethylene bag and mixed for 5 minutes. Thereafter the powder blend was transferred to the hopper of an eccentric tabletting machine (Korsch EK0) and compressed into round tablets having the following characteristics: mean value diameter: 10.0 mm; mean value mass: 332.95 mg (begin)–332.12 (end); friability: 0.3%; mean hardness value: 65.9 N (begin)–59.0 N (end).

The tablet cores were subsequently coated in a coating pan (4M8 ForMate PanCoat) using a 9% Opadry® TM White aqueous suspension and dried. The mean mass of the tablets was 340.1 mg. Thereafter the tablets were packed into amber glass bottles closed with screw plugs and stored at 40° C./75% RH.

Manufacturing Method for Formulation PF3:

Sorbitol and anhydrous dextrose were weighed. 140.64 g of Sorbitol was dissolved in 105.48 g of purified water and the solution obtained was subsequently used to granulate 659.36 g of dextrose in a Fluid Bed Granulator (4M8ForMate FluidBed). Thereafter the granulate was dried at 60° C. and sieved through a 850 μm sieve.

33.06 g of bendamustine hydrochloride, 149.82 g of the sorbitol/dextrose granulate, 13.8 g of microcrystalline cellulose and 1.32 g of magnesium stearate were weighed into a double polyethylene bag and mixed for 5 minutes. Thereafter the powder blend was transferred to the hopper of an eccentric tabletting machine (Korsch EK0O and compressed into round tablets having a mean diameter of 10.0 mm. The tablets had a mean value for mass of 335.99 mg (begin)–339.50 mg (end); friability: 0%; mean hardness value: 125.60N (begin)–129.7N (end). The tablets were then subjected to a conditioning process according to the following two steps (performed only on selected batches): placing them at 25° C./60% R.H. for two hours and subsequently at 40° C. for two hours.

The tablets were subsequently coated in a coating pan (4M8 ForMate PanCoat) using a 9% Opadry® TM White aqueous suspension. Mean mass of the tablets: 341.43 mg. Thereafter the tablets were packed into amber glass bottles closed with screw plugs and stored at 40° C./75% RH.

The amount of bendamustine hydrochloride and of related substances in the stored film-coated tablets was measured with HPLC, as described above. The results are shown in Tables 19b.1-19b.3:

TABLE 19b.1

Related substances and assay of bendamustine HCl (residual content) in coated tablet (formulation 1; Opadry ®) PF1

| Storage condition | Related substances | T = 0 | T = 3 months | Bendamustine HCl [% area] T = 0 | T = 3 months |
|---|---|---|---|---|---|
| 40° C./75% RH (closed vials) | HP1 | 0.03 | 0.08 | 99.5 | 98.7 |
| | NP1 | n.d. | n.d. | | |
| | BM1Dimer | 0.05 | 0.16 | | |
| | BM1EE | 0.15 | 0.13 | | |
| | Individual unknown impurity | 0.01 | 0.06 | | |

TABLE 19b.2

Related substances and assay of bendamustine HCl (residual content) in coated tablet (formulation 2; Opadry ®) PF2

| Storage condition | Related substances | T = 0 | T = 3 months | Bendamustine HCl [% area] T = 0 | T = 3 months |
|---|---|---|---|---|---|
| 40° C./75% RH (closed vials) | HP1 | 0.02 | 0.23 | 98.5 | 98.3 |
| | NP1 | 0.01 | 0.01 | | |
| | BM1Dimer | 0.03 | 0.23 | | |
| | BM1EE | 0.15 | 0.11 | | |
| | Individual unknown impurity | 0.01 | 0.05 | | |

TABLE 19b.3

Related substances and assay of bendamustine HCl (residual content) in coated tablet (formulation 3; Opadry ®) PF3

| Storage condition | Related substances | T = 0 | T = 3 months | Bendamustine HCl [% area] T = 0 | T = 3 months |
|---|---|---|---|---|---|
| 40° C./75% RH (closed vials) | HP1 | 0.05 | 0.09 | 98.1 | 98.4 |
| | NP1 | n.d. | n.d. | | |
| | BM1Dimer | 0.06 | 0.19 | | |
| | BM1EE | 0.15 | 0.14 | | |
| | Individual unknown impurity | 0.03 | 0.11 | | |

3. Dissolution Tests

Example 19

Dissolution tests for the tablet formulations of Examples 11 and 12 were carried out in artificial gastric fluid at T=0. The dissolution samples are tested for assay by HPLC (column: Zorbax Bonus-RP, 5 μm; temperature of column oven: 30° C.; temperature of autosampler: 5° C.; detector: 254 nm). Artificial gastric fluid pH 1.5 was prepared by dissolving 2 g of sodium chloride p.A. in 1000 ml of water and adjusting the pH to 1.5±0.05 with 5 N hydrochloric acid. The dissolution test was conducted according to Chapter 2.9.3. of European Pharmacopoeia 6.0, using Apparatus 2 (Paddle-apparatus). The rotation speed of the paddle was 50 rpm, the temperature was 37° C.±0.5° C., the amount of dissolution medium was 500 ml.

The results for the tablet formulations of Example 11 (tablet formulation 1) and Example 12 (tablet formulation 2) are shown in the following Table 20a:

TABLE 20.a

| Dissolution after: | Tablet formulation 1 Dissolution Single value [%] | Tablet formulation 1 Dissolution Mean value [%] | Tablet formulation 2 Dissolution: Single value [%] | Tablet formulation 2 Dissolution: Mean value [%] |
|---|---|---|---|---|
| 10 min | 85.3 | 84 | 80.9 | 88 |
|  | 77.4 |  | 87.8 |  |
|  | 87.2 |  | 88.7 |  |
|  | 90.6 |  | 94.3 |  |
|  | 79.6 |  | 87.9 |  |
|  | 84.1 |  | 90.8 |  |
| 20 min | 94.7 | 95 | 96.5 | 96 |
|  | 95.7 |  | 98.7 |  |
|  | 96.6 |  | 95.7 |  |
|  | 96.4 |  | 94.3 |  |
|  | 93.0 |  | 93.8 |  |
|  | 93.9 |  | 97.0 |  |
| 30 min | 93.3 | 94 | 95.3 | 95 |
|  | 94.3 |  | 96.4 |  |
|  | 95.4 |  | 94.4 |  |
|  | 95.4 |  | 93.1 |  |
|  | 91.8 |  | 92.9 |  |
|  | 93.0 |  | 95.3 |  |

The results of the same dissolution tests carried out on the coated tablet formulations of Example 15, Example 16 and Example 17 at T=0 are shown in the following Table 20b:

TABLE 20b

| Dissolution after | Tablet formulation example 15 Mean value | Tablet formulation example 16 Mean value | Tablet formulation example 17 Mean value |
|---|---|---|---|
| 10 minutes | 77 | 47 | 83 |
| 20 minutes | 88 | 76 | 90 |
| 30 minutes | 87 | 87 | 88 |

Corresponding dissolution data for the tablets of example 18 were:

| Dissolution after | Tablet formulation example 18 (PF1) Mean value after 3 months at 40° C./ 75% RH | Tablet formulation example 18 (PF2) Mean value after 3 months at 40° C./ 75% RH | Tablet formulation example 18 (PF3) Mean value after 3 months storage at 40° C./ 75% RH |
|---|---|---|---|
| 10 minutes | 89.7 | 96.3 | 60.1 |
| 20 minutes | 93.7 | 95.2 | 88.8 |
| 30 minutes | 93.2 | 93.3 | 94.0 |

As may be taken from the above all tablet formulations of the invention show a fast dissolution of bendamustine. In particular the inventive formulations show a dissolution profile of the bendamustine as defined hereinbefore.

4. In Vivo Tests

Animal Bioavailability Studies of Bendamustine were Performed in Beagle Dogs: PK Study Outlines Study 1

The objective was to determine the bioavailability of 1 dose (i.e. 50 mg) of bendamustine in 3 tablet formulations (T1-3) and 1 capsule formulation (C) with a total of 4 oral formulations: AUC and Cmax
Total number of animals required: 16
Basic Design:
Cross-over design, 8 animals per arm:

TABLE 21a

Period 1 (single dose of tablet, or capsule, day 1):

| Group | Treatment | Dose route | Dose # (mg) | Number of animals | Animal numbers |
|---|---|---|---|---|---|
| 1 | Bendamustine | Capsule | 50 | 2 Male + 2 Female | 37, 39 38, 40 |
| 2 | Bendamustine | Tablet T1 | 50 | 2 Male + 2 Female | 41, 43 42, 44 |
| 3 | Bendamustine | Capsule | 50 | 1 Male + 1 Female | 45 46 |
| 4 | Bendamustine | Tablet T2 | 50 | 2 Male + 1 Female | 47, 49 48 |
| 5 | Bendamustine | Tablet T3 | 50 | 1 Male + 2 Female | 51 50, 52 |

One week wash-out

TABLE 21b

Period 2 (1 week after period 1, single dose of any of the following, day 8):

| Group | Treatment | Dose route | Dose # (mg) | Number of animals | Animal numbers |
|---|---|---|---|---|---|
| 1 | Bendamustine | Tablet T1 | 50 | 2 Male + 2 Female | 37, 39 38, 40 |
| 2 | Bendamustine | Capsule | 50 | 2 Male + 2 Female | 41, 43 42, 44 |
| 3 | Bendamustine | Tablet T3 | 50 | 1 Male + 1 Female | 45 46 |
| 4 | Bendamustine | Capsule | 50 | 2 Male + 1 Female | 47, 49 48 |
| 5 | Bendamustine | Tablet T2 | 50 | 1 Male + 2 Female | 51 50, 52 |

One Week Wash-Out

TABLE 21c

| | | Period 3 (1 week after period 2, single dose of any of the following, day 15): | | | |
|---|---|---|---|---|---|
| Group | Treatment | Dose route | Dose # (mg) | Number of animals | Animal numbers |
| 3 | Bendamustine | Tablet T2 | 50 | 1 Male + 1 Female | 45 46 |
| 4 | Bendamustine | Tablet T3 | 50 | 2 Male + 1 Female | 47, 49 48 |
| 5 | Bendamustine | Capsule | 50 | 1 Male + 2 Female | 51 50, 52 |

Study 2

The objective was to determine the bioavailability of 1 dose (i.e. 50 mg) of bendamustine in 1 tablet formulation T4, and 1 capsule formulation (C) with a total of 3 oral formulations: AUC and Cmax Total number of animals required: 16

Basic Design:
Cross-over design, 8 animals per arm:

TABLE 22a

| | | Period 1 (single dose of capsule, day 1): | | | |
|---|---|---|---|---|---|
| Group | Treatment | Dose | Dose # (mg) | Number of animals | Animal numbers |
| 1 | Bendamustine | Capsule | 50 | 4 Male + 4 Female | |
| 2 | Bendamustine | Capsule | 50 | 4 Male + 4 Female | |

One week wash-out

TABLE 22b

| | | Period 2 (1 week after period 1, single dose of either of the following formulations, day 8): | | | |
|---|---|---|---|---|---|
| Group | Treatment | Dose route | Dose # (mg) | Number of animals | Animal numbers |
| 1 | Bendamustine | Formulation X | 50 | 4 Male + 4 Female | |
| 2 | Bendamustine | T4 | 50 | 4 Male + 4 Female | |

Example 20

The coated tablets of Example 18 (formulation 3, coated with Opadry® Tablets T4), containing 50 mg of bendamustine, were orally administered to male and female dogs in comparison with the capsules of the reference example.

Figure 3:
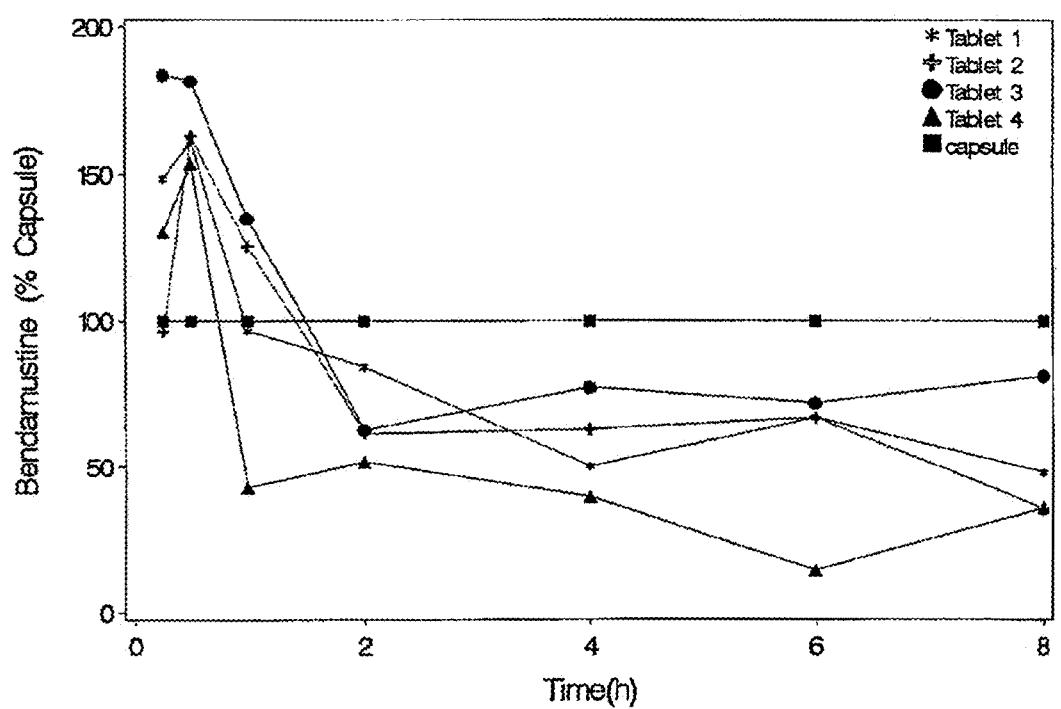
FIG. 3 shows the mean plasma concentration (tablets versus capsule) vs. time curve obtained after administering bendamustine hydrochloride in the form of prior art capsules and the tablet formulations of Examples 15 to 17 (Tablets 1-3) and example 18 (formulation 3) (Tablet 4) to dogs. It is apparent from FIG. 3 that the tablet formulations provide for higher maximum concentrations of bendamustine, as compared to the prior art capsule.

The mean plasma profiles vs. time for both the capsule formulation and the coated tablet of Example 18 are shown in FIG. 3.

Example 21

The coated tablets of Examples 15, 16, or 17 (Tablets T1 to T3), containing 50 mg of bendamustine, were orally administered to male and female dogs in comparison with the capsules of the reference example.

The mean plasma profiles vs. time of the capsule formulation and the coated tablets of Examples 15 to 17 are shown in FIG. 3.

Experiments were conducted in order to:
assess which saccharides or saccharide mixtures are suitable to obtain chemically stable tablets, with fast dissolution profile and hardness values suitable for coating;
evaluate the compatibility between API and excipients;
develop placebo and API-containing batches by investigating different manufacturing processes: dry granulation, direct compression and wet granulation;
evaluate different bendamustine hydrochloride/saccharide weight ratios;
evaluate the impact of saccharide purity on the formation of bendamustine hydrochloride purities;
investigate the influence of moisture content on the technological properties and stability of the manufactured tablets;
manufacture tablets using the commercially available freeze dried bendamustine hydrochloride product (Ribomustin®) and to compare the properties of these tablets with tablets produced using corresponding amounts of mannitol and bendamustine hydrochloride.

The following saccharidests were used for the manufacturing of tablets in accordance with the invention, the tablets containing 50 mg of bendamustine (55 mg as bendamustine hydrochloride)

TABLE 23

| Chemical name | Product name/ Manufacturer | Class |
|---|---|---|
| Dextrose anhydrous | Dextrose anhydrous C/Roquette | Monosaccharide |
| Dextrose anhydrous | Dextrose anhydrous ST 0.5/Roquette | Monosaccharide |
| Dextrose monohydrate | Dextrose monohydrate G/Roquette | Monosaccharide |
| Dextrose monohydrate | Dextrose monohydrate M/Roquette | Monosaccharide |
| Lactitol monohydrate | Lacty-M/Purac Biochem Lactitol MC/Danisco | Disaccharide |
| Trehalose | Treha 16400/Cargill | Disaccharide |
| Sorbitol | Neosorb P6OW/Roquette | Monosaccharide |
| Erythritol | Zerose (TM) Erythritol 16954/Cargill | Monosaccharide |
| Maltose Monohydrate | Sunmalt S/Hayashibara | Disaccharide |
| Mannitol | Pearlitol 200 SD/Roquette | Monosaccharide |
| Lactose anhydrous | SuperTab 21 AN/DMV-Fonterra Excipients | Disaccharide |
| Lactose monohydrate | SuperTab 14 SD/DMV-Fonterra Excipients | Disaccharide |
| Fructose | Fructose MS/Galam | Monosaccharide |
| Maltitol | Sweetpearl P200/Roquette | Disaccharide |
| Xylitol | Xylisorb 300/Roquette | Monosaccharide |
| Sucrose | Sucrose Comprizucker S/Suedzucker | Disaccharide |
| Sucrose | Sucrose RFS/Suedzucker | Disaccharide |
| Sucrose 97% + Maltodextrin 3% | EV saccharide DC 3, 75 MD/Vibar Nord SPA | Disaccharide |
| β-Cyclodextrin | Kleptose DC/Roquette | Cyclic eptasaccharide |
| D-Raffinose Pentahydrate | n/a/Senn Chemicals | Trisaccharide |
| D-Melezitose monohydrate | n/a/Biosynth | Trisaccharide |
| Microcrystalline Cellulose | Avicel PH112/FMC Biopolymer | Polysaccharide |
| Microcrystalline Cellulose | Avicel pH101/FMC Biopolymer | Polysaccharide |

The quality of the batches made was assessed by observation of the physical appearance, identification test (HPLC), dissolution test, content and related substances assay (HPLC), content uniformity test (HPLC), hardness test and water content (Karl Fischer method). Batches were submitted to accelerated stability studies packaged in amber glass bottles under the storage conditions detailed in the following table. For each manufactured API-containing batch some tablets were stored at 5° C. as back-up samples.

In the following, the various excipients in relation to their manufacturing process were investigated. By using these excipients several placebo manufacturing trials were carried out by dry granulation to obtain preliminary information about the manufacturing method suitable to obtain tablets with good quality.

Two types of disintegrants were used: microcrystalline cellulose (Avicel®PH 112), as a standard disintegrant, and cross-linked polyvinylpyrrolidone (Crospovidone®), used just for batch D001T/002. The choice of Crospovidone® for batch D001T/002 (filler: anhydrous lactose) was based on the similarity between this formulation and the prototype formulation of example 9. Magnesium stearate was used as lubricant for all the batches produced.he dry granulation manufacturing process for placebo trials consisted in the following steps:

1. The saccharide and a partial quantity of lubricant (83.3% w/w of the total amount) were accurately weighed and then mixed in a polyethylene bag for 2 minutes.
2. The obtained mixture was compacted by using the tabletting machine equipped with a 18 mm diameter punch.
3. The obtained slugs were sieved by using a 850 micron net.
4. The granulate was weighed and mixed with the disintegrant and the remaining amount of the lubricant (16.7% w/w) in a polyethylene bag for 2 minutes and then tabletted by using a 10 mm diameter punch.

Table 24 and Table 25 summarize the composition of each Placebo formulation and the results of the analytical tests performed on both the final mixtures and the tablets.

In Table 16, observations made during the manufacturing process of placebo batches and/or during their analytical characterization are reported.

The analytical and physical test results carried out on placebo batches D001T/001-D001T/002-D001T/004-D001T/013-D001T/015 showed that these formulations are suitable to be manufactured by dry granulation and further investigated by the addition of the API. All the other formulations are characterized by a powder difficult to compact and, when obtained, tablets with high friability.

Batch D001T/005 (filler: β-cyclodextrin) showed good behaviour in dry manufacturing process, high hardness, low friability but long disintegration time. This formulation was further investigated by employing a super disintegrant (Crospovidone®) and adding the API (see following paragraph).

TABLE 24

Dry granulation—Placebo batches composition and analytical results (batches D001T/001 ÷ D001T/010).

| Components | D001T/001 (%w/w) | D001T/002 (%w/w) | D001T/003 (%w/w) | D001T/004 (%w/w) | D001T/005 (%w/w) | D001T/006 (%w/w) | D001T/007 (%w/w) | D001T/008 (%w/w) | D001T/009 (%w/w) | D001T/010 (%w/w) |
|---|---|---|---|---|---|---|---|---|---|---|
| Lactose Monohydrate (SuperTab 14 SD) | 93.7 | — | — | — | — | — | — | — | — | — |
| Lactose Anhydrous (SuperTab 21 AN) | — | 93.7 | — | — | — | — | — | — | — | — |
| Mannitol (Pearlitol 200 SD) | — | — | 93.7 | — | — | — | — | — | — | — |
| Sorbitol (Neosorb P60W) | — | — | — | 93.7 | — | — | — | — | — | — |
| β-Cyclodextrin (Kleptose DC) | — | — | — | — | 93.7 | — | — | — | — | — |
| Dextrose Anhydrous (Dextrose Anhydrous C) | — | — | — | — | — | 93.7 | — | — | — | — |
| Dextrose Monohydrate (Dextrose Monohydrate G) | — | — | — | — | — | — | 93.7 | — | — | — |
| D-Raffinose Pentahydrate | — | — | — | — | — | — | — | 93.7 | — | — |
| Trehalose (Treha 16400) | — | — | — | — | — | — | — | — | 93.7 | — |
| Erythritol (Zerose Erythritol 16954) | — | — | — | — | — | — | — | — | — | 99.5 |
| Avicel PH 112 | 5.7 | — | 5.7 | 5.7 | 5.7 | 5.7 | 5.7 | 5.7 | 5.7 | — |
| Crospovidone | — | 5.7 | — | — | — | — | — | — | — | — |
| Magnesium Stearate | 0.6 | 0.6 | 0.6 | 0.6 | 0.6 | 0.6 | 0.6 | 0.6 | 0.6 | 0.5 |
| Results of analytical tests performed on final mixtures | | | | | | | | | | |
| Water Content (%) | 5.26 | 0.85 | 0.47 | 0.93 | 12.62 | 0.47 | 8.47 | 14.59 | 9.36 | N.A. |
| Flowability (seconds) | 24.68 (Nozzle 1, | 4.66 (Nozzle 3, | 9.91 (Nozzle 2, | 13.70 (Nozzle 1, | 15.61 (Nozzle 1, | 27.70 (Nozzle 1, | 25.37 (Nozzle 1, | 19.43 (Nozzle 1, | 20.85 (Nozzle 1, | N.A. |

TABLE 24-continued

Dry granulation—Placebo batches composition and analytical results (batches D001T/001 ÷ D001T/010).

Placebo Batches manufactured by Dry Granulation

| Components | D001T/001 (%w/w) | D001T/002 (%w/w) | D001T/003 (%w/w) | D001T/004 (%w/w) | D001T/005 (%w/w) | D001T/006 (%w/w) | D001T/007 (%w/w) | D001T/008 (%w/w) | D001T/009 (%w/w) | D001T/010 (%w/w) |
|---|---|---|---|---|---|---|---|---|---|---|
| (Test performed according to EP 6.0, par. 2.9.16) | diameter = 10.0 mm) | diameter = 25.0 mm) | diameter = 15.0 mm) | diameter = 10.0 mm) | diameter = 10.0 mm) | diameter = 10.0 mm) | diameter = 10.0 mm) | diameter = 10.0 mm) | diameter = 10.0 mm) | diameter = 10.0 mm) |
| Results of analytical tests performed on tablets | | | | | | | | | | |
| Hardness (N) | 70 | 99 | 86 | 148 | 127 | N.A. | 54 | 46 | 61 | N.A. |
| Friability (%) (Test performed according to EP 6.0, par. 2.9.7) | 0.1 | 0.1 | 0.6 | 0.2 | 0.2 | N.A. | Test failure (39.4) | Test failure (31.7) | Test failure (44.9) | N.A. |
| Mean Weight (mg/tablet) | 360 | 365 | 319 | 332 | 327 | N.A | 365 | 337 | 335 | N.A. |
| Disintegration (min.sec) (medium: buffer pH = 1.5) | 5'07" | 1'24" | 2'51" | 4'56" | 20'59" | N.A. | 4'18" | 1'22" | 3'59" | N.A. |

N.A. = not available because the mixture is not suitable for tabletting process (see the observations reported in table 5a)

TABLE 25

Dry granulation—Placebo batches composition and analytical results (batches D001T/011 ÷ D001T/025).

Placebo Batches manufactured by Dry Granulation

| Components | D001T/011 (%w/w) | D001T/012 (%w/w) | D001T/013 (%w/w) | D001T/014 (%w/w) | D001T/015 (%w/w) | D001T/016 (%w/w) | D001T/017 (%w/w) | D001T/018 (%w/w) | D001T/019 (%w/w) | D001T/025 (%w/w) |
|---|---|---|---|---|---|---|---|---|---|---|
| Fructose (Fructose MS) | 93.7 | — | — | — | — | — | — | — | — | — |
| Maltitol (Sweetpearl P200) | — | 93.7 | — | — | — | — | — | — | — | — |
| Maltose Monohydrate (Sunmalt S) | — | — | 93.7 | — | — | — | — | — | — | — |
| Lactitol Monohydrate (Lacty M) | — | — | — | 93.7 | — | — | — | — | — | — |
| Sucrose 97% + Maltodextrin 3% (EV Saccharide DC 3.75 MD) | — | — | — | — | 93.7 | — | — | — | — | — |
| Sucrose (Sucrose Comprizucker S) | — | — | — | — | — | 99.5 | — | — | — | — |
| Sucrose (Sucrose granular RFS) | — | — | — | — | — | — | 93.7 | — | — | — |
| Xylitol (Xylisorb 300) | — | — | — | — | — | — | — | 99.5 | — | — |
| β-Cyclodextrin (Kleptose DC) | — | — | — | — | — | — | — | — | 93.8 | — |
| D-Melezitose monohydrate | — | — | — | — | — | — | — | — | — | 93.8 |
| Avicel PH 112 | — | 5.7 | 5.7 | 5.7 | 5.7 | — | 5.7 | — | — | — |
| Crospovidone | 5.7 | — | — | — | — | — | — | — | 5.6 | 5.6 |
| Magnesium Stearate | 0.6 | 0.6 | 0.6 | 0.6 | 0.6 | 0.5 | 0.6 | 0.5 | 0.6 | 0.6 |
| Results of analytical tests performed on final mixtures | | | | | | | | | | |
| Water Content (%) | 0.42 | 0.38 | 5.71 | 5.45 | 0.78 | N/A | 0.32 | N/A | 12.30 | Not flow |
| Flowability (seconds) (Test performed according to EP 6.0, par. 2.9.16) | 19.09 (Nozzle 1, diameter = 10.0 mm) | 22.54 (Nozzle 1, diameter = 10.0 mm) | 16.57 (Nozzle 1, diameter = 10.0 mm) | 23.41 (Nozzle 1, diameter = 10.0 mm) | 5.37 (Nozzle 3, diameter = 25.0 mm) | N/A | 17.38 (Nozzle 1, diameter = 10.0 mm) | N/A | 18.64 (Nozzle 1, diameter = 10.0 mm) | (Nozzle 3, diameter = 25.0 mm) |
| Results of analytical tests performed on tablets | | | | | | | | | | |
| Hardness (N) | 17 | 33 | 130 | 69 | 69 | N/A | 19 | N/A | 62 | 56 |
| Friability (%) (Test performed | Test failure | Test failure | 0.2 | Test failure | 0.4 | N/A | Test failure | N/A | 0.2 | Test failure |

TABLE 25-continued

Dry granulation—Placebo batches composition and analytical results (batches D001T/011÷D001T/025).

| | Placebo Batches manufactured by Dry Granulation | | | | | | | | | |
|---|---|---|---|---|---|---|---|---|---|---|
| Components | D001T/011 (%w/w) | D001T/012 (%w/w) | D001T/013 (%w/w) | D001T/014 (%w/w) | D001T/015 (%w/w) | D001T/016 (%w/w) | D001T/017 (%w/w) | D001T/018 (%w/w) | D001T/019 (%w/w) | D001T/025 (%w/w) |
| according to EP 6.0, par. 2.9.7) | (100.0) | (100.0) | | (19.6) | | | (78.0) | | | (20.7) |
| Mean Weight (mg/tablet) | 380 | 388 | 328 | 338 | 349 | N/A | 383 | N/A | 338 | 328 |
| Disintegration (min.) (medium: buffer pH = 1.5) | 5'52" | 6'40" | 5'09" | 6'32" | 5'47" | N/A | 4'50" | N/A | 4'01" | 3'30" |

N/A = not available because the mixture is not suitable for tabletting process (see the observations reported in table 5a)

TABLE 26

Observations about manufacturing process, product technological properties and analytical tests for each manufactured placebo batch

| Placebo Batches | Dry Granulation process/obtained slugs | Tabletting Process/obtained tablets | Analytical tests on tablets |
|---|---|---|---|
| D001T/001 | Excellent slugs; easy to be sieved | Easy to be tabletted; good tablets obtained | Fast disintegration; low friability; medium hardness |
| D001T/002 | Good slugs; easy to be sieved | Easy to be tabletted; good tablets obtained | Fast disintegration; low friability; high hardness |
| D001T/003 | Difficult to compact; high pressure needed to obtain slugs | Difficult to be tabletted; The powder adheres to punches; tabletting process was interrupted after a few tablets | Fast disintegration; high friability; high hardness |
| D001T/004 | Excellent slugs; easy to be sieved | Fairly good to be tabletted; good tablets obtained | Fast disintegration; low friability; very high hardness |
| D001T/005 | Excellent slugs; easy to be sieved | Easy to be tabletted; good tablets obtained | Slow disintegration; low friability; high hardness |
| D001T/006 | Poor slugs, high friability | Impossible to be tabletted; tabletting process interrupted | No tablets available for analytical testing |
| D001T/007 | Poor slugs, high friability | Good to be tabletted; fairly good tablets obtained | Fast disintegration; very high friability, above acceptance limit; medium hardness |
| D001T/008 | Poor slugs, high friability | Good to be tabletted; fairly good tablets obtained | Fast disintegration; very high friability, above acceptance limit; medium hardness |
| D001T/009 | Good slugs; easy to be sieved | Good to be tabletted; fairly good tablets obtained | Fast disintegration; very high friability, above acceptance limit; medium hardness |
| D001T/010 | Impossible to obtain slugs; not further processed | — | — |
| D001T/011 | Poor slugs, high friability | Poor tablets obtained (many tablets break during tabletting process) | Fast disintegration; very high friability, above acceptance limit (all tablets broken after test); very low hardness |
| D001T/012 | Poor slugs, high friability | Poor tablets obtained (many tablets break during tabletting process) | Fast disintegration; very high friability, above acceptance limit (all tablets broken after test); low hardness |
| D001T/013 | Excellent slugs; easy to be sieved | Easy to be tabletted; good tablets obtained | Fast disintegration; low friability; very high hardness |
| D001T/014 | Good slugs; easy to be sieved | Good to be tabletted; fairly good tablets obtained | Fast disintegration; high friability, above acceptance limit; medium hardness |
| D001T/015 | Good slugs; easy to be sieved | Good to be tabletted; good tablets obtained | Fast disintegration; medium friability; medium hardness |
| D001T/016 | Impossible to obtain slugs; not further processed | — | — |
| D001T/017 | Poor slugs, high friability | Poor tablets obtained (many tablets break during tabletting process) | Fast disintegration; high friability, above acceptance limit; low hardness |
| D001T/018 | Impossible to obtain slugs; not further processed | — | — |
| D001T/019 | Excellent slugs; easy to be sieved | Easy to be tabletted; good tablets obtained | Fast disintegration; low friability; medium hardness |
| D001T/025 | Good slugs; easy to be sieved | Good to be tabletted; fairly good tablets obtained | Fast disintegration; very high friability, above acceptance limit; medium hardness |

Batches Manufactured by Dry Granulation with a 1:5 Bendamustine Hydrochloride/Saccharide Weight Ratio The placebo formulations, evaluated as more suitable to manufacture tablets containing the active pharmaceutical ingredient (API) by dry granulation, were modified to include the API and two API/saccharide weight ratios were explored: 1:5 and 1:2.

In this paragraph, formulations with a 1:5 API/saccharideweight ratios are described.

Two types of disintegrant were used: microcrystalline cellulose (Avicel®PH 112), as a standard disintegrant, and crosslinked polyvivylpyrrolidone (Crospovidone), used just for the batch D001T/022. Magnesium stearate was used as lubricant for all the batches produced.

The manufacturing process of the API-containing batches by dry granulation consisted in the following steps:
1. The saccharide, a partial quantity of lubricant (83.3% w/w of the total amount) and Bendamustine Hydrochloride were accurately weighed and mixed in a double polyethylene bag for 5 minutes.
2. The powder blend was pressed by using the tabletting machine equipped with 18 mm diameter punch.
3. To obtain a granulate, the produced slugs were sieved by using a 850 micron net.
4. The granulate was weighed and mixed with the disintegrant and the remaining amount of the lubricant (16.7 in a double polyethylene bag for 5 minutes.
5. The obtained mixture was tabletted by using a 10 mm diameter punch.

Table 27 summarizes the composition of each API-containing formulation manufactured and the results of the analytical tests performed on the API-containing final mixtures; table 28 summarizes the results of the analytical tests performed on the obtained products.

TABLE 27

Dry granulation—API/Saccharide weight ratio 1:5. API-containing batches final mixture composition and analytical results.

| Components | API-containing batches manufactured by Dry granulation API/Saccharide ratio 1:5 | | | | |
|---|---|---|---|---|---|
| | D001T/020 (% w/w) | D001T/021 (% w/w) | D001T/022 (% w/w) | D001T/023 (% w/w) | D001T/024 (% w/w) |
| Bendamustine HCL | 15.3 | 16.6 | 16.6 | 16.6 | 15.7 |
| Lactose Monohydrate (SuperTab 14 SD) | 78.4 | — | — | — | — |
| Sorbitol (Neosorb P60W) | — | 77.1 | — | — | — |
| β-Cyclodextrin (Kleptose DC) | — | — | 77.1 | — | — |
| Maltose (Food grade) (Sunmalt S) | — | — | — | 77.1 | — |
| Sucrose 97% + Maltodextrin 3%) (EV Saccharide DC 3.75 MD). | — | — | — | — | 78.0 |
| Avicel PH 112 | 5.7 | 5.7 | — | 5.7 | 5.7 |
| Crospovidone | — | — | 5.7 | — | — |
| Magnesium Stearate | 0.6 | 0.6 | 0.6 | 0.6 | 0.6 |
| | Result of analytical tests performed on final mixture | | | | |
| Flowability (seconds) (Test performed according to EP 6.0, par. 2.9.16) | 7.31 (Nozzle 2, diameter = 15 mm) | 19.91 (Nozzle 1, diameter = 10 mm) | 3.89 (Nozzle 3, diameter = 25 mm) | 23.00 (Nozzle 1, diameter = 10 mm) | 7.99 (Nozzle 3, diameter = 25 mm) |

TABLE 28

Dry granulation—API//Saccharide weight ratio 1:5. API—containing batches tablets analytical results.

| Analytical Test | Specification Limits | Results of analytical tests performed on tablets | | | | |
|---|---|---|---|---|---|---|
| | | D001T/020 | D001T/021 | D001T/022 | D001T/023 | D001T/024 |
| Identification (HPLC) | Positive | Positive | Positive | Positive | Positive | Positive |
| Mean Weight (mg/tablet) | Specific for each formulation | 359.43 Limits: 342 ÷ 378 | 336.27 Limits: 315.4 ÷ 348.6 | 334.67 Limits: 315.4 ÷ 348.6 | 333.19 Limits: 315.4 ÷ 348.6 | 349.72 Limits: 332.5 ÷ 367.5 |
| Content Uniformity (Test performed according to EP 6.0) | Complies | Complies RSD 1.26 | Complies RSD 1.42 | Complies RSD 0.84 | Complies RSD 0.58 | Complies RSD 2.02 |
| Assay (%) (HPLC) | 95.0%-105.0% | 96.9 | 93.5 | 97.4 | 93.8 | 97.7 |
| Related substances (%) | | | | | | |
| (HPLC) | ≤0.5% | 0.12 | 0.10 | 0.08 | 0.11 | 0.14 |
| HP1 | ≤0.2% | 0.04 | 0.05 | 0.05 | 0.05 | 0.04 |

TABLE 28-continued

Dry granulation—API//Saccharide weight ratio 1:5. API—containing batches tablets analytical results.

| Analytical Test | Specification Limits | Results of analytical tests performed on tablets | | | | |
|---|---|---|---|---|---|---|
| | | D001T/020 | D001T/021 | D001T/022 | D001T/023 | D001T/024 |
| BM1 Dimer | ≤0.5% | 0.14 | 0.13 | 0.13 | 0.13 | 0.15 |
| BM1EE | | | | | | |
| NP1 | ≤0.2% | n.d. | n.d. | 0.01 | n.d. | 0.1 |
| Individual unknown impurity | ≤0.1% | 0.01 | n.d. | n.d. | n.d. | n.d. |
| Total impurities | ≤1.5% | 0.31 | 0.28 | 0.27 | 0.29 | 0.34 |
| Dissolution Test | | | | | | |
| (Medium: buffer pH-1.5) | | | | | | |
| (% 10 min) | 80% in 30 | 72.9 | 72.1 | 88.0 | 60.0 | 75.5 |
| (% 20 min) | minutes | 87.6 | 85.9 | 88.9 | 79.2 | 89.6 |
| (% 30 min) | | 87.2 | 84.7 | 87.4 | 84.7 | 90.3 |
| Moisture content (%) | — | 4.72 | 1.00 | 11.3 | 5.13 | 0.88 |
| Hardness (A) | ≥40 N | 67 | 89 | 77 | 151 | 55 |
| Friability (%) | | | | | | |
| (Test performed according to EP 6.0, par. 2.9.7) | ≤1.0% | 0.2 | 0.2 | 0.1 | 0.2 | 0.4 |

The results of analytical tests performed both on final mixtures and finished products were in most cases good, mainly for Content Uniformity and Purity. All API-containing batches showed satisfactory mass uniformity, homogeneity of API content, and a low impurities content. The impurity profile of all formulations was in compliance with the specifications of API (see specification limits in the tables), thus no degradation occurs during manufacturing process.

Two API-containing batches showed low values in API assay; this result could be due to the small batch size and to the losses during the manufacturing process and the samples for IPCs on the final mixtures.

API-Containing Batches Manufactured by Dry Granulation with a 1:2 API/Saccharide Weight Ratio All the saccharide previously investigated by dry granulation to manufacture tablets with a 1:5 API/Saccharide weight ratio were also evaluated at a ratio of 1:2.

For the manufacturing process see above. In this case, the obtained mixture was tabletted by using a 8 mm diameter punch.

Two types of disintegrant were used: microcrystalline cellulose (Avicel® PH 112), as a standard disintegrant, and crosslinked polyvinylpyrrolidone (Ccrospovidone®', used just for the batch D001T/105. For this batch we have explored the use of Avicel® PH 112 and of Crospovidone®. The Crospovidone® was chosen according to the previous cyclodextrin based formulation manufactured by dry granulation with a 1:5 API/Saccharide (see previous results).

Table 29 and Table 30 summarize the composition of each API-containing formulation manufactured by dry granulation with an API/Saccharide weight ratio of 1:2 and the results of the analytical tests performed on both, the final mixtures and the tablets. All API-containing batches showed suitable uniformity of mass, homogeneity of API content and low impurities content. Friability and hardness values are, in the most of the cases, in compliance with the specifications. In the case of batches D001T/093, D001T/095 and D001T/096, the results of the dissolution test performed on 6 tablets showed out of specifications values with a high RSD and the test was extended to a sample of 12 tablets.

Cyclodextrin based tablets show good properties with both disintegrants (Avicel® PH 112 and Crospovidone®).

TABLE 29

Dry granulation—API/Saccharide weight ratio 1:2. API—containing batches final mixture composition and analytical results.

| | API—containing Batches manufactured by Dry Granulation API/SaccharideSaccharide ratio 1:2 | | | | | | |
|---|---|---|---|---|---|---|---|
| Components | D001T/091 (%w/w) | D001T/092 (%w/w) | D001T/093 (%w/w) | D001T/094 (%w/w) | D001T/105 (%w/w) | D001T/095 (%w/w) | D001T/096 (%w/w) |
| Bendamustine HCl | 31.1 | 31.1 | 31.1 | 31.1 | 31.1 | 31.1 | 31.1 |
| Lactose Monohydrate (Supertab 14 SD) | 62.3 | — | — | — | — | — | — |
| Lactose Anhydrous (Supertab 21 AN) | — | 62.3 | — | — | — | — | — |
| Sorbitol (Neosorb P60W) | — | — | 62.3 | — | — | — | — |
| β-Ciclodextrine (Kleptose DC) | — | — | — | 62.3 | 62.3 | — | — |
| Sucrose97% + Maltodextrine3% (EV SaccharideSaccharide DC 3.75 MD) | — | — | — | — | — | 62.3 | — |

TABLE 29-continued

Dry granulation—API/Saccharide weight ratio 1:2. API—containing batches final mixture composition and analytical results.

API—containing Batches manufactured by Dry Granulation API/SaccharideSaccharide ratio 1:2

| Components | D001T/091 (%$_{w/w}$) | D001T/092 (%$_{w/w}$) | D001T/093 (%$_{w/w}$) | D001T/094 (%$_{w/w}$) | D001T/105 (%$_{w/w}$) | D001T/095 (%$_{w/w}$) | D001T/096 (%$_{w/w}$) |
|---|---|---|---|---|---|---|---|
| Maltose (Food grade) (Sunmalt S) | — | — | — | — | — | — | 62.3 |
| Avicel PH 112 | 5.9 | 5.9 | 5.9 | 5.9 | | 5.9 | 5.9 |
| Crospovidone | | | | | 5.9 | | |
| Magnesium Stearate | 0.7 | 0.7 | 0.7 | 0.7 | 0.7 | 0.7 | 0.7 |

Results of analytical tests performed on final mixtures

| | | | | | | | |
|---|---|---|---|---|---|---|---|
| Flowability (seconds) (Test performed according to EP 6.0, par. 2.9.16) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) |

TABLE 30

Dry granulation—API/Saccharide weight ratio 1:2. API-containing batches tablets analytical results.

| Analytical Test | Specification Limits | D001T/091 | D001T/092 | D001T/093 | D001T/094 | D001T/105 | D001T/095 | D001T/096 |
|---|---|---|---|---|---|---|---|---|
| Identification (HPLC) | Positive | Positive | Positive | Positive | Positive | Positive | Positive | Positive |
| Mean Weight (mg/tablet) | Specific for each formulation | 175.01 Limits: 168.2 ÷ 185.9 | 178.85 Limits: 168.2 ÷ 185.9 | 176.90 RSD 2.3 Limits: 168.2 ÷ 185.9 | 176.06 Limits: 168.2 ÷ 185.9 | 176.40 Limits: 168.2 ÷ 185.9 | 175.81 RSD 6.1 Limits: 168.2 ÷ 185.9 | 180.81 RSD 1.3 Limits: 168.2 ÷ 18.9 |
| Content Uniformity (Test performed according to EP 6.0) | Complies | Complies RSD 2.43 | Complies RSD 2.41 | Complies RSD 3.34 | Complies RSD 3.84 | Complies RSD 2.69 | Complies RSD 2.86 | Complies RSD 3.41 |
| Assay (%) (HPLC) | 95.0%-105.0% | 96.0 | 96.8 | 96.6 | 96.6 | 97.2 | 97.7 | 99.3 |
| Related substances(%) (HPLC) | | | | | | | | |
| HP1 | ≤0.50% | 0.08 | 0.28 | 0.11 | 0.11 | 0.19 | 0.12 | 0.08 |
| BM1 Dimer | ≤0.20% | 0.04 | 0.03 | 0.04 | 0.04 | 0.05 | 0.04 | 0.04 |
| BM1EE | ≤0.50% | 0.13 | 0.13 | 0.13 | 0.14 | 0.13 | 0.12 | 0.13 |
| NP1 | ≤0.20% | 0.01 | 0.01 | 0.01 | 0.01 | 0.01 | 0.01 | 0.02 |
| Individual unknown impurity | ≤0.10% | n.d. | 0.04 | 0.06 | 0.05 | 0.02 | 0.05 | 0.03 |
| Total impurities | ≤1.50% | 0.27 | 0.54 | 0.36 | 0.35 | 0.40 | 0.37 | 0.31 |
| Total impurities after storage at 40° C./75% RH for 3 months | | 0.29 | 0.31 | 0.31 | 0.32 | | 0.35 | 0.35 |
| Dissolution Test | | | | | | | | |
| (Medium: buffer pH = 1.5) | | | | n = 12 | | | n = 12 | n = 12 |
| (% 10 min) | 80% in 30 min | 49.2 | 84.7 | 36.2 (RSD 15.7) | 68.8 | 75.0 | 58.2 (RSD 24.3) | 57.5 (RSD 22.2) |
| (% 20 min) | | 75.2 | 92.4 | 54.6 (RSD 14.0) | 88.8 | 92.1 | 73.8 (RSD 19.1) | 75.1 (RSD 17.5) |
| (% 30 min) | | 84.7 | 93.0 | 65.2 (RSD 10.4) | 92.4 | 92.8 | 82.5 (RSD 20.5) | 84.6 (RSD 19.7) |
| Dissolution after storage at 40° C./75% RH for 3 months | | 89 | 92 | 86 | 92 | | 75 | 89 |
| Moisture content (%) | — | 4.02 | 0.62 | 0.70 | 8.30 | 8.70 | 0.71 | 4.06 |
| Hardness (N) | ≥40N | 95 | 49 | 118 | 110 | 100 | 75 | 125 |
| Friability (%) (Test performed according to EP 6.0) | ≤1.0% | 0.5 | 0.7 | 0.3 | 0.5 | 0.5 | 1.5 | 0.1 | n.d. = not detected

API-Containing Batches Manufactured by Direct Compression with a 1:5

API/SaccharideSaccharide Weight Ratio

The saccharides with suitable characteristics to be manufactured by dry granulation were also explored by using direct compression developing tablets with a 1:5 API/Saccharide ratio.

Two types of disintegrant were used: microcrystalline cellulose (Avicel® PH 112), as a standard disintegrant, and crosslinked polyvinylpyrrolidone (Crospovidone®), used just for batch D001T/029.

This manufacturing process consisted of the following steps:
1. Weighing the API and the excipients.
2. Transferring the raw materials in a double polyethylene bag and mixing for about 5 minutes until a homogeneous powder blend is obtained.
3. Transferring of the powder blend in the hopper of the tabletting machine.
4. Compression of the powder blend using an eccentric tablet machine equipped with a 10 mm diameter punch.

The characteristics of the API-containing batches manufactured by direct compression are presented in the following table.

TABLE 31

Direct Compression—API/Saccharide weight ratio 1:5. API-containing batches final mixture composition and analytical results.

| | API-containing batches manufactured by Direct Compression | | | | |
|---|---|---|---|---|---|
| | D001T/026 (% w/w) | D001T/027 (% w/w) | D001T/028 (% w/w) | D001T/029 (% w/w) | D001T/030 (% w/w) |
| Bendamustine HCL | 16.6 | 16.6 | 15.3 | 16.6 | 15.7 |
| Lactose Monohydrate (Supertab 14 SD) | — | — | 78.4 | — | — |
| Sorbitol (Neosorb P60W) | — | 77.1 | — | — | — |
| β-Cyclodextrin (Kleptose DC) | — | — | — | 77.1 | — |
| Maltose (Food grade) (Sunmalt S) | 77.1 | — | — | — | — |
| Sucrose 97% + Maltodextrin 3% (EV Saccharide DC 3.75 MD) | — | — | — | — | 78.0 |
| Avicel PH 112 | 5.7 | 5.7 | 5.7 | — | 5.7 |
| Crospovidone | — | — | — | 5.7 | — |
| Magnesium Stearate | 0.6 | 0.6 | 0.6 | 0.6 | 0.6 |
| Flowability (seconds) (Test performed according to EP 6.0, par. 2.9.16) | 4.78 (Nozzle 3, diameter = 25 mm) | 4.01 (Nozzle 3, diameter = 25 mm) | Not flow (Nozzle 3, diameter = 25 mm) | Not flow (Nozzle 3, diameter = 25 mm) | 4.12 (Nozzle 3, diameter = 25 mm) |

The obtained results of the analytical tests are listed in table 32.

TABLE 32

Direct Compression—API/Saccharide weight ratio 1:5. API-containing batches tablets analytical results.

| Analytical Test | Specification Limits | Result of analytical Tests performed on tablets | | | | |
|---|---|---|---|---|---|---|
| | | D001T/026 | D001T/027 | D001T/028 | D001T/029 | D001T/030 |
| Identification (HPLC) | Positive | Positive | Positive | Positive | Positive | Positive |
| Mean Weight (mg/tablet) | Specific for each formulation | 333.80 Limits: 315.4 ÷ 348.6 | 332.25 Limits: 315.44 ÷ 348.6 | 363.86 Limits: 342.0 ÷ 378.0 | 331.41 Limits: 315.4 ÷ 348.6 | 356.61 Limits: 332.5 ÷ 367.5 |
| Content Uniformity (Test performed according to EP 6.0) | Complies | Complies RSD 3.51 | Complies RSD 3.60 | Complies RSD 0.88 | Complies RSD 1.57 | Complies RSD 10.84 |
| Assay (%) (HPLC) | 95.0%-105.0% | 94.5 | 97.2 | 100.8 | 100.1 | 99.6 |
| Related substances (%) (HPLC) | | | | | | |
| HP1 | ≤0.5% | 0.10 | 0.11 | 0.12 | 0.13 | 0.11 |
| BM1 Dimer | ≤0.2% | 0.04 | 0.04 | 0.04 | 0.04 | 0.04 |
| BM1EE | ≤0.5% | 0.13 | 0.15 | 0.14 | 0.14 | 0.14 |
| NP1 | ≤0.2% | 0.01 | 0.01 | 0.02 | 0.01 | 0.02 |
| Individual unknown impurity | ≤0.1% | 0.03 | 0.03 | 0.03 | 0.03 | 0.03 |
| Total impurities | ≤1.5% | 0.31 | 0.34 | 0.35 | 0.35 | 0.34 |
| Dissolution Test | | | | | | |

TABLE 32-continued

Direct Compression—API/Saccharide weight ratio 1:5. API-containing batches tablets analytical results.

| Analytical Test | Specification Limits | Result of analytical Tests performed on tablets | | | | |
|---|---|---|---|---|---|---|
| | | D001T/026 | D001T/027 | D001T/028 | D001T/029 | D001T/030 |
| (Medium: buffer pH = 1.5) | | | | | | |
| (% 10 min) | 80% in 30 | 45.5 | 71.5 | 54.7 | 83.3 | 73.5 |
| (% 20 min) | minutes | 69.7 | 89.7 | 88.6 | 89.5 | 90.9 |
| (% 30 min) | | 83.3 | 89.3 | 91.1 | 91.5 | 91.3 |
| Moisture content (%) | — | 5.04 | 0.71 | 4.40 | 11.26 | 0.83 |
| Hardness (N) | ≥40N | 106 | 108 | 74 | 99 | 92 |
| Friability (%) (Test performed according to EP 6.0, par. 2.9.7) | ≤1.0% | 0.2 | 0.2 | 0.2 | 0.1 | 0.8 |

As reported in the above table the API-containing tablets manufactured by direct compression showed no critical differences from the ones produced by dry granulation except for batch D001T/030 (filler: Sucrose 97%+Maltodextrin 3%) that showed a non homogeneous API content and a slight increase in the value of friability.

Wet Granulation:
Placebo Exploratory Trials

Based on the results obtained in the first and second part of the project, the saccharides not suitable for thy granulation or direct compression were investigated by wet granulation.

The present approach to investigate the wet granulation technology is shown below.

Figure 4:
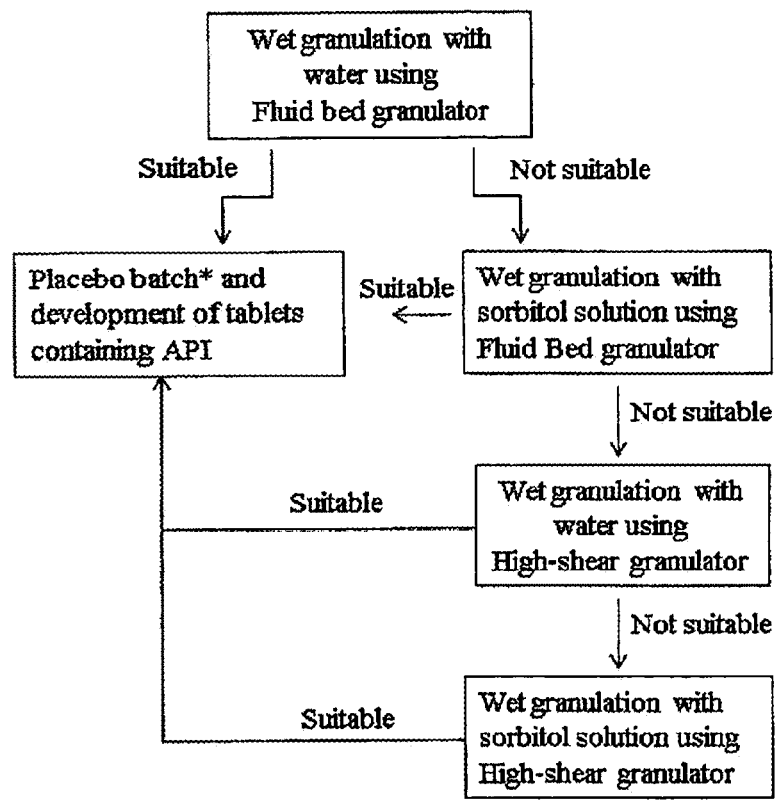
FIG. 4 shows a flow sheet of wet granulation manufacturing trials.

Each saccharide was granulated according to the steps described in the flow-sheet of FIG. 4. At the end of each step the wet granulated saccharide was dried and a compression trial was performed to evaluate if the granulate was suitable for tabletting. Placebo batches were manufactured only for the granulated saccharides with doubtful results of the compression test. The compositions and the relevant analytical results of the placebo trials are reported in Table 33.

Placebo batches were manufactured according to the following steps:
1. Wet granulation of the saccharide with water or sorbitol solution using Fluid Bed or High Shear granulator (see above Flow-sheet of wet granulation manufacturing trials, and table 23)
2. Drying of the wet granulated saccharide in the Fluid Bed granulator or in oven.
3. Sieving the granulated saccharide by using 850 and 710 micron nets.
4. Weighing of all components of the formulation and mixing in a polyethylene bag for 2 minutes.
5. Compression of the powder blend using an eccentric tablet machine equipped with a 10 mm diameter punch.

Avicel PH 112 and magnesium stearate were used as disintegrant and as lubricant, respectively, for all the batches produced.

TABLE 33

Wet granulation. Placebo batches composition and IPC results.

| | Placebo Batches manufactured by Wet Granulation | | | | | | | | | | |
|---|---|---|---|---|---|---|---|---|---|---|---|
| Components | D001T/032 (%w/w) | D001T/034 (%w/w) | D001T/035 (%w/w) | D001T/045 (%w/w) | D001T/051 (%w/w) | D001T/054 (%w/w) | D001T/055 (%w/w) | D001T/057 (%w/w) | D001T/058 (%w/w) | D001T/070 (%w/w) | D001T/075 (%w/w) |
| Dextrose Anhydrous (Dextrose Anhydrous ST 0.5) | 93.66 | — | — | — | — | — | — | — | — | — | — |
| Dextrose Monohydrate (Dextrose Monohydrate) | — | 93.66 | — | — | — | — | — | — | — | — | — |
| Mannitol (Pearlitol 200 SD) | — | — | 93.67 | — | — | — | — | — | — | — | — |
| D-Melezitose monohydrate | — | — | — | 93.55 | — | — | — | — | — | — | — |
| Maltitol (Sweetpearl P200) | — | — | — | — | 93.70 | — | — | — | — | — | — |
| Trehalose (Food grade) (Treha 16400) | — | — | — | — | — | 93.72 | — | — | — | — | — |
| D-Raffinose Pentahydrate | — | — | — | — | — | — | 93.72 | — | — | — | — |
| Erythritol (Food grade) (Zerose Erythritol 16954) | — | — | — | — | — | — | — | — | 93.52 | — | 93.56 |

TABLE 33-continued

Wet granulation. Placebo batches composition and IPC results.

Placebo Batches manufactured by Wet Granulation

| Components | D001T/032 (%w/w) | D001T/034 (%w/w) | D001T/035 (%w/w) | D001T/045 (%w/w) | D001T/051 (%w/w) | D001T/054 (%w/w) | D001T/055 (%w/w) | D001T/057 (%w/w) | D001T/058 (%w/w) | D001T/070 (%w/w) | D001T/075 (%w/w) |
|---|---|---|---|---|---|---|---|---|---|---|---|
| Fructose (Fructose MS) | | | | | | | | | 93.66 | | |
| Xylitol (Xyilisorb 300) | | | | | | | | | | | 93.71 |
| Avicel PH 112 | 5.7 | 5.7 | 5.7 | 5.7 | 5.7 | 5.7 | 5.7 | 5.8 | 5.7 | 5.8 | 5.7 |
| Magnesium Stearate | 0.6 | 0.6 | 0.6 | 0.8 | 0.6 | 0.6 | 0.6 | 0.7 | 0.6 | 0.7 | 0.6 |
| Equipment and Binder Solution utilized for saccharide granulation | Fluid Bed Water | High Shear Water | Fluid Bed Water | Fluid Bed Water | Fluid Bed Sorbitol solution | Fluid Bed Sorbitol solution | Fluid Bed Sorbitol solution | Fluid Bed Sorbitol solution | High Shear Water | High Shear Water | High Shear Water |
| Percentage of sorbitol in the granulate (%w/w) | n/a | n/a | n/a | n/a | 1.2 | 1.1 | 1.1 | 1.1 | N/A | N/A | N/A |
| Percentage of water in the granulate (%w/w) | 1.03 | 7.93 | 0.20 | 5.08 | 0.20 | 0.22 | 15.40 | 0.22 | 0.13 | 0.40 | 0.19 |
| Results of analytical tests performed on tablets | | | | | | | | | | | |
| Appearance | Complies | Complies | Complies | Complies | Complies | Complies | Complies | Complies | Complies | Not Complies | Not Complies |
| Hardness (N) | 98 | 82 | 277 | 96 | 76 | 60 | 64 | 15 | 30 | N/A | N/A |

API-Containing Batches Manufactured by Wet Granulation with a 1:5 API/Saccharide Weight Ratio Manufacturing trials including a wet granulation process were carried out on all saccharides that turned out to be not suitable for tablet manufacturing by dry granulation or direct compression technologies.

The manufacturing process of these trials performed at laboratory scale is summarized as follow:
1. Wet granulation of the saccharide with water or sorbitol solution using Fluid Bed or High Shear granulator (see above Flow-sheet of wet granulation manufacturing trials, and table 34)
2. Drying of the wet granulated saccharide in the Fluid Bed granulator or in oven
3. Sieving by using 850 and 710 micron nets.
4. Weighing of the API and excipients and mixing in a double polyethylene bag for 5 minutes.
5. Compression of the powder blend using an eccentric tablet machine equipped with a 10 mm diameter punch.

Avicel PH 112 and magnesium stearate were used as disintegrant and as lubricant, respectively, for all the batches produced.

Table 33 and Table 34 list the composition of each API-containing formulation manufactured by wet granulation and the results of the analytical tests performed on both, the final mixtures and the tablets.

The results of the analytical tests performed on the final mixtures and on the finished products are, in the most of the cases, in compliance with the specifications. No degradation occurs during the manufacturing process.

Among the saccharides investigated, only Fructose MS (Galam) is not suitable to be processed by wet granulation: the API-containing batch D001T/047 has a high friability and the batch D001T/082 shows friability and hardness values out of specifications.

The batches D001T/060, D001T/061, D001T/082, D001T/086 have low values in API assay and for the batches D001T/082 and D001T/086 the Uniformity of Content does not comply, though the granulate was sieved by using 850 micron and 710 micron nets. This result is probably due to poor powders mixing.

TABLE 34

Wet granulation—API/Saccharide weight ratio 1:5. API-containing batches final mixture composition and analytical results.

API-containing Batches manufactured by Wet Granulation

| Components | D001T/033 (%w/w) | D001T/036 (%w/w) | D001T/037 (%w/w) | D001T/040 (%w/w) | D001T/047 (%w/w) (*) | D001T/059 (%w/w) | D001T/060 (%w/w) | D001T/061 (%w/w) | D001T/082 (%w/w) | D001T/086 (%w/w) | D001T/087 (%w/w) |
|---|---|---|---|---|---|---|---|---|---|---|---|
| Bendamustine HCl | 15.7 | 15.7 | 15.7 | 15.7 | 14.9 | 15.7 | 15.7 | 15.7 | 15.7 | 15.7 | 15.7 |
| Dextrose Anhydrous (Anhydrous Dextrose ST 0.5) | 78 | — | — | — | — | — | — | — | — | — | — |
| Dextrose Monohydrate G | — | 78 | — | — | — | — | — | — | — | — | — |

TABLE 34-continued

Wet granulation—API/Saccharide weight ratio 1:5. API-containing batches final mixture composition and analytical results.

API-containing Batches manufactured by Wet Granulation

| Components | D001T/033 (%w/w) | D001T/036 (%w/w) | D001T/037 (%w/w) | D001T/040 (%w/w) | D001T/047 (%w/w) (*) | D001T/059 (%w/w) | D001T/060 (%w/w) | D001T/061 (%w/w) | D001T/082 (%w/w) | D001T/086 (%w/w) | D001T/087 (%w/w) |
|---|---|---|---|---|---|---|---|---|---|---|---|
| Mannitol (Pearlitol 200 SD) | — | — | 78 | — | — | — | — | — | — | — | — |
| Lactitol Monohydrate (Lacty M) (Food grade) | — | — | — | 78 | — | — | — | — | — | — | — |
| D-Melezitose monohydrate | — | — | — | — | 78.8 | — | — | — | — | — | — |
| Maltitol (Sweetpearl P200) | — | — | — | — | — | 78 | — | — | — | — | — |
| Trehalose (Food grade) (Treha 16400) | — | — | — | — | — | — | 78 | — | — | — | — |
| D-Raffinose Pentahydrate | — | — | — | — | — | — | — | 78 | — | — | — |
| Erythritol (Food grade) (Zerose Erythritol 16954) | — | — | — | — | — | — | — | — | 78 | — | — |
| Xylitol (Xyilisorb 300) (**) | | | | | | | | | | 78 | |
| Fructose MS (**) | | | | | | | | | | | 78 |
| Avicel PH 112 | 5.7 | 5.7 | 5.7 | 5.7 | 5.7 | 5.7 | 5.7 | 5.7 | 5.7 | 5.7 | 5.7 |
| Magnesium Stearate | 0.6 | 0.6 | 0.6 | 0.6 | 0.6 | 0.6 | 0.6 | 0.6 | 0.6 | 0.6 | 0.6 |
| Equipment and Binder Solution utilized for saccharide granulation | Fluid Bed Water | High Shear Water | Fluid Bed Water | Fluid Bed Water | Fluid Bed Water | Fluid Bed Sorbitol solution | Fluid Bed Sorbitol solution | Fluid Bed Sorbitol solution | High Shear Sorbitol solution | High Shear Sorbitol solution | High Shear Sorbitol solution |
| Percentage of sorbitol in the granulate (%w/w) | N/A | N/A | N/A | N/A | N/A | 1.2 | 1.1 | 1.1 | 3.4 | 4.8 | 3.0 |

Results of analytical tests performed on final mixtures

| Flowability (seconds) (Test performed according to EP 6.0, par. 2.9.16) | Not flow (Nozzle 3, diameter = 25.0 mm) | 18.95 (Nozzle 1, diameter = 10.0 mm) | 11.14 (Nozzle 2, diameter = 15.0 mm) | 6.12 (Nozzle 2, diameter = 15.0 mm) | Not flow (Nozzle 3, diameter = 25.0 mm) | 5.12 (Nozzle 2, diameter = 15.0 mm) | 6.46 (Nozzle 2, diameter = 15.0 mm) | 5.35 (Nozzle 2, diameter = 15.0 mm) | Not flow (Nozzle 3, diameter = 25.0 mm) | 4.23 (Nozzle 2, diameter = 15.0 mm) | Not flow (Nozzle 3, diameter = 25.0 mm) |

Observations on manufactured tablets

| Appearance | Complies | Complies | Complies | Complies | Complies | Complies | Complies | Complies | Complies | Complies | Not Complies (***) |
| Stability Study | Suitable for Stability Study | Suitable for Stability Study | Suitable for Stability Study | Suitable for Stability Study | Suitable for Stability Study | Suitable for Stability Study | Suitable for Stability Study | Suitable for Stability Study | Suitable for Stability Study | Suitable for Stability Study | Not Suitable for Stability Study |

(*) This batch contains an excess of A.P.I (5.9%);
(**) It was not possible to investigate granulation step using fluid bed with saccharide solution because these saccharides are not fluidized with air stream;
(***) The final mixture is not suitable for tabletting

TABLE 35

Wet granulation—API/Saccharide weight ratio 1:5. API-containing batches tablets analytical results.

| | Specification | | Results of analytical tests performed on tablets | | | | | | | | | |
|---|---|---|---|---|---|---|---|---|---|---|---|---|
| Analytical Test | Limits | | D001T/033 | D001T/036 | D001T/037 | D001T/040 | D001T/047 | D001T/059 | D001T/060 | D001T/061 | D001T/082 | D001T/086 | D001T/087 |
| Identification (HPLC) | Positive | | Positive | Positive | Positive | Positive | Positive | Positive | Positive | Positive | Positive | Positive | N/A |
| Mean Weight (mg/tablet) | Specific for each formulation | | 348.52 Limits: 332.5 ÷ 367.5 | 351.56 Limits: 332.5 ÷ 367.5 | 354.06 Limits: 332.5 ÷ 367.5 | 351.98 Limits: 332.5 ÷ 367.5 | 368.66 Limits: 351.5 ÷ 388.5 | 347.49 Limits: 332.5 ÷ 367.5 | 350.37 Limits: 332.5 ÷ 367.5 | 349.04 Limits: 332.5 ÷ 367.5 | 352.09 Limits: 332.5 ÷ 367.5 | 351.78 Limits: 332.5 ÷ 367.5 | N/A |
| Content Uniformity (Test performed according to EP 6.0) | Complies | | Complies RSD 1.50 | Complies RSD 3.64 | Complies RSD 1.35 | Complies RSD 2.82 | Complies RSD 1.11 | Complies RSD 3.36 | Complies RSD 3.38 | Complies RSD 2.99 | Not complies | Not complies | N/A |
| Assay (%) (HPLC) | 95.0%-105.0% | | 101.0 | 98.2 | 98.4 | 98.6 | 101.2 | 96.7 | 91.3 | 92.7 | 90.6 | 94.0 | N/A |
| Related substances (%) (HPLC) | | | | | | | | | | | | | |
| HP1 | ≤0.5% | | 0.08 | 0.08 | 0.09 | 0.08 | 0.10 | 0.07 | 0.07 | 0.13 | 0.05 | 0.21 | |
| BM1 Dimer | ≤0.2% | | 0.04 | 0.04 | 0.04 | 0.04 | 0.04 | 0.04 | 0.04 | 0.04 | 0.04 | 0.04 | |
| BM1EE | ≤0.5% | | 0.13 | 0.13 | 0.13 | 0.14 | 0.16 | 0.14 | 0.13 | 0.13 | 0.12 | 0.15 | |
| NP1 | ≤0.2% | | 0.01 | 0.01 | 0.01 | 0.01 | 0.01 | 0.01 | 0.01 | 0.01 | 0.01 | 0.02 | |
| Individual unknown impurity | ≤0.1% | | 0.02 | 0.02 | 0.02 | 0.03 | 0.03 | n.d. | 0.01 | 0.02 | 0.02 | 0.04 | N/A |
| Total impurities | ≤1.5% | | 0.30 | 0.30 | 0.31 | 0.30 | 0.34 | 0.26 | 0.26 | 0.33 | 0.24 | 0.49 | |
| Dissolution Test (Medium: buffer pH = 1.5) | 80% in 30 minutes | | | | | | | | | | | | |
| (% 10 min) | | | 91.9 | 73.9 | 97.1 | 77.0 | 80.9 | 77.5 | 86.3 | 71.4 | 90.5 | 87.2 | |
| (% 20 min) | | | 93.3 | 90.5 | 95.5 | 88.4 | 93.5 | 87.2 | 99.7 | 88.4 | 89.0 | 92.2 | |
| (% 30 min) | | | 91.8 | 89.5 | 93.7 | 87.8 | 92.3 | 86.9 | 99.9 | 87.9 | 87.2 | 89.2 | N/A |
| Moisture content (%) | — | | 1.15 | 6.58 | 0.59 | 4.48 | 4.14 | 0.49 | 7.81 | 12.12 | 0.51 | 0.56 | 0.90 |
| Hardness (N) | ≥40N | | 68 | 66 | 140 | 46 | 73 | 81 | 48 | 71 | 26 | 56 | N/A |
| Friability (%) (Test performed according to EP 6.0, par. 2.9.7) | ≤1.0% | | 0.5 | 0.5 | 0.2 | 0.6 | Test failure (28.3) | 0.4 | 0.4 | 0.3 | Test failure (74) | 0.3 | N/A |

API-Containing Batches Manufactured by Wet Granulation with a 1:2 API/Saccharide Weight Ratio All saccharides previously investigated by wet granulation to manufacture tablets with a 1:5 API/Saccharide weight ratio were also evaluated at a ratio of 1:2.

The fructose was not evaluated at a ratio of 1:2 because the obtained granulate is not suitable for tabletting.

Avicel PH 112 and magnesium stearate were used as disintegrant and as lubricant, respectively, for all the batches produced.

To improve the uniformity of the API content, these API-containing batches were manufactured by applying the following approach:

1. Wet granulation of the saccharide by using procedures previously optimized
2. Preparation of the API-containing mixture
3. Dry granulation of the mixture (Slugs production→Slugs sieving)
4. Tabletting of the obtained mixture by using a 8 mm diameter punch.

For the step 3 (Dry granulation of the mixture) see above.

Table 36 and table 37 report the compositions and the analytical results of the API-containing batches manufactured by using wet granulated saccharides with an API/Saccharide weight ratio of 1:2. Friability is, in the most of the cases, out of specifications. The API/Saccharide weight change does not compromise the technological properties of the D001T/084 batch (Filler: granulated mannitol).

TABLE 36

Wet granulation-A.P.I./Saccharide weight ratio 1:2. API-containing batches final mixture composition and analytical results.

| Components | API-containing Batches manufactured by Wet Granulation API/Saccharide ratio 1:2 | | | | | | | | | |
|---|---|---|---|---|---|---|---|---|---|---|
| | D001T/114 (%$_{w/w}$) | D001T/115 (%$_{w/w}$) | D001T/084 (%$_{w/w}$) | D001T/116 (%$_{w/w}$) | D001T/117 (%$_{w/w}$) | D001T/118 (%$_{w/w}$) | D001T/119 (%$_{w/w}$) | D001T/120 (%$_{w/w}$) | D001T/123 (%$_{w/w}$)(*) | D001T/124 (%$_{w/w}$) |
| Bendamustine HCl | 31.1 | 31.1 | 31.1 | 31.1 | 31.1 | 31.1 | 31.1 | 31.1 | 31.1 | 31.1 |
| Dextrose Monohydrate G | 62.3 | — | — | — | — | — | — | — | — | — |
| Dextrose Anhydrous (Anhydrous Dextrose ST 0.5) | — | 62.3 | — | — | — | — | — | — | — | — |
| Mannitol (Pearlitol 200 SD) | — | — | 62.3 | — | — | — | — | — | — | — |
| D-Melezitose monohydrate | — | — | — | 62.3 | — | — | — | — | — | — |
| Maltitol (Sweetpearl P200) | — | — | — | — | 62.3 | — | — | — | — | — |
| Trehalose (Food grade) (Treha 16400) | — | — | — | — | — | 62.3 | — | — | — | — |
| D-Raffinose Pentahydrate | — | — | — | — | — | — | 62.3 | — | — | — |
| Erythritol (Food grade) (Zerose Erythritol 16954) | — | — | — | — | — | — | — | 62.3 | — | — |
| Lactitol monohydrate (*) | — | — | — | — | — | — | — | — | 62.3 | — |
| Xylitol (Xyilisorb 300) (**) | — | — | — | — | — | — | — | — | — | 62.3 |
| Avicel PH 112 | 5.9 | 5.9 | 5.9 | 5.9 | 5.9 | 5.9 | 5.9 | 5.9 | 5.9 | 5.9 |
| Magnesium Stearate | 0.7 | 0.7 | 0.7 | 0.7 | 0.7 | 0.7 | 0.7 | 0.7 | 0.7 | 0.7 |
| Equipment and Binder Solution utilized for saccharide granulation | High Shear Water | Fluid Bed Water | Fluid Bed Water | Fluid Bed Water | Fluid Bed Sorbitol solution | Fluid Bed Sorbitol solution | Fluid Bed Sorbitol solution | High Shear Sorbitol solution | Fluid Bed Water | High Shear Sorbitol solution |
| Percentage of sorbitol in the granulate (%$_{w/w}$) | N/A | N/A | N/A | N/A | 1.2 | 1.1 | 1.1 | 3.4 | N/A | 4.8 |
| Results of analytical Tests performed on final mixtures | | | | | | | | | | |
| Flowability (seconds) (Test performed according to EP 6.0, par. 2.9.16) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) |

(*)As the lactitol used to develop the previous formulation (API/Saccharide weight ratio 1:5) is no longer commercialy available, this batch was manufactured by using lactitol purchased by new manufacturer (Lactitol MC by Danisco).

TABLE 37

Wet granulation-A.P.I./Saccharide weight ratio 1:2. API-containing batches tablets analytical results.

| Analytical Test | Specification Limits | Results of analytical tests performed on tablets | | | | | | | | | |
|---|---|---|---|---|---|---|---|---|---|---|---|
| | | D001T/114 | D001T/115 | D001T/084 | D001T/116 | D001T/117 | D001T/118 | D001T/119 | D001T/120 | D001T/123 | D001T/124 |
| Identification (HPLC) | Positive | Positive | Positive | Positive | Positive | Positive | Positive | Positive | Positive | Positive | Positive |
| Mean Weight (mg/tablet) | Specific for each formulation Limits: 168.2 ÷ 185.9 | 178.67 Limits: 168.2 ÷ 185.9 | 184.41 Limits: 168.2 ÷ 185.9 | 177.14 Limits: 168.2 ÷ 185.9 | 174.81 Limits: 168.2 ÷ 185.9 | 178.70 Limits: 168.2 ÷ 185.9 | 179.86 Limits: 168.2 ÷ 185.9 | 177.30 Limits: 168.2 ÷ 185.9 | 183.26 Limits: 168.2 ÷ 185.9 | 180.33 Limits: 168.2 ÷ 185.9 | 173.38 Limits: 168.2 ÷ 185.9 |
| Content Uniformity (Test performed | Complies | Complies RSD 2.3 | Complies RSD 2.9 | Complies RSD 2.40 | Complies RSD 3.4 | Complies RSD 4.0 | Complies RSD 1.7 | Complies RSD 1.4 | Not Complies RSD 7.4 | Not Complies RSD 11.3 | Complies RSD 2.7 |

TABLE 37-continued

Wet granulation-A.P.I./Saccharide weight ratio 1:2. API-containing batches tablets analytical results.

| Analytical Test | Specification Limits | Results of analytical tests performed on tablets | | | | | | | | |
|---|---|---|---|---|---|---|---|---|---|---|
| | | D001T/114 | D001T/115 | D001T/084 | D001T/116 | D001T/117 | D001T/118 | D001T/119 | D001T/120 | D001T/123 | D001T/124 |
| according to EP 6.0) Assay (%) (HPLC) Related substances (%) (HPLC) | 95.0%-105.0% | 96.9 | 103.5 | 98.8 | 94.8 | 98.5 | 98.0 | 96.9 | 100.4 | 98.0 | 96.7 |
| HP1 | ≤0.50% | 0.07 | 0.14 | 0.09 | 0.07 | 0.08 | 0.06 | 0.11 | 0.09 | 0.05 | 0.06 |
| BM1 Dimer | ≤0.20% | 0.03 | 0.04 | 0.04 | 0.04 | 0.04 | 0.04 | 0.04 | 0.04 | 0.04 | 0.03 |
| BM1EE | ≤0.50% | 0.14 | 0.16 | 0.13 | 0.13 | 0.15 | 0.15 | 0.14 | 0.14 | 0.15 | 0.13 |
| NP1 | ≤0.20% | 0.01 | 0.01 | 0.01 | 0.01 | 0.01 | 0.01 | 0.01 | 0.01 | 0.01 | 0.01 |
| Individual unknown impurity | ≤0.10% | n.d. | n.d. | n.d. | 0.01 | 0.02 | 0.02 | 0.02 | 0.04 | 0.03 | 0.03 |
| Total impurities | ≤1.50% | 0.25 | 0.35 | 0.27 | 0.27 | 0.33 | 0.32 | 0.34 | 0.37 | 0.32 | 0.29 |
| Dissolution Test (Medium: buffer pH = 1.5) | | | | | | | | | | | |
| (% 10 min) | 80% in 30 min | 71.7 | 85.3 | 94.4 | 65.6 | 49.8 | 48.2 | 68.2 | 81.9 | 51.4 | 58.2 |
| (% 20 min) | | 93.5 | 91.7 | 93.8 | 83.6 | 69.2 | 74.5 | 92.5 | 84.4 | 71.9 | 80.4 |
| (% 30 min) | | 94.5 | 91.8 | 92.6 | 88.8 | 88.8 | 84.8 | 92.5 | 84.5 | 82.2 | 86.3 |
| Moisture content (%) | — | 5.4 | 1.1 | 1.5 | 3.2 | 0.5 | 6.3 | 9.4 | 0.8 | 3.6 | 0.5 |
| Hardness (N) | ≥40N | 47 | 46 | 67 | 49 | 41 | 44 | 50 | 18 | 43 | 45 |
| Friability (%) (Test performed according to EP6.0) | ≤1.0% | Test failure (9.0) | Test failure (41.3) | 0.4 | Test failure (60.0) | 1.2 | Test failure (41.1) | Test failure (16.8) | Test failure (97.4) | Test failure (16.0) | 0.8 |

Effect of the API/Mannitol Weight Ratio

Mannitol based tablets were manufactured investigating the following API/mannitol ratios: (1:0.01, 1:0.1, 1:0.5, 1:1.7, 1:4, 1:5, 1:6 and 1:10). The formulation with a 1:5 API/mannitol weight ratio (standard formulation) was reported above.

For the production of these batches Avicel PH 112 and magnesium stearate were used as disintegrant and as lubricant respectively. Regarding the manufacturing process, for the 1:1.7, 1:4, and 1:6 ratios, wet granulated mannitol, Bendamustine Hydrochloride and excipients were accurately weighed and mixed in a double polyethylene bag for 5 minutes. For batch D001T/110 (1:10 ratio) a premix was performed. In this case, Bendamustine Hydrochloride was mixed, for 5 min, with half quantity of the excipients mixture. Then, the obtained mixture was added to the remaining quantity of the excipients and mixed for additional 5 minutes. The final mixture was tabletted using the tabletting machine equipped with a suitable punch (8 mm diameter punch for 1:1, 1:1.7 and 1:2 ratios, 10 mm in the case of 1:4 and 1:6 ratios, 12 mm for 1:7 ratio and 14 mm for 1:10 ratio).

With regard to the 1:0.01, 1:0.1, 1:0.5 ratios, we have applied the manufacturing process reported above (wet granulation of the saccharide and subsequent dry granulation), to improve the API content uniformity. The obtained mixture was tabletted using a 6 mm diameter punch.

The following tables (Table 38 and Table 39) summarize the compositions and the analytical results of the API-containing formulations manufactured to study the effects of the different API/Mannitol ratios. The batches D001T/111, D001T/083 and D001T/106 showed high friability and for the batches D001T/106, D001T/108 and D001T/109 the Uniformity of Content did not comply deviating from data trends previously obtained. This result may be due to the fact that these batches were produced using a new lot of Bendamustine HCl (Lot number: F08-05873) that may have different physical properties.

TABLE 38

Effect of the A.P.I./Mannitol weight ratio. API-containing batches final mixture composition A.P.I./Mannitol Ratio Study

| | D001T/113 (%$_{w/w}$) | D001T/112 (%$_{w/w}$) | D001T/111 (%$_{w/w}$) | D001T/083 (%$_{w/w}$) | D001T/106 (%$_{w/w}$) | D001T/084 (%$_{w/w}$) | D001T/108 (%$_{w/w}$) | D001T/037 (%$_{w/w}$) | D001T/109 (%$_{w/w}$) | D001T/085 (%$_{w/w}$) | D001T/110 (%$_{w/w}$) |
|---|---|---|---|---|---|---|---|---|---|---|---|
| A.P.I./ Saccharide Ratio | 1:0.01 (*) | 1:0.1 (*) | 1:0.5 (*) | 1:1 | 1:1.7 | 1:2 | 1:4 | 1:5 | 1:6 | 1:7 | 1:10 |

TABLE 38-continued

Effect of the A.P.I./Mannitol weight ratio. API-containing batches final mixture composition

| | A.P.I./Mannitol Ratio Study | | | | | | | | | | |
|---|---|---|---|---|---|---|---|---|---|---|---|
| | D001T/113 (%$_{w/w}$) | D001T/112 (%$_{w/w}$) | D001T/111 (%$_{w/w}$) | D001T/083 (%$_{w/w}$) | D001T/106 (%$_{w/w}$) | D001T/084 (%$_{w/w}$) | D001T/108 (%$_{w/w}$) | D001T/037 (%$_{w/w}$) | D001T/109 (%$_{w/w}$) | D001T/085 (%$_{w/w}$) | D001T/110 (%$_{w/w}$) |
| Bendamustine HCl | 55.1 | 55.1 | 55.1 | 44.1 | 34.4 | 31.1 | 18.7 | 15.7 | 13.4 | 11.9 | 8.6 |
| Mannitol Granulated (Pearlitol 200 SD) | 0.55 | 5.51 | 27.6 | 44.1 | 58.5 | 62.3 | 74.7 | 78.0 | 80.7 | 82.9 | 86.1 |
| Avicel PH 112 | 43.7 | 38.7 | 16.6 | 11.1 | 6.4 | 5.9 | 5.9 | 5.7 | 5.3 | 4.6 | 4.6 |
| Magnesium Stearate | 0.7 | 0.7 | 0.7 | 0.7 | 0.7 | 0.7 | 0.7 | 0.6 | 0.6 | 0.6 | 0.7 |
| Batch number of Bendamustine HCl | F08-03755 | F08-03755 | F08-03755 | F08-03755 | F08-05873 | F08-03755 | F8-05873 | F08-03755 | F8-05873 | F08-03755 | F08-03755 |
| | Results of analytical tests performed on final mixtures | | | | | | | | | | |
| Flowability (seconds) (Test performed according to EP 6.0, par. 2.9.16) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | 5.20 (Nozzle 3, diameter = 25.0 mm) | 11.14 (Nozzle 2, diameter = 15.0 mm) | 2.59 (Nozzle 3, diameter = 25.0 mm) | 10.90 (Nozzle 2, diameter = 15.0 mm) | 10.06 (Nozzle 2, diameter = 15.0 mm) |

(*) Batches manufactured by using the experimental approach reported above

 Standard formulation 1:5 API/Saccharide weight ratio

TABLE 39

Effect of the A.P.I./Mannitol weight ratio study. API-containing batches tablets analytical results.

| | Specification | | Results of analytical tests performed on tablets | | | | | | | | | |
|---|---|---|---|---|---|---|---|---|---|---|---|---|
| Analytical Test | Limits | D001T/113 | D001T/112 | D001T/111 | D001T/083 | D001T/106 | D001T/084 | D001T/108 | D001T/037 | D001T/109 | D001T/085 | D001T/110 |
| Identification (HPLC) | Positive | Positive | Positive | Positive | Positive | Positive | Positive | Positive | Positive | Positive | Positive | Positive |
| Mean Weight (mg/tablet) | Specific for each formulation | 100.28 | 104.51 | 95.95 | 126.76 | 163.85 | 177.14 | 299.05 | 354.06 | 410.0 | 469.55 | 646.24 |
| Content Uniformity (Test performed according to EP 6.0) | Complies | Limits: 95 ÷ 105 Complies RSD 2.7 | Limits: 95 ÷ 105 Complies RSD 3.2 | Limits: 95 ÷ 105 Complies RSD 3.7 | Limits: 118.75 ÷ 131.3 Complies RSD 2.77 | Limits: 152.0 ÷ 168.0 Not Complies RSD 14.24 | Limits: 168.2 ÷ 185.9 Complies RSD 2.40 | Limits: 280.3 ÷ 309.8 Not Complies RSD 8.63 | Limits: 332.5 ÷ 367.5 Complies 1.35 | Limits: 389.5 ÷ 430.5 Not Complies RSD 8.33 | Limits: 441.8 ÷ 488.3 Complies RSD 2.79 | Limits: 608 ÷ 672 Complies RSD 2.6 |
| Assay (%) (HPLC) | 95.0%-105.0% | 101.6 | 104.1 | 95.4 | 99.3 | 96.8 | 98.8 | 97.1 | 98.4 | 97.1 | 95.1 | 99.4 |
| Related substances (%) (HPLC) | | | | | | | | | | | | |
| HP1 | ≤0.50% | 0.07 | 0.11 | 0.06 | 0.09 | 0.09 | 0.09 | 0.09 | 0.09 | 0.06 | 0.12 | 0.07 |
| RM1 Dimer | ≤0.20% | 0.04 | 0.04 | 0.04 | 0.04 | 0.04 | 0.04 | 0.04 | 0.04 | 0.04 | 0.03 | 0.04 |
| BM1EE | ≤0.50% | 0.15 | 0.16 | 0.15 | 0.14 | 0.12 | 0.13 | 0.13 | 0.13 | 0.13 | 0.14 | 0.14 |
| NP1 | ≤0.20% | 0.01 | 0.01 | 0.01 | 0.01 | 0.01 | 0.01 | 0.01 | 0.01 | 0.05 | 0.01 | 0.01 |
| Individual unknown impurity | ≤0.10% | n.d. | n.d. | n.d. | 0.02 | n.d. | n.d. | n.d. | 0.02 | n.d. | 0.03 | n.d. |
| Total impurities | ≤1.50% | 0.27 | 0.32 | 0.26 | 0.31 | 0.26 | 0.27 | 0.27 | 0.31 | 0.28 | 0.33 | 0.26 |
| Dissolution Test (Medium: buffer pH = 1.5) | 80% in 30 min | | | | | | | | | | | |
| (% 10 min) | | 71.8 | 81.3 | 86.7 | 80.6 | 75.7 | 94.4 | 90.1 | 97.1 | 91.4 | 96.7 | 97.7 |
| (% 20 min) | | 77.5 | 88.0 | 92.1 | 83.1 | 81.8 | 93.8 | 89.8 | 95.5 | 91.1 | 94.6 | 97.2 |
| (% 30 min) | | 80.0 | 87.5 | 95.2 | 81.3 | 84.1 | 92.6 | 88.4 | 93.7 | 90.6 | 92.8 | 96.3 |
| Moisture content (%) | — | 2.3 | 2.1 | 1.1 | 0.8 | 0.5 | 1.5 | 0.4 | 0.6 | 0.5 | 0.4 | 0.6 |
| Hardness (N) | ≥40N | 88 | 85 | 67 Test failure (6.1) | 63 Test failure (5.2) | 70 Test failure (18.8) | 67 | 226 | 140 | 227 | 181 | 91 |
| Friability (%) (Test performed according to EP 6.0) | ≤1.0% | 0.7 | 0.9 | | | | 0.4 | 0.3 | 0.2 | 0.5 | 0.3 | 0.9 |

☐ Standard formulation 1:5 API/Saccharide weight ratio

Saccharides Combination Study

Table 40 and Table 41 report the results concerning the saccharide combination study.

The following combinations were investigated:

Monosaccharide/Disaccharide 1:1

(*)Mannitol (Pearlitol 200 SD)/Lactose Anhydrous (SuperTab 21 AN)

Sorbitol (Neosorb P60 W)/Maltose (Sunmalt S)

Oligosaccharide/Monosaccharide 1:1

(*)D-Melezitose monohydrate/(*)Dextrose anhydrous ST 0.5

(*)Raffinose Pentahydrate granulated/(*)Mannitol granulated (Pearlitol 200 SD)

Oligosaccharide/Disaccharide 1:1

(*)Raffinose Pentahydrate granulated/Lactose Monohydrate (Supertab 14SD)

β-Ciclodextrine (Kleptose DC)/Sucrose (EV Saccharide)

(*) These saccharides were granulated by wet granulation

The manufacturing process consisted in direct compression of the unprocessed or granulated saccharide.

By using Avicel PH 112 and magnesium stearate as disintegrant and as lubricant, respectively, these batches were manufactured performing the following steps:

1. The saccharides (or the granulated saccharide), Bendamustine Hydrochloride and excipients were accurately weighed and mixed in a double polyethylene bag for 5 minutes.
2. The obtained mixture was tabletted by using a 10 mm diameter punch.

TABLE 40

Saccharides Combination Study. API-containing batches final mixture composition and analytical results.

| | Saccharide Combination Study API-containing Batches | | | | | |
|---|---|---|---|---|---|---|
| Components | D001T/049 (%$_{w/w}$) | D001T/074 (%$_{w/w}$) | D001T/100 (%$_{w/w}$) | D001T/101 (%$_{w/w}$) | D001T/102 (%$_{w/w}$) | D001T/103 (%$_{w/w}$) |
| Bendamustine HCl | 14.89 | 15.74 | 15.74 | 15.74 | 15.74 | 15.74 |
| Saccharide combination | | | | | | |
| Oligosaccharide/Monosaccharide 1:1 | | | | | | |
| D-Melezitose monohydrate/Dextrose anhydrous ST 0.5 | 78.81 | — | — | — | — | — |
| Raffinose Pentahydrate/Mannitol (Pearlitol 200 SD) | — | — | — | — | 77.96 | — |
| Saccharide combination | | | | | | |
| Oligosaccharide/Disaccharide 1:1 | | | | | | |
| Raffinose Pentahydrate/Lactose Monohydrate (Supertab 14SD) | — | — | — | — | — | 77.96 |
| β-Ciclodexirine (Kleptose DC)/Sucrose (EV Saccharide) | — | — | — | 77.96 | — | — |
| Saccharide combination | | | | | | |
| Monosaccharide/Disaccharide 1:1 | | | | | | |
| Sorbitol (Neosorb P60W)/Maltose (Sunmalt S) | — | — | 77.96 | — | — | — |
| Mannitol (Pearlitol 200 SD)/Anhydrous Lactose (SuperTab 21 AN) | — | 77.96 | — | — | — | — |
| Avicel PH 112 | 5.70 | 5.70 | 5.70 | 5.70 | 5.70 | 5.70 |
| Magnesium Stearate | 0.60 | 0.60 | 0.60 | 0.60 | 0.60 | 0.60 |
| | Results of analytical tests performed on final mixtures | | | | | |
| Flowability (seconds) (Test performed according to EP 6.0, par. 2.9.16) | Not flow (Nozzle 3, diameter = 25.0 mm) | Not flow (Nozzle 3, diameter = 25.0 mm) | 5.24 (Nozzle 3, diameter = 25.0 mm) | 5.25 (Nozzle 3, diameter = 25.0 mm) | Not flow (Nozzle 3, diameter = 25.0 mm) | Not flow (Nozzle 3, diameter = 25.0 mm) |

TABLE 41

Saccharide Combination Study. API-containing batches tablets analytical results.

| | Specification | Results of analytical tests performed on tablets | | | | | |
|---|---|---|---|---|---|---|---|
| Analytical Test | Limits | D001T/049 | D001T/074 | D001T/100 | D001T/101 | D001T/102 | D001T/103 |
| Identification (HPLC) | Positive | Positive | Positive | Positive | Positive | Positive | Positive |
| Mean Weight (mg/tablet) | Specific for each formulation | 365.96 351.5 ÷ 388.5 | 346.06 332.54 ÷ 367.5 | 351.56 332.5 ÷ 36.5 | 349.60 332.5 ÷ 367.5 | 354.13 332.5 ÷ 367.5 | 348.83 332.5 ÷ 367.5 |
| Content Uniformity (Test performed according to EP 6.0) | Complies | Not complies RSD 5.55 | Complies RSD 1.41 | Not Complies RSD 4.50 | Complies RSD 1.51 | Complies RSD 4.73 | Complies RSD 1.46 |
| Assay (%) (HPLC) | 95.0%-105.0% | 96.7 | 95.1 | 97.5 | 97.6 | 97.9 | 98.9 |
| Related substances (%) | | | | | | | |

TABLE 41-continued

Saccharide Combination Study. API-containing batches tablets analytical results.

|  | Specification | Results of analytical tests performed on tablets | | | | | |
|---|---|---|---|---|---|---|---|
| Analytical Test | Limits | D001T/049 | D001T/074 | D001T/100 | D001T/101 | D001T/102 | D001T/103 |
| (HPLC) | | | | | | | |
| HP1 | ≤0.50% | 0.10 | 0.06 | 0.06 | 0.12 | 0.09 | 0.09 |
| BM1 Dimer | ≤0.20% | 0.04 | 0.03 | 0.04 | 0.04 | 0.04 | 0.04 |
| BM1EE | ≤0.50% | 0.15 | 0.13 | 0.12 | 0.12 | 0.12 | 0.12 |
| NP1 | ≤0.20% | 0.01 | 0.01 | 0.01 | 0.01 | 0.01 | 0.01 |
| Individual unknown impurity | ≤0.10% | 0.03 | n.d. | 0.01 | 0.02 | n.d. | 0.02 |
| Total impurities | ≤1.50% | 0.33 | 0.23 | 0.24 | 0.31 | 0.26 | 0.28 |
| Dissolution Test | | | | | | | |
| (Medium: buffer pH = 1.5) | | | | | | | |
| (% 10 min) | 80% in 30 min | 76.3 | 73.1 | 62.9 | 65.4 | 89.6 | 55.7 |
| (% 20 min) | | 93.8 | 97.4 | 86.1 | 89.4 | 91.1 | 87.6 |
| (% 30 min) | | 92.7 | 99.2 | 91.7 | 93.4 | 89.8 | 88.9 |
| Moisture content (%) | — | 2.70 | 0.60 | 2.77 | 5.66 | 5.38 | 8.12 |
| Hardness (N) | ≥40N | 73 | 147 | 216 | 144 | 93 | 118 |
| Friability (%) | ≤1.0% | 0.4 | 0.1 | 0.1 | 0.2 | Test failure (26.4) | 0.2 |
| (Test performed according to EP 6.0) | | | | | | | |

In general, the tablets manufactured for the saccharides combination studies show good properties. However, the batch D001T/102 (Raffinose Pentahydrate/Mannitol (Pearlitol 200 SD)), show high friability and the batches D001T/100 and D001T/049 are non homogeneous in API content.

Example 22

Freeze Dried Bendamustine HCl (Ribomustin) and Bendamustine HCl/Mannitol Tablets (Api/Saccharide Weight Ratio 1:1.2)

Tablets containing bendamustine hydrochloride/mannitol in a weight ratio of 1:1.2 were prepared by using either freeze dried material obtained from the commercially available product for intravenous application (Ribomustin®) or using wet granulated mannitol and Bendamustine HCl.

The manufacturing processes were performed according to the following experimental operations: the freeze dried powder was removed from the Ribomustin® vials and was sieved using a 850 micron net. The obtained powder and the lubricant (magnesium stearate) were accurately weighed and mixed in a polyethylene bag for 5 minutes. The mixture was slowly transferred in the pressing chamber of the tabletting machine and was manually pressed by using an 8 mm diameter punch in order to obtain small slugs. The slugs were sieved using a 850 micron net and the obtained granulate was manually pressed using a 8 mm diameter punch.

Bendamustine HCl/mannitol tablets were manufactured applying the same operating procedures as described above in this example.

The composition of the formulations is reported in table 42.

TABLE 42

Ribomustin and bendamustine/mannitol tablets. API-containing batches final mixture composition.

|  | Ribomustin and bendamustine/mannitol tablets | |
|---|---|---|
|  | D001T/125 (% w/w) | D001T/126 (% w/w) |
| A.P.I./Saccharide Ratio | 1:1.2 | 1:1.2 |
| Ribomustin Freeze-dried(*) | 99.36 | |
| Bendamustine HCl | | 45.16 |
| Mannitol Granulated (Pearlitol 200 SD) | | 54.20 |
| Magnesium Stearate | 0.64 | 0.64 |
| Batch number of Bendamustine HCl | | F08-03755 |
| Flowability (seconds) (Test performed according to EP 6.0, par. 2.9.16) | N/A | N/A |

(*)Corresponding to 45.16% of Bendamustine HCl and 54.20% of Mannitol

Table 43 reports the data concerning the comparison between the tablets obtained using the freeze dried bendamustine hydrochloride/mannitol mixture and the non freeze-dried bendamustine hydrochloride/mannitol mixture.

TABLE 43

Ribomustin and bendamustine/mannitol tablets. API-containing batches tablets analytical results.

|  | Specification | Results of analytical tests performed on tablets | |
|---|---|---|---|
| Analytical Test | Limits | D001T/125 | D001T/126 |
| Identification (HPLC) | Positive | Positive | Positive |
| Mean Weight (mg/tablet) | Specific for each formulation | 123.45 Limits: 115.9 ÷ 128.1 RSD 6.02 | 121.79 Limits: 115.9 ÷ 128.1 RSD 2.88 |

TABLE 43-continued

Ribomustin and bendamustine/mannitol tablets.
API-containing batches tablets analytical results.

| Analytical Test | Specification Limits | Results of analytical tests performed on tablets | |
|---|---|---|---|
| | | D001T/125 | D001T/126 |
| Content Uniformity (Test performed according to EP 6.0) | Complies | Complies RSD 4.05 | Complies RSD 3.35 |
| Assay (%) (HPLC) | 95.0%-105.0% | 98.6 | 99.5 |
| Related substances (%) (HPLC) | | | |
| HP1 | ≤0.50% | 1.03 | 0.08 |
| BM1 Dimer | ≤0.20% | 0.19 | 0.04 |
| BM1EE | ≤0.50% | 0.19 | 0.14 |
| NP 1 | ≤0.20% | 0.01 | 0.01 |
| Individual unknown impurity | ≤0.10% | 0.03 | n.d. |
| Total impurities | ≤1.50% | 1.50 | 0.27 |
| Dissolution Test (Medium: buffer pH = 1.5) | | | |
| (% 10 min) | 80% in 30 min | 93.3 | 57.7 |
| (% 20 min) | | 94.6 | 80.0 |
| (% 30 min) | | 93.0 | 89.9 |
| Moisture content (%) | — | 1.61 | 0.21 |
| Hardness (N) | ≥40 N | 61 | 44 |
| Friability (%) (Test perform ed according to EP 6,0) | ≤1.0% | N/A | Test failure (15.6) |

Taking as reference target the impurity profile of the Bendamustine Hydrochloride API (see specification limits in the table), batch D001T/125 showed an out of specification value for HP1 impurity. The results of the dissolution test highlight that, although after 10 minutes the dissolution profile of the tablets, containing the freeze-dried bendamustine hydrochloride/mannitol mixture is faster, for both formulations, after 30 minutes the dissolution is in compliance with the current specifications. The friability is out of specification for batch D001T/126, whereas the test was not performed for batch D001T/125 due to lack of sufficient amounts of material.

Example 23

Absolute Bioavailability of Oral Bendamustine in Patients with Cancer

A total of 12 patients was planned for a phase 1, open-label, randomised, 2-way crossover study to investigate the bioavailability of bendamustine after oral administration of a liquid-filled hard capsule formulation of bendamustine hydrochloride. 14 patients who were suffering from multiple myeloma, B-cell type chronic lymphocytic leukemia or advanced indolent non-Hodgkin's lymphoma were enrolled and were treated with bendamustine. Patients were allowed to be previously treated with intravenous bendamustine, but should have received their last intravenous cycle at least 7 days before the first administration of study drug. After signing the informed consent form and following the screening period (days −21 to −2), eligible patients were assigned a patient number which was specific for each study site. Patients were randomized to receive one of the following on day 1 followed by the other on day 8:
  a single oral dose of 110.2 mg (2×55.1 mg) bendamustine HCl
  a single intravenous dose of 100 mg bendamustine HCl Bendamustine was provided a) orally as capsules, a LFHC formulation (liquid-filled, hard-shell capsule) and b) intravenously as a solution after reconstituting a powder for the preparation of a solution for injection. The LFHC formulation (per capsule) was prepared from 55.1 mg bendamustine hydrochloride, 1.2 mg methylparaben, 0.12 mg polyparaben, 0.12 mg butylated hydroxytoluene, 10.9 mg ethanol and 532.56 mg Cremophor® RH40. The vial with powder for concentrate for solution was the marketed product in Germany (Ribomustine®) which contains per vial 100 mg of bendamustine hydrochloride and mannitol as an excipient. This product was reconstituted with water for injection to a final concentration of 2.5 mg/ml of bendamustine HCl and was further diluted with 0.9% NaCl until about 500 ml before administration to the patient, in accordance with the instructions of the package insert.

Patients were admitted to the study site for 2 periods; days −1 to 2 (period 1) and days 7 to 9 (period 2). A total of 12 patients was to be randomized to receive treatment. Six patients were to receive treatment with a single oral dose of 110.2 mg (2×55.1 mg) bendamustine HCl (day 1) followed by a single intravenous dose of 100 mg bendamustine HCl (day 8) while 6 other patients were to receive treatment in the alternate order. Patients underwent a washout period of at least 7 days between treatments.

Bendamustine is metabolized via hydrolysis to the inactive metabolites monohydroxybendamustine (HP1) and dihydroxybendamustine (HP2) and via cytochrome P450 (CYP 1A2) to the active metabolites γ-hydroxybendamustine (M3) and N-desmethylbendamustine (M4).

After oral and intravenous administration of bendamustine the concentration of bendamustine, as well as that of the active metabolites of bendamustine (M3 and M4), were determined in plasma and urine samples on day 1 and day 8. Patients returned to the study site for an end-of-study visit 7 to 14 days after completion of the second treatment period, or after early discharge/withdrawal. Subsequently the pharmacokinetic parameters of bendamustine and its metabolites were calculated.

No interim analyses were planned or conducted.

The following results were obtained:
Population:
  Of the 23 patients screened for this study, 14 patients were randomly assigned to treatment and received at least 1 dose of study medication. These included 6 patients receiving the oral/intravenous sequence and 8 patients receiving the intravenous/oral sequence. Of these 14 patients:
    1 was excluded due to a protocol violation (concomitant medication) and received oral medication only, so no intravenous administration;
    1 was excluded from the oral analysis due to vomiting and di not qualify for the bioavailability assessment and
    1 was excluded from the intravenous administration due to an adverse event. This patient received oral dosing only, no intravenous.

Ten (71%) of the 14 patients were male, and all were white. Patient ages ranged from 54 to 82, with a mean of approximately 70 years. Seven of the patients had multiple myeloma, 4 had indolent non-Hodgkin's lymphoma and 3 had chronic lymphocytic leukemia.

Pharmacokinetic Results:

Plasma pharmacokinetic parameters of bendamustine (base), M3 and M4 are shown in Table 44, Table 45 and Table 46, respectively. Based on statistical analysis, the absolute bioavailability (oral versus intravenous ratio of $AUC_{inf}$) of bendamustine was 66% (geometric mean; 90% CI: 55%, 78%). $C_{max}$ after oral dosing was 42% of $C_{max}$ after intravenous dosing (90% CI: 32%, 54%).

TABLE 45

Plasma Pharmacokinetic Parameters for M3

| Treatment | Statistic | $t_{max}$ (h) | $C_{max}$ (ng/mL) | $AUC_{last}$ (ng · h/mL) | $AUC_{inf}$ (ng · h/mL) | $t_{1/2}$ (h) |
| --- | --- | --- | --- | --- | --- | --- |
| Bendamustine | n | 11 | 11 | 11 | 11 | 11 |
| HCl, | Mean | 1.27 | 243 | 367 | 369 | 0.643 |
| 110.2 mg orally | SD | 0.45 | 149 | 194 | 194 | 0.285 |
| Bendamustine | n | 11 | 11 | 11 | 11 | 11 |
| HCl, 100 mg | Mean | 0.823 | 344 | 370 | 372 | 0.727 |
| intravenously | SD | 0.221 | 193 | 178 | 179 | 0.426 |

Notes:
All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).

TABLE 46

Plasma Pharmacokinetic Parameters for M4

| Treatment | Statistic | $t_{max}$ (h) | $C_{max}$ (ng/mL) | $AUC_{last}$ (ng · h/mL) | $AUC_{inf}$ (ng · h/mL) | $t_{1/2}$ (h) |
| --- | --- | --- | --- | --- | --- | --- |
| Bendamustine HCl, | n | 11 | 11 | 11 | 11 | 11 |
| 110.2 mg orally | Mean | 1.325 | 26.9 | 42.8 | 44.4 | 0.515 |
|  | SD | 0.449 | 19.9 | 29.6 | 29.6 | 0.134 |
| Bendamustine HCl, | n | 11 | 11 | 11 | 11 | 11 |
| 100 mg intravenously | Mean | 0.935 | 33.6 | 40.8 | 42.5 | 0.543 |
|  | SD | 0.198 | 20.0 | 22.9 | 22.6 | 0.097 |

Notes:
All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).

TABLE 44

Plasma Pharmacokinetic Parameters for Bendamustine

| Treatment | Statistic | $t_{max}$ (h) | $C_{max}$ (ng/mL) | $AUC_{last}$ (ng · h/mL) | $AUC_{inf}$ (ng · h/mL) |
| --- | --- | --- | --- | --- | --- |
| Bendamustine | n | 12 | 12 | 12 | 12 |
| HCl, | Mean | 0.946 | 3173‡ | 3893 | 3901 |
| 110.2 mg orally | SD | 0.4833 | 1767 | 1929 | 1930 |

|  |  | $t_{1/2}$ (h) | CL/F (L/h) | $V_z$/F (L) | F (%) |
| --- | --- | --- | --- | --- | --- |
|  | n | 12 | 12 | 12 | 11 |
|  | Mean | 0.461 | 31.7 | 20.2 | 69.0† |
|  | SD | 0.107 | 14.5 | 7.9 | 17.9 |

|  | Statistic | $t_{max}$ (h) | $C_{max}$ (ng/mL) | $AUC_{last}$ (ng · h/mL) | $AUC_{inf}$ (ng · h/mL) |
| --- | --- | --- | --- | --- | --- |
| Bendamustine | n | 11 | 11 | 11 | 11 |
| HCl, 100 mg | Mean | 0.524 | 5900‡ | 4785 | 4793 |
| intravenously | SD | 0.119 | 1823 | 1689 | 1691 |

|  |  | $t_{1/2}$ (h) | CL (L/h) | $V_z$ (L) | $V_{ss}$ (L) |
| --- | --- | --- | --- | --- | --- |
|  | n | 11 | 11 | 11 | 10 |
|  | Mean | 0.504 | 21.2 | 14.7 | 10.3 |
|  | SD | 0.143 | 7.4 | 4.1 | 3.2 |

Notes:
All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).
†Arithmetic mean. Geometric mean was 66% (90% CI: 55%, 78%).
‡$C_{max}$ after oral dosing was 42% of $C_{max}$ after intravenous dosing (90% CI: 32%, 54%).

After oral administration, bendamustine was absorbed with a $t_{max}$ of approximately 0.95 hours, with individual values ranging between 15 minutes and 1.8 hours. Mean CL after intravenous administration was 21.2 L/h. Mean $t_{1/2}$ was approximately 30 minutes, both after oral intake and after intravenous administration. Mean $V_Z$ and $V_{SS}$ after intravenous administration were 14.7 L and 10.3 L respectively.

M3 and M4 exposure in plasma was considerably lower than for bendamustine. Mean $AUC_{inf}$ of bendamustine was 10.6 and 88 times higher than for M3 and M4, respectively, after oral administration. In contrast to bendamustine, M3 and M4 $AUC_{inf}$ values were similar for oral and intravenous administration. Based on statistical analysis, after oral administration $AUC_{inf}$ of M3 was 86% of $AUC_{inf}$ after intravenous administration (90% CI: 76%, 98%). For M4 this was 88% (90% CI: 77%, 102%).

Urine pharmacokinetic parameters of bendamustine, M3 and M4 are presented in Table 47, Table 48 and Table 49, respectively. The percentage of the dose excreted in urine unchanged was low (2.6% and 2.1% for oral and intravenous bendamustine, respectively).

TABLE 47

Urine Pharmacokinetic Parameters for Bendamustine

| Treatment | Statistic | $Ae_{last}$ (mg) | $\%Ae_{last}$ (%) | $Ae_{inf}$ (mg) | $\%Ae_{inf}$ (%) | $CL_R$ (L/h) |
|---|---|---|---|---|---|---|
| Bendamustine HCl, | n | 11 | 11 | 11 | 11 | 11 |
| 110.2 mg orally | Mean | 2.66 | 2.66 | 2.64 | 2.64 | 0.788 |
| | SD, CV % | 1.64, 62 | 1.64, 62 | 1.63, 62 | 1.63, 62 | 0.573, 73 |
| | Min-max | 0.40-5.9 | 0.40-5.9 | 0.40-5.8 | 0.40-5.8 | 0.18-2.0 |
| | Median | 2.23 | 2.23 | 2.23 | 2.23 | 0.782 |
| Bendamustine HCl, | n | 11 | 11 | 11 | 11 | 11 |
| 100 mg intravenously | Mean | 1.88 | 2.07 | 1.874 | 2.07 | 0.385 |
| | SD, CV % | 2.29, 122 | 2.52, 122 | 2.28, 122 | 2.52, 122 | 0.414, 108 |
| | Min-max | 0.24-8.0 | 0.27-8.8 | 0.24-8.0 | 0.27-8.8 | 0.06-1.4 |
| | Median | 1.12 | 1.23 | 1.11 | 1.22 | 0.202 |

Notes:
All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).

TABLE 48

Urine Pharmacokinetic Parameters for M3

| Treatment | Statistic | $Ae_{last}$ (mg) | $\%Ae_{last}$ (%) | $Ae_{inf}$ (mg) | $\%Ae_{inf}$ (%) | $CL_R$ (L/h) |
|---|---|---|---|---|---|---|
| Bendamustine HCl, | n | 10 | 10 | 10 | 10 | 10 |
| 110.2 mg orally | Mean | 0.635 | 0.61 | 0.636 | 0.611 | 2.14 |
| | SD, CV % | 0.409, 64 | 0.393, 64 | 0.407, 64 | 0.391, 64 | 2.08, 97 |
| | Min-max | 0.13-1.7 | 0.12-1.6 | 0.13-1.6 | 0.13-1.5 | 0.45-7.4 |
| | Median | 0.576 | 0.553 | 0.558 | 0.537 | 1.49 |
| Bendamustine HCl, | n | 11 | 11 | 11 | 11 | 11 |
| 100 mg intravenously | Mean | 0.433 | 0.457 | 0.435 | 0.459 | 1.29 |
| | SD, CV % | 0.435, 100 | 0.459, 100 | 0.441, 101 | 0.466, 101 | 1.44, 112 |
| | Min-max | 0.017-1.5 | 0.018-1.6 | 0.017-1.6 | 0.018-1.6 | 0.082-5.2 |
| | Median | 0.334 | 0.353 | 0.336 | 0.354 | 0.856 |

Notes:
All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).

TABLE 49

Urine Pharmacokinetic Parameters for M4

| Treatment | Statistic | $Ae_{last}$ (mg) | $\%Ae_{last}$ (%) | $Ae_{inf}$ (mg) | $\%Ae_{inf}$ (%) | $CL_R$ (L/h) |
|---|---|---|---|---|---|---|
| Bendamustine HCl, | n | 10 | 10 | 10 | 10 | 10 |
| 110.2 mg orally | Mean | 0.109 | 0.113 | 0.105 | 0.109 | 2.83 |
| | SD, CV % | 0.058, 54 | 0.060, 54 | 0.052, 50 | 0.054, 50 | 1.96, 69 |
| | Min-max | 0.019-0.21 | 0.019-0.21 | 0.033-0.21 | 0.034-0.22 | 0.78-7.1 |
| | Median | 0.1 | 0.104 | 0.1 | 0.104 | 2.24 |
| Bendamustine HCl, | n | 11 | 11 | 11 | 11 | 11 |
| 100 mg intravenously | Mean | 0.075 | 0.086 | 0.071 | 0.081 | 1.74 |
| | SD, CV % | 0.067, 89 | 0.077, 89 | 0.057, 81 | 0.066, 81 | 1.44, 83 |
| | Min-max | 0.0025-0.18 | 0.0028-0.21 | 0.0034-0.15 | 0.0039-0.17 | 0.18-5.3 |
| | Median | 0.038 | 0.043 | 0.039 | 0.045 | 1.66 |

Notes:
All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).

Safety Results:

Both oral and intravenous administrations of bendamustine were safe and well tolerated. Overall, 6 patients (43%) experienced treatment-emergent adverse events during oral treatment and 3 patients (25%) experienced treatment-emergent adverse events during intravenous treatment. Four patients (29%) receiving the oral dose and no patients receiving the intravenous dose experienced at least 1 adverse event that was considered by the investigator to be related to study drug; these included headache in 1 patient, both headache and fatigue in 1 patient, nausea in 1 patient and vomiting in 1 patient. These events were Grade 1 in severity except for vomiting, which was Grade 2 in severity.

Most adverse events were Grade 1 or Grade 2 in severity. One patient receiving the oral dose experienced Grade 3 increased serum creatinine, hypokalemia, and acute renal failure, and Grade 4 thrombocytopenia, all considered by the investigator to be related to the patient's multiple myeloma and unrelated to study drug. The increased serum creatinine and acute renal failure were severe adverse events, leading to the patient's premature discontinuation from the study. No deaths occurred during the study.

No clinically meaningful trends were observed in mean changes from baseline or categorical shifts for any hematology, biochemistry, urinalysis, or vital sign parameter. A few patients had abnormal hematology or biochemistry findings that were reported as adverse events; none of these were considered to be related to study drug by the investigator.

Mean changes from baseline in heart rate were small and similar between treatment groups. Due to the age and medical history of the patients in this study, most had at least 1 electrocardiogram finding of "abnormal, not clinically significant" at screening and/or during the study. In 1 patient in the intravenous/oral group, abnormal, clinically significant atrial fibrillation, nonspecific ST depression and left axis deviation was observed at screening and following both the intravenous and oral doses.

CONCLUSIONS

Absolute bioavailability of bendamustine after single oral administration using the capsule was 66% (geometric mean; 90% CI: 55%, 78%).

Mean bendamustine CL, $V_Z$ and $V_{SS}$ after intravenous administration were 21.2 L/h, 14.7 L and 10.3 L, respectively.

Bendamustine was quickly absorbed after oral administration (median $t_{max}$ approximately 0.95 hours). Mean $t_{1/2}$ was approximately 30 minutes. Approximately 2.6% of the dose was excreted in urine unchanged after oral administration, while 0.6% was excreted as M3 and 0.1% was excreted as M4. M3 and M4 exposure were approximately 9% and 1% that of bendamustine, respectively, after oral administration.

Based on adverse events reporting, clinical laboratory evaluations, vital signs, physical examinations and electrocardiograms, single doses of both the oral (110.2 mg) and intravenous (100 mg) forms of bendamustine were shown to be safe and well tolerated in this mostly elderly population of patients with indolent non-Hodgkin's lymphoma, multiple myeloma or B-cell type chronic lymphocytic leukemia.

INDUSTRIAL APPLICABILITY

The compositions according to the present invention show many advantages. They can be easily used by the patient without assistance of supervisory medical staff. Hence the time-consuming trips to the hospital may become obsolete, thereby increasing the patient compliance.

Since the dosage forms are solid, they can be swallowed as such, which means that the patient does not need to wait until dissolution of the active ingredient has been achieved. Further due to the good stability of the dosage forms they can be easily stored at room temperature and without the need of any special storage conditions.

By using the dosage forms according to the present invention, a considerable reduction of the volume of the dosage form may be achieved. The reduced size is desirable both from a manufacturing and handling standpoint and patient compliance.

Pharmaceutical compositions show a high dissolution in vitro reducing the degradation of bendamustine in vivo, thus resulting in an improved bioavailability of the bendamustine in vivo.

The invention claimed is:

1. A pharmaceutical composition in an oral dosage form of a hard gelatine capsule which comprises a particulate suspension of bendamustine hydrochloride present as an active ingredient, and a pharmaceutically acceptable excipient which shows a dissolution of the bendamustine of at least 60% in 20 minutes, 70% in 40 minutes and 80% in 60 minutes, as measured with a paddle apparatus at 50 rpm according to the European Pharmacopoeia in 500 ml of a dissolution medium at a pH of 1.5, wherein the pharmaceutically acceptable excipient is selected from the group consisting of macrogol glycerol hydroxystearate, polyoxyl-35-castor oil and ethylene oxide/propylene oxide block copolymer, wherein the composition further comprises a viscosity improving agent.

2. The pharmaceutical composition according to claim 1 wherein it comprises 10 to 1000 mg of the active ingredient.

3. The pharmaceutical composition according to claim 1, wherein the viscosity improving agent comprises colloidal silicon dioxide.

4. The pharmaceutical composition according to claim 1, wherein the viscosity improving agent comprises lauroyl macrogol glycerides.

5. A method of treating a medical condition which is selected from chronic lymphocytic leukemia, acute lymphocytic leukaemia, chronic myelocytic leukaemia, acute myelocytic leukaemia, Hodgkin's disease, non-Hodgkin's lymphoma, multiple myeloma, breast cancer, ovarian cancer, small cell lung cancer and non-small cell lung cancer comprising administering the pharmaceutical composition according to claim 1 to a subject suffering from said medical condition.

6. The method according to claim 5 wherein the pharmaceutical composition is administered in combination with at least one further active agent, and said use of the at least one further active agent is administered prior, concurrently, or subsequently to the pharmaceutical composition and is selected from the group consisting of an antibody specific for CD20, an anthracyclin derivative, a vinca alkaloid or a platin derivative.

7. The method according to claim 6, wherein the antibody specific for CD20 is rituximab; the anthracyclin derivative is doxorubicin or daunorubicin; the vinca alkaloid is vincristine and the platin derivative is cisplatin or carboplatin.

8. The method according to claim 5 further comprising administering to the subject at least one corticosteroid.

9. The method according to claim 8, wherein the corticosteroid is prednisone or prednisolone.

10. The method according to claim 5, wherein the active ingredient is administered in a dose between 50 mg to 1000 mg/m$^2$/per person per therapeutic cycle.

11. The method according to claim 5, wherein the dosage regimen comprises at least the administration of
a dose of 100 to 600 mg/m$^2$/per person of bendamustine on day 1 and day 2,
optionally a dose of 50 to 150 mg/m$^2$ i.v. or orally of a corticosteroid on days 1 to 5, and
optionally a suitable dose of a further active agent selected from the group consisting of an antibody specific for CD20, an anthracyclin derivative, a vinca alkaloid or a platin derivative; and the repetition of said dosage regimen 4 to 15 times after intervals of two to four weeks.

12. The method according to claim 5, wherein the active ingredient bendamustine is administered in a dosage regimen selected from 200-300 mg on day 1 and day 2, optionally followed by a maintenance dose of 50 mg once a day, 50 mg each day from day 1 up till and including day 14, or 150 mg once a week for 3 weeks.

13. The method according to claim 5, wherein the patient is suffering from non-Hodgkin's lymphoma and the dosage regimen comprises administering a total amount of 200 mg/person/day of active ingredient bendamustine on days 1 to 5, 2 mg i.v. of vincristine on day 1 and 100 mg/m$^2$ i.v. of prednisone on days 1 to 5 and repeating said treatment every three weeks until the non-Hodgkin's lymphoma has regressed.

14. The method according to claim 5, wherein the patient is suffering from multiple myeloma and the dosage regimen comprises administering an amount of 100-250 mg/m$^2$ body surface area bendamustine hydrochloride on days 1 and 2, 60 mg/m$^2$ i.v. or orally of prednisone on days 1 to 4 and repeating said treatment every four weeks until the multiple myeloma has regressed.

15. The method according to claim 5, wherein the patient is suffering from chronic lymphocytic leukaemia and the dosage regimen comprises administering an amount of 100 to 200 mg/m$^2$ body surface area bendamustine hydrochloride on days 1 and 2 and 60 mg/m$^2$ i.v. or orally of prednisone on days 1 to 4 and repeating said treatment every four weeks until the chronic lymphocytic leukaemia has regressed.

16. The method according claim 5, wherein the patient is suffering from follicular, indolent or mantle cell lymphoma and the dosage regimen comprises administering a dose of 375 mg/m$^2$ rituximab on day 1 plus 100 to 200, 130 mg/m$^2$ oral bendamustine on days 1 and 2 every 28 days until the respective lymphoma has regressed.

17. A pharmaceutical composition in an oral dosage form of a hard gelatine capsule which comprises a particulate suspension of bendamustine hydrochloride present as an active ingredient, and a pharmaceutically acceptable excipient which has a dissolution of the bendamustine of at least 60% in 20 minutes, 70% in 40 minutes and 80% in 60 minutes, as measured with a paddle apparatus at 50 rpm according to the European Pharmacopoeia in 500 ml of a dissolution medium at a pH of 1.5, wherein the pharmaceutically acceptable excipient is selected from the group consisting of macrogol glycerol hydroxystearate, polyoxyl-35-castor oil and ethylene oxide/propylene oxide block copolymer, wherein the composition further comprises colloidal silicon dioxide.

18. A pharmaceutical composition in an oral dosage form of a hard gelatine capsule which comprises a particulate suspension of bendamustine hydrochloride present as an active ingredient, and a pharmaceutically acceptable excipient which shows a dissolution of the bendamustine of at least 60% in 20 minutes, 70% in 40 minutes and 80% in 60 minutes, as measured with a paddle apparatus at 50 rpm according to the European Pharmacopoeia in 500 ml of a dissolution medium at a pH of 1.5, wherein the pharmaceutically acceptable excipient is selected from the group consisting of macrogol glycerol hydroxystearate, polyoxyl-35-castor oil and ethylene oxide/propylene oxide block copolymer, wherein the composition further comprises lauroyl macrogol glycerides.

\* \* \* \* \*